United States Patent
Yang et al.

(10) Patent No.: US 12,428,389 B2
(45) Date of Patent: Sep. 30, 2025

(54) DIARYLAMIDE COMPOUND AND APPLICATION THEREOF

(71) Applicant: Sunshine Lake Pharma Co., Ltd., Guangdong (CN)

(72) Inventors: Baoxue Yang, Beijing (CN); Runtao Li, Beijing (CN); Min Li, Beijing (CN); Shun Zhang, Beijing (CN); Yan Zhao, Beijing (CN); Shuyuan Wang, Beijing (CN)

(73) Assignee: SUNSHINE LAKE PHARMA CO., LTD., Guangdong (CN)

( * ) Notice: Subject to any disclaimer, the term of this patent is extended or adjusted under 35 U.S.C. 154(b) by 700 days.

(21) Appl. No.: 17/619,174

(22) PCT Filed: Jun. 19, 2020

(86) PCT No.: PCT/CN2020/096939
§ 371 (c)(1),
(2) Date: Dec. 14, 2021

(87) PCT Pub. No.: WO2020/253802
PCT Pub. Date: Dec. 24, 2020

(65) Prior Publication Data
US 2023/0045031 A1    Feb. 9, 2023

(30) Foreign Application Priority Data

Jun. 19, 2019   (CN) ......................... 201910531710.X

(51) Int. Cl.
| | | |
|---|---|---|
| *C07D 307/72* | (2006.01) | |
| *A61P 13/00* | (2006.01) | |
| *C07C 233/80* | (2006.01) | |
| *C07D 207/34* | (2006.01) | |
| *C07D 263/34* | (2006.01) | |
| *C07D 307/68* | (2006.01) | |
| *C07D 333/38* | (2006.01) | |
| *C07D 405/12* | (2006.01) | |

(52) U.S. Cl.
CPC ............ *C07D 307/72* (2013.01); *A61P 13/00* (2018.01); *C07C 233/80* (2013.01); *C07D 207/34* (2013.01); *C07D 263/34* (2013.01); *C07D 307/68* (2013.01); *C07D 333/38* (2013.01); *C07D 405/12* (2013.01)

(58) Field of Classification Search
CPC .. C07D 207/34; C07D 307/72; C07C 233/80; A61P 13/00
See application file for complete search history.

(56) References Cited

FOREIGN PATENT DOCUMENTS

| CN | 102757447 A | 10/2012 |
|---|---|---|
| CN | 104602682 A | 5/2015 |
| CN | 104825454 A | 8/2015 |
| JP | 2007126454 | * 5/2007 |
| JP | 2007126454 A | 5/2007 |

OTHER PUBLICATIONS

Robert et al. (Eur. J. Med. Chem. (1995) 30:915-924). (Year: 1995).*
Li, M., et al., "Developing Hypothetical Inhibition Mechanism of Novel Urea Transporter B Inhibitor", Scientific Reports, Jul. 22, 2014, vol. 4, article 5775, pp. 1-12.
Meng, Y., et al., "Research Progress of Urea Channel Protein", Foreign Medical Sciences (Pathophysiology and Clinical Medicine)), Aug. 31, 2004, vol. 24(4), pp. 349-351, (Reference and English Abstract).
Robert, J.M.H., et al., "Non-Carboxylic Antiinflammatory Compounds. III. N-(4,6-Dimethylpyridin-2-yi) arylcarboxamides and Arylthiocarboxamides Acting as Brain Edema Inhibitors", Eur. J. Med. Chem., Dec. 31, 1995, vol. 30(12), pp. 915-924.
Smith, C.P. and Rousselet, G., "Facilitative Urea Transporters", J. Membrane Biol., 2001, vol. 183, pp. 1-14.
Yang, B., et al., "Urea-Selective Concentrating Defect in Transgenic Mice Lacking Urea Transporter UT-B", J. Biol. Chem., 2002, vol. 277, pp. 10633-10637.
Zhao, Dan, et al., "Comparative Transport Efficiencies of Urea Analogues Through Urea Transporter UT-B", Biochimica et Biophysica Acta., Jul. 31, 2007, vol. 1768(7), pp. 1815-1821.
Bagnasco, S.M., "Gene Structure of Urea Transporters", Am. J. Physiol. Renal Physiol., Jan. 2003, vol. 284(1), pp. F3-F10.
Bankir, L., et al., "Lack of UT-B in Vasa Recta and Red Blood Cells Prevents Urea-Induced Improvement of Urinary Concentrating Ability", Am. J. Physiol. Renal Physiol., Jan. 2004, vol. 286(1), pp. F144-F151.
Fenton, R.A., et al., "Urinary Concentrating Defect in Mice with Selective Deletion of Phloretin-Sensitive Urea Transporters in the Renal Collecting Duct", Proc. Natl. Acad. Sci., May 11, 2004, vol. 101(19), pp. 7469-7474.
Fenton, R. A., et al., "Renal Phenotype of UT-A Urea Transporter Knockout Mice", J. Am. Soc. Nephrol., Jun. 2005, vol. 16(6), pp. 1583-1592.
Jiang, T., et al., "Generation and Phenotypic Analysis of Mice Lacking All Urea Transporters", Kidney Int., 2016, vol. 91(2), pp. 338-351.

(Continued)

*Primary Examiner* — Marcos L Sznaidman
(74) *Attorney, Agent, or Firm* — Oliff PLC

(57) ABSTRACT

A use of a diarylamide compound having the structure as shown in formula (I) or a pharmaceutically acceptable salt thereof in preparing a drug which acts as a urea transporter protein inhibitor, and a novel diarylamide compound. The diarylamide compound has urea transporter protein inhibitor effect, and can produce urea selective diuresis in the body without obvious toxicity.

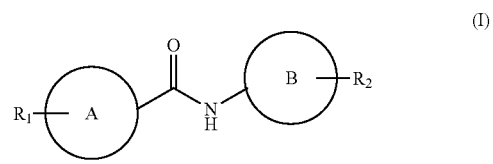

(I)

10 Claims, 4 Drawing Sheets

(56) References Cited

OTHER PUBLICATIONS

Sands, J.M., "Renal Urea Transporters", Curr. Opin. Nephrol. Hypertens., Sep. 2004, vol. 13(5), pp. 525-532.
Shayakul, C. and Hediger, M.A., "The SLC14 Gene Family of Urea Transporters", Pfluegers Arch.—Eur. J. Physiol., Feb. 2004, vol. 447(5), pp. 603-609.
Smith, C.P., and Rousselet, G., "Facilitative Urea Transporters", J. Membrane Biol., Sep. 1, 2001, vol. 183(1), pp. 1-14.
Yang, B., et al., "Urea-Selective Concentrating Defect in Transgenic Mice Lacking Urea Transporter UT-B", J. Biol. Chem., Mar. 22, 2002, vol. 277(12), pp. 10633-10637.
Yang, B. and Bankir, L., "Urea and Urine Concentrating Ability: New Insights from Studies in Mice", Am. J. Physiol. Renal Physiol., May 2005, vol. 288(5), pp. F881-F896.

* cited by examiner

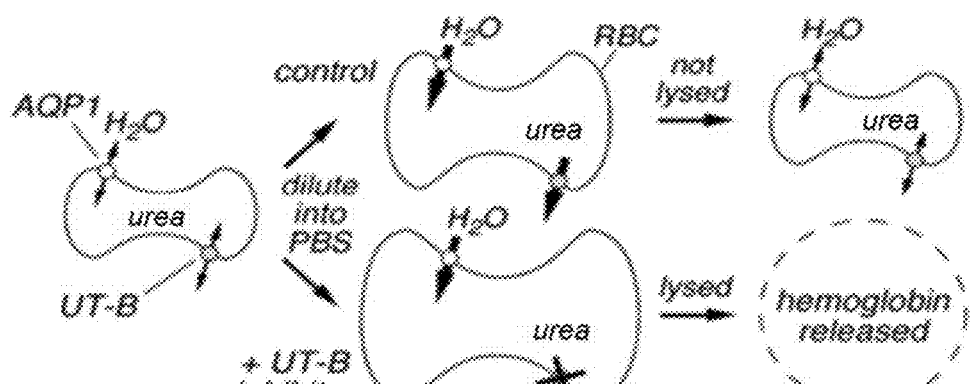
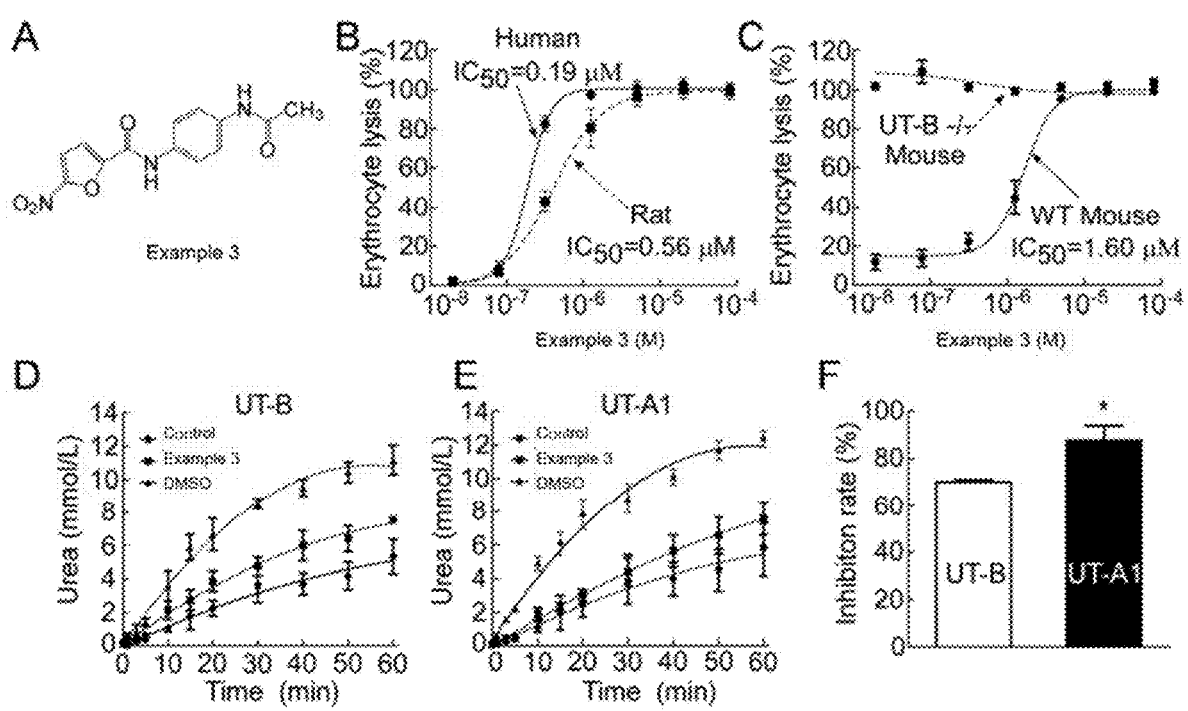

DIARYLAMIDE COMPOUND AND APPLICATION THEREOF

CROSS-REFERENCE TO RELATED APPLICATIONS

This application is a section 371 U.S. national phase application of International application no. PCT/CN2020/096939, filed Jun. 19, 2020, which in turn claims the priority and benefits of the Chinese patent application No. 201910531710.X, filed on Jun. 19, 2019 in the China National Intellectual Property Administration, the disclosures of which are incorporated herein by reference in their entireties.

FIELD OF THE INVENTION

The present invention relates to the field of diuretics, in particular to a diarylamide compound, a pharmaceutically acceptable salt thereof and use thereof in preparing a drug as a urea transporter inhibitor.

BACKGROUND OF THE INVENTION

1. Current Application and Research Hotspots of Diuretics

Diuretics act on the kidneys to increase the excretion of water. Clinically, they are mainly used to treat edema caused by various reasons, and can be also used to treat some non-edematous diseases. For example, as first-line drugs, they can be used alone or in combination with other drugs to treat hypertension, and reduce the incidence and death rate of cardiovascular and cerebrovascular diseases. Diuretics can be divided into potassium-sparing diuretics, thiazide diuretics, loop diuretics, and carbonic anhydrase inhibitors, according to the different sites of actions of diuretics. Potassium-sparing diuretics represented by amiloride and triamterene mainly exert diuretic effect by directly blocking the exchange of $Na^+$, $K^+$ and $H^+$. In addition, potassium-sparing diuretics can also exert a diuretic effect by indirectly regulating the level of aldosterone. Thiazide diuretics mainly exert a diuretic effect by acting on the $Na^+$—$Cl^-$ cotransporter of the distal convoluted tubules and collecting ducts to hinder the reabsorption of NaCl. Loop diuretics exert a diuretic effect by acting on the $Na^+$—$K^+$-$2Cl^-$ cotransporter of the medullary loop to hinder the reabsorption of NaCl. Since this part is the main part for NaCl reabsorption, it has a significant effect on urine concentration. Therefore, loop diuretics have a stronger diuretic effect. However, while exerting a diuretic effect, it will lead to increased excretion of $Na^+$, $K^+$, and $Cl^-$. Therefore, long-term use of diuretics can cause adverse reactions such as water and electrolyte imbalance, insufficient blood volume, metabolic acid-base imbalance, as well as blood lipid and glucose disorder. Therefore, the development of new diuretics that do not cause electrolyte disturbances is a hotspot in the field of diuretic research and development.

Vasopressin V2 receptor antagonists are a class of drugs that specifically antagonize the binding of vasopressin to the receptor thereof, which can phosphorylate aquaporin 2 (AQP2) in the vesicles in the main cells of the collecting duct of the kidney and make it insert into the apical plasma membrane of the cell, increasing the reabsorption of water in the collecting tube, thereby exerting a diuretic effect. Vasopressin V2 receptor antagonists are suitable for diseases such as normal volume and hypervolemic hyponatremia, but not entirely ideal as diuretics, since the downstream pathways of V2 receptors are more complicated, which can cause liver toxicity and other adverse effects. Therefore, we hope to find a new type of diuretics that can exert a diuretic effect without causing side effects such as electrolyte disturbances.

Urea transporter (UT) is a specific urea-permeable transmembrane protein that plays a very important role in the mechanism of urine concentration. Selective knockout of the urea transporter can block the urea circulation pathway in the kidney, reduce the ability of urine concentration, and produce urea selective diuresis without affecting the excretion of $Na^+$, $K^+$, and $Cl^-$. Therefore, urea transporter inhibitors can be used as diuretics to reduce the intrarenal osmotic pressure difference established by the intrarenal urea cycle without significantly affecting the body's electrolyte balance, thereby producing diuretic effects and being used to treat patients suffering edema diseases caused by different reasons (such as congestive heart failure, liver cirrhosis, nephrotic syndrome, etc.) and patients suffering from non-edema diseases (such as heart failure, cardiovascular and cerebrovascular diseases, etc.).

2. Urine Concentration Mechanism and Urea Cycle Process in the Kidney

Normal people produce about 180 liters of original urine per day, but the actual final urine volume excreted per day is only about 1.5 liters. Urea is the most abundant solute in urine, accounting for 40-50% of the total solute in urine. The concentration of urea in urine can be 100 times higher than the concentration of urea in plasma [Yang B and Bankir L. Renal handling of urea in transgenic mice lacking the urea transporter UT-B, *Am J Physiol Renal Physiol*, 2005, 288: F881-F896]. Urea is the main solute involved in the mechanism of urine concentration, has gradually increased concentration from the outer medulla to the inner medulla, and forms osmotic pressure gradient with sodium chloride from the renal cortex to the renal medulla, by the mechanism of intrarenal urea circulation through the process of countercurrent multiplication and countercurrent exchange, thereby the kidney can effectively concentrate urine so that water and certain solutes are effectively reabsorbed. The mechanism of intrarenal urea circulation specifically includes: (1) the reabsorption of water and the impermeability of urea by the collecting duct under the control of vasopressin lead to high-concentrated urea in the collecting duct; (2) the increased permeability of the end of the inner medullary collecting duct to urea allows the high-concentrated urea to penetrate into the interstitial tissue of the inner medulla; (3) medullary urea is continuously carried by the blood to the renal cortex through the ascending branches of the inner medulla, and is brought back to the medulla through the permeation of urea by the specific segments of the fine segments of the descending branch of the medullary loop and the descending branches of the small blood vessels, thereby maintaining the urea gradient and osmotic pressure gradient from the renal cortex to the renal medulla. This process is very important in the mechanism of urine concentration [Sands J M. Renal urea transporters, *Curr Opin Nephrol Hypertens,* 2004, 13: 525-532]. Except that the endothelial cells of the ascending branches of the inner medullary straight small blood vessels permeate urea in a microporous manner, the permeability of the above-mentioned parts to urea is mediated by the urea transporter [Smith C P and Rousselet G. Facilitative Urea transporters, *J MembrancBiol,* 2001, 183: 1-14].

Urea transporter is a membrane transporter protein that specifically permeates urea. At present, 7 members have been cloned, belonging to two subfamilies UT-A and UT-B respectively. The UT-A subfamily includes 6 members (UT- A1 to UT-A6) produced from the same gene (Slc14a2) via the regulation of different promoters and post-transcriptional splicing [Bagnasco S M. Gene structure of urea transporters, *Am J Physiol,* 2003, 284: F3-F10; Shayakul C and Hediger M A. The SLC14 gene family of urea transporters, *Pfluegers Arch,* 2004, 447:603-609], and the UT-B subfamily has only one member, UT-B. There are 5 urea transporters expressed in different parts of the kidney, UT-A1, UT-A3, and UT-A4 (UT-A4 is only expressed in rats) are expressed in the epithelial cells of the renal collecting duct, and UT-A2 is expressed in fine segments of the descending branch of the renal medullary loop, UT-A5 and UT-A6 are expressed in the testis and colon respectively. UT-B is expressed by another gene (Slc14a1), which is located in the endothelial cells of the descending branches of the straight small blood vessels of the kidney, erythrocytes, and various tissues and organs. UT-A1, UT-A2, UT-A3, UT-A4 and UT-B mediate the urea permeability of the corresponding parts of the urea cycle in the kidney, play an important role in the process of the urea cycle in the kidney, and participate in the mechanism of urine concentration.

3. Functional Knockout of Urea Transporter can Produce Urea Selective Diuretic Effect and Lower Blood Pressure The study results of the renal physiology performed by using the urea transporter gene knockout mouse model [Yang B, Bankir L, Gillepsie A. Urea-selective concentrating defect in transgenic mice lacking urea transporter UT-B, *J Biol Chem,* 2002, 277: 10633-10637] show that, mice lacking UT-B does not show abnormal growth and development. UT-B knockout does not affect the glomerular filtration rate, kidney weight, clearance of major solutes ($Na^+$, $K^+$, $Cl^-$) in urine other than urea. However, its urine concentration ability has changed significantly: urine volume increases, urine osmotic pressure decreases, and the ratio of urine urea to blood urea concentration is only 50% of that of wild-type mice. Experimental results show that, the urea transport mediated by UT-B in the straight small blood vessels of the kidney accounts for one-third of the total urine concentration capacity of the kidney [Bankir L, Chen K and Yang B. Renal handling of urea in transgenic mice lacking the urea transporter UT-B, *Am J Physiol,* 2004, 286: F144-F151]. Under basic conditions, UT-A1/UT-A3 gene-deficient mice have a urine concentration ability reduced to 35% of that of wild-type mice, and their urine volume is three times higher than that of wild-type mice. Moreover, their urine osmotic pressure does not increase after 5 days of strictly controlling fluid intake. The accumulation of urea in the kidney inner medulla of UT-A1/UT-A3 knockout mice is also significantly reduced (⅓ of the normal level) [Fenton R A, Chou C L, Stewart G S. Urinary concentrating defect in mice with selective deletion of phloretin-sensitive urea transporters in the renal collecting duct, *Proc Natl Acad Sci,* 2004, 101: 7469-7474; Fenton, R. A., Flynn A, Shodeinde A. Renal phenotype of UT-A urea transporter knockout mice, *J Am Soc Nephrol.* 2005, 16: 1583-1592]. All UT knockout mice show significant polyuria, and the average daily urine volume is about three times that of wild-type mice. After water deprivation, the urine osmotic pressure of wild-type mice increases significantly, while that of all UT knockout mice increases more slowly. Therefore, the HE stained sections show that, the renal cortex and outer medulla of wild-type mice and all UT knockout mice do not have any histological abnormalities. In the kidney inner medulla of all UT knockout mice, the collecting duct dilation could be observed, while the wild type mice do not have this phenomenon [Jiang, T., Li, Y., Layton, A. T., Wang, W., Sun, Y., Li, M., Zhou, H., and Yang, B. (2017). Generation and phenotypic analysis of mice lacking all urea transporters. Kidney Int 91, 338-351]. Thus, selective knockout of UT-B or UT-A1/UT-A3 can block renal urea circulation passage, reduce urine concentration ability, produce selective urea diuretic effect without affecting $Na^+$, $K^+$, $Cl^-$. Therefore, urea transporter inhibitors can act on the kidneys as diuretics and increase the excretion of water, thus can be used clinically to treat water retention diseases such as congestive heart failure, nephrotic syndrome, and edema.

SUMMARY OF THE INVENTION

Through the computer high-throughput screening and reasonable drug design methods, the present invention discovers a class of diarylamide compounds and a pharmaceutically acceptable salt thereof, which have good urea transporter inhibitory activity and excellent druggability.

As the first aspect of the present invention, the present invention describes use of a compound represented by formula (I) or a pharmaceutically acceptable salt thereof in preparing a drug as a urea transporter inhibitor,

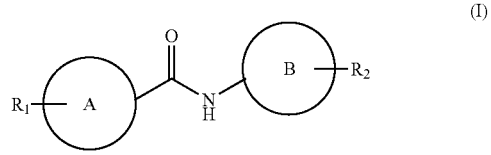

wherein, ring A and ring B are each independently a 5- to 6-membered heteroaryl group or a 5- to 6-membered aryl group;

ring A and ring B are optionally substituted with $R_1$ and $R_2$ respectively;

$R_1$ is selected from the group consisting of nitro, halogen, alkyl, alkylcarbonyl, alkylcarbonylamino, alkylsulfonyl and pyrido groups;

$R_2$ is selected from the group consisting of halogen, hydroxy, amino, cyano, alkyl, alkenyl, alkynyl, hydroxyalkyl, aminoalkyl, alkoxy, alkylcarbonyl, alkoxycarbonyl, pyrido, alkylcarbonylamino optionally substituted with $R_5$, heterocyclic or cyclic group optionally substituted with $R_5$, heteroarylcarbonylamino optionally substituted with $R_5$, N-alkylamino, N,N-di(alkyl)amino, and aminocarbonyl substituted with $R_3$ and $R_4$;

wherein, $R_3$ and $R_4$ are each independently selected from the group consisting of H, hydroxyl, alkyl, heterocyclic or cyclic group optionally substituted with $R_5$, heterocyclic or cyclic alkyl optionally substituted with $R_5$, heteroaryl or aryl alkyl optionally substituted with $R_5$, N-(alkyl)aminoalkyl, and N,N-di(alkyl)aminoalkyl; and $R_5$ is selected from the group consisting of alkyl, nitro, alkylcarbonylamino, N-(alkyl)amino, N,N-di(alkyl)amino, N,N-di(alkyl)aminoalkylamino, and heterocyclic or cyclic group.

As the second aspect of the present invention, the present invention also describes the method for treating or preventing diseases related to a urea transporter inhibitor, comprising administering a therapeutically effective amount of the compound represented by formula (I) according to the present invention or the pharmaceutically acceptable salt thereof.

As the third aspect of the present invention, the present invention also describes the compound represented by formula (I) according to the present invention, or the pharmaceutically acceptable salt thereof for use in treating or preventing diseases related to a urea transporter inhibitor.

As the fourth aspect of the present invention, the present invention also describes the compound represented by formula (I) according to the present invention, or the pharmaceutically acceptable salt thereof for use as a urea transporter inhibitor.

As the fifth aspect of the present invention, the present invention also describes use of the compound represented by formula (I) according to the present invention, or the pharmaceutically acceptable salt thereof in the treatment of diseases related to a urea transporter inhibitor.

As the sixth aspect of the present invention, the present invention describes a diarylamide compound or a pharmaceutically acceptable salt thereof, the diarylamide compound or the pharmaceutically acceptable salt thereof is selected from the group consisting of the following compounds, or the pharmaceutically acceptable salts thereof:

(15) N-(pyridazin-3-yl)-5-nitrofuran-2-carboxamide;
(17) N-(thiophen-3-yl)-5-nitrofuran-2-carboxamide;
(25) N-(4-acetamidophenyl)-5-methylsulfonylfuran-2-carboxamide;
(26) N-(2-acetamidophenyl)-5-nitrofuran-2-carboxamide;
(51) N-(4-aminomethylphenyl)-5-nitrofuran-2-carboxamide;
(53) N-(3-(methylcarbamoyl)phenyl)-5-nitrofuran-2-carboxamide;
(55) N-(3-(ethylcarbamoyl)phenyl)-5-nitrofuran-2-carboxamide;
(56) N-(3-(isopropylcarbamoyl)phenyl)-5-nitrofuran-2-carboxamide;
(57) N-(3-(isobutylcarbamoyl)phenyl)-5-nitrofuran-2-carboxamide;
(58) N-(3-(cyclohexylcarbamoyl)phenyl)-5-nitrofuran-2-carboxamide;
(59) N-(3-(benzylcarbamoyl)phenyl)-5-nitrofuran-2-carboxamide;
(60) N-(3-((2-dimethylaminoethyl)carbamoyl)phenyl)-5-nitrofuran-2-carboxamide;
(61) N-(3-((2-morpholinylethyl)carbamoyl)phenyl)-5-nitrofuran-2-carboxamide;
(62) N-(3-((3-morpholinylpropyl)carbamoyl)phenyl)-5-nitrofuran-2-carboxamide;
(63) N-(4-methyl-3-methylcarbamoylphenyl)-5-nitrofuran-2-carboxamide;
(64) N-(5-methyl-3-methylcarbamoylphenyl)-5-nitrofuran-2-carboxamide;
(65) N-(4-fluoro-3-methylcarbamoylphenyl)-5-nitrofuran-2-carboxamide;
(66) N-(5-fluoro-3-methylcarbamoylphenyl)-5-nitrofuran-2-carboxamide;
(67) N-(4-hydroxy-3-methylcarbamoylphenyl)-5-nitrofuran-2-carboxamide;
(68) $N^1,N^3$-dimethyl-5-(5-nitrofuran-2-carboxamido)isophthalamide;
(69) N-(2-methyl-1,3-dihydro-1,3-dioxo-2H-isoindol-5-yl)-5-nitrofuran-2-carboxamide;
(70) N-(4-acetamidophenyl)-5-acetylfuran-2-carboxamide;
(71) N-(4-(2-dimethylamino)acetamidophenyl)-5-nitrofuran-2-carboxamide;
(72) N-(4-(2-morpholinyl)acetamidophenyl)-5-nitrofuran-2-carboxamide;
(73) N-(4-(3-dimethylamino)propionamidophenyl)-5-nitrofuran-2-carboxamide;
(74) N-(4-((2-dimethylamino)ethylamino)acetamidophenyl)-5-nitrofuran-2-carboxamide;
(75) ethyl 2-acetamido-5-(5-nitrofuran-2-carboxamide)benzoate;
(76) ethyl 5-(5-nitrofuran-2-carboxamide)-1H-pyrazole-4-carboxylate;
(77) ethyl 5-(5-nitrofuran-2-carboxamide)-1H-pyrazole-3-carboxylate; and
(78) 3-(5-acetyl-2-furoyl)carbamamide.

As the seventh aspect of the present invention, the present invention describes a pharmaceutical composition comprising: the diarylamide compound according to the sixth aspect of the present invention or the pharmaceutically acceptable salt thereof; and a pharmaceutically acceptable carrier.

The present invention screens out 1,040 compounds from small molecule compound libraries by using computer simulation screening, screens out compounds having UT-B inhibitory activity by an erythrocyte lysis model, and obtains a class of diarylamide compounds having stronger UT-B inhibitory activity by combining structural modification and optimization. This class of diarylamide compounds has a strong inhibitory activity on UT-B and UT-A for permeating urea, and their half-effective dose for inhibiting urea transporter UT-B in vitro is below the micromolar level, without obvious cytotoxicity. It is found in in vivo experiments that: subcutaneous and oral administration of these diarylamide compounds can significantly increase the urine volume of rats and mice, reduce the level of urine urea, and reduce the urine osmotic pressure at the same time, indicating that they have an excellent urea selective diuretic effect, and these compounds do not affect the electrolyte balance of body fluid. The diarylamide compound of the present invention has the potential to be developed into a new type of diuretics, can avoid the common side effects of conventional diuretics such as electrolyte disturbances, and can be used to treat patients suffering edema diseases caused by different reasons (such as congestive heart failure, liver cirrhosis, nephrotic syndrome, etc.) and patients suffering from non-edema diseases (such as heart failure, cardiovascular and cerebrovascular diseases, etc.).

DESCRIPTION OF THE DRAWINGS

FIG. 1 is a schematic diagram of a screening model of erythrocyte urea transporter inhibitors.

FIG. 2 exemplarily shows the inhibitory effect of the compound of Example 3 of the present invention (hereinafter referred to as Example 3 or the compound of Example 3) on UT-B and UT-A1 for permeating urea. A: the chemical structure of the compound of Example 3; B: the dose-effect relationship of the compound of Example 3 on the inhibitory effect of human and rat UT-B in the erythrocyte lysis model; C: the dose-effect relationship of PU-48 on the inhibition of erythrocyte urea permeability in wild type or UT-B knockout mice; D: the inhibitory effect of the compound of Example 3 on the urea transport ability of MDCK cells stably transfected with UT-B; E: the inhibitory effect of the compound of Example 3 on the urea transport ability of MDCK cells stably transfected with UT-A1; F: the inhibitory rate of the compound of Example 3 on the urea transport of MDCK cells stably transfected with UT-B or UT-A1. Data are shown as means ±standard error, n=3; *P<0.01, representing the inhibitory rate of the compound of Example 3 on the urea transport of MDCK cells stably transfected with UT-B compared with the inhibitory rate on the urea transport of MDCK cells stably transfected with UT-A1.

FIG. 3 exemplarily shows the diuretic effect and non-urea excretion of a single subcutaneous injection of the compound of Example 3 of the present invention in rats. The rats were put into a metabolic cage, and urine of 0~2 h was collected as the basal urine volume. Then, the experimental group was subcutaneously administrated with 100 mg/kg of the compound of Example 3, and the control group was administrated with corn oil. A: urine volume; B: osmotic pressure; C: non-urea solute excretion. The results are shown as means±standard error, n=6, *p<0.05, P<0.01, *P<0.001, representing the rats in the group administrated with the compound of Example 3 compared with the rats in the solvent control group; #P<0.05, ###P<0.001, representing the level after administrating with the compound of Example 3 compared with the basal level.

DETAILED DESCRIPTION OF THE INVENTION

Figure 4:
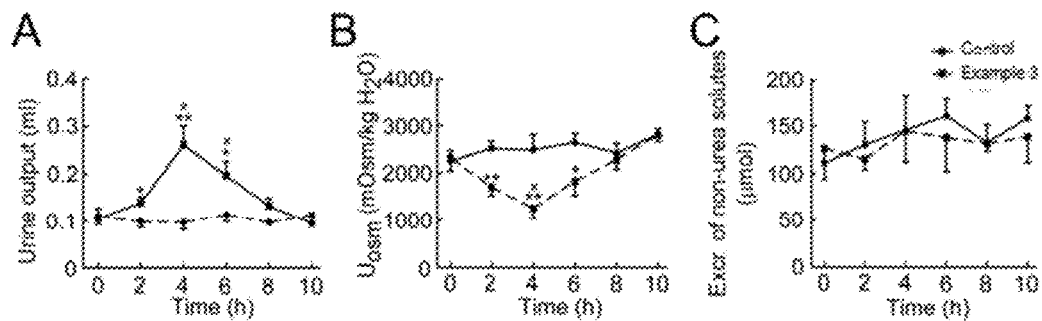
FIG. 4 exemplarily shows the diuretic effect and non-urea excretion of a single subcutaneous injection of the compound of Example 3 of the present invention in mice. The mice were put into a metabolic cage, and urine of 0~2 h was collected as the basal urine volume. Then, the experimental group was subcutaneously administrated with 100 mg/kg of the compound of Example 3, and the control group was administrated with corn oil. A: urine volume; B: osmotic pressure; C: non-urea solute excretion. The results are shown as means±standard error, n=6, *P<0.05, **P<0.01, representing the mice in the group administrated with the compound of Example 3 compared with the mice in the solvent control group; #P<0.05, representing the level after administrating with the compound of Example 3 compared with the basal level.

The embodiments of the present invention will be described in detail below. However, the present invention is not limited to the following description, and the ordinary skilled in the art to which this invention belongs can easily understand that the mode and details can be changed into various forms. In addition, the present invention should not be interpreted as only being limited to the contents described in the embodiments shown below.

As used herein, the term "alkyl" refers to a group consisting of carbon and hydrogen atoms only, without any units of unsaturation (e.g., double bond, triple bond, or cycle), including any possible geometric isomers and stereoisomers. An alkyl group attaches to the rest of a molecule through a single bond. As non-limiting examples of alkyl, the following straight-chain or branched-chain groups may be exemplified: methyl, ethyl, n-propyl, isopropyl, n-butyl, isobutyl, sec-butyl, tert-butyl, n-pentyl and other seven isomers thereof, n-hexyl and other sixteen isomers thereof. The description of the number of carbon atoms in the present invention includes both endpoints and all integer values therebetween, for example: $C_{1-6}$ alkyl includes methyl, ethyl, propyl, butyl, pentyl, hexyl and all isomers thereof.

As used herein, the term "alkenyl" refers to a linear, branched or cyclic unsaturated hydrocarbon atomic group having at least one carbon-carbon double bond. For example, $C_{2-6}$ alkenyl includes alkenyl groups having a chain of 2 to 6 carbons and at least one double bond (e.g., vinyl, allyl, propenyl, isopropenyl, 1-butenyl, 2-butenyl, 3-butenyl, 2-methylallyl, 1-hexenyl, 2-hexenyl, 3-hexenyl, etc.).

As used herein, the term "alkynyl" refers to an unsaturated hydrocarbon atomic group having at least one carbon-carbon triple bond. For example, $C_{2-6}$ alkynyl groups include alkynyl groups having a chain of 2 to 6 carbons and at least one triple bond (e.g., ethynyl, 1-propynyl, 2-propynyl, 1-butynyl, isopentynyl, 1,3-hexadiynyl, n-hexynyl, 3-pentynyl, 1-hexen-3-ynyl, etc.).

As used herein, the term "cyclic group" refers to a saturated non-aromatic ring system composed of at least 3 carbon atoms. The ring system can be monocyclic, bicyclic, polycyclic, fused, bridged, or spiro ring. As non-limiting examples of cycloalkyl groups, the following groups can be exemplified: cyclopropyl, cyclobutyl, cyclopentyl, cyclohexyl; and fused, bridged, or spiro ring groups formed by two or more of the above-mentioned monocyclic rings through common edges and common carbon atoms.

As used herein, the term "alkoxy" refers to a group where an alkyl group above connects to oxygen atom, through which it connects to the rest of a molecule via a single bond, including any possible geometric isomers and stereoisomers. As non-limiting examples of alkoxy, the following straight-chain or branched-chain groups can be exemplified: methoxy, ethoxy, n-propoxy, isopropoxy, n-butoxy, isobutoxy, s-butoxy, t-butoxy, n-pentoxy and other seven isomers thereof, n-hexyloxy and other sixteen isomers thereof.

As used herein, the term "aryl" refers to an aromatic 5- to 10-membered monocyclic ring, an aromatic 8- to 12-membered fused bicyclic ring or an aromatic 11- to 14-membered fused tricyclic ring system. For example, a 5- or 6-membered aryl means that the number of carbon atoms in the ring system is 5 or 6. In some embodiments, 1, 2, 3, or 4 hydrogen atoms in each ring may be replaced by substituents.

As used herein, the term "heteroaryl" refers to a 5- to 14-membered aromatic heterocyclic group having one or more heteroatoms independently selected from N, O or S, which can be monocyclic, bicyclic, or polycyclic, wherein the bicyclic or polycyclic ring can be formed by monocyclic rings through a single bond connection or in a fused manner. As non-limiting examples of heteroaryl, the following groups can be exemplified: oxazolyl, isoxazolyl, imidazolyl, furanyl, indolyl, isoindolyl, pyrrolyl, triazolyl, triazinyl, tetrazolyl, thienyl, thiazolyl, isothiazolyl, pyridinyl, pyrimidinyl, pyrazinyl, pyridazinyl, benzofuranyl, benzothiazolyl, benzoxazolyl, benzimidazolyl, benzothienyl, benzopyranyl, carbazolyl, quinolyl, isoquinolyl, quinazolinyl, cinnolinyl, naphthyridinyl, pteridinyl, purinyl, quinoxalinyl, thiadiazolyl, indolizinyl, acridinyl, phenazinyl, phthalazinyl, coumarinyl, pyrazolo-pyridinyl, pyridino-pyridazinyl, pyrrolopyridinyl, imidazo-pyridinyl, pyrazolo-pyridazinyl, and groups formed by the above heteroaryl groups through a single bond connection or in a fused manner.

As used herein, the term "heterocyclyl" refers to a 3- to 15-membered non-aromatic ring group consisting of carbon atoms and heteroatoms independently selected from N, O or S, which can be monocyclic, bicyclic, or polycyclic, also can be fused, bridged, or spiro, and can optionally contain one or more double bonds. As non-limiting examples of heterocyclyl, the following groups can be exemplified: oxiranyl, thiorenyl, aziridinyl, oxetanyl, thietanyl, azetidinyl, tetrahydrofuranyl, tetrahydrothienyl, pyrrolidinyl, tetrahydropyranyl, tetrahydrofuranyl, piperidinyl, 1,4-dioxanyl, 1,4-oxathianyl, morpholinyl, 1,4-dithianyl, piperazinyl, 1,4-azathiane, 3,4-dihydro-2H-pyranyl, 5,6-dihydro-2H-pyranyl, 1,2,3,4-tetrahydropyridinyl, 1,2,5,6-tetrahydropyridinyl.

As used herein, the term "halogen" refers to fluorine, chlorine, bromine or iodine.

As used herein, the term "N-(alkyl)amino or N,N-di(alkyl)amino" refers to —NH alkyl or —N(alkyl)$_2$ respectively, for example, —NHCH$_3$, —N(CH$_3$)$_2$ and so on.

Through all the above descriptions, it is clear to the skilled person that any group which name is a composite name such as, alkylsulfonyl has to be intended as conventionally construed by the parts from which it derives, e.g. by a sulfonyl group which is further substituted by an alkyl, wherein the alkyl is as above defined.

The term "preventing or treating" means administering the compound or formulation described in this application to prevent, ameliorate or eliminate a disease or one or more symptoms associated with the disease, and includes:
(i) preventing the occurrence of a disease or disease state in a mammal, especially when such a mammal is susceptible to the disease state, but has not been diagnosed as having the disease state;
(ii) inhibiting the disease or disease state, that is, curbing its development;
(iii) alleviating the disease or disease state, even if the disease or disease state resolves.

The term "therapeutically effective amount" means an amount of the compound of the present application capable of (i) treating or preventing the particular disease, condition or disorder, (ii) reducing, ameliorating or eliminating one or more symptoms of the particular disease, condition or disorder, or (iii) preventing or delaying the onset of one or more symptoms of the particular disease, condition, or disorder described herein. The amount of the compound of the present application that constitutes a "therapeutically effective amount" varies depending on the compound, the disease state and its severity, the mode of administration, and the age of the mammal to be treated, but it can be routinely determined by the skilled in the art by own knowledge thereof and the present disclosure.

In some embodiments, the present invention describes use of the compound represented by formula (I) or the pharmaceutically acceptable salt thereof in preparing a drug as a urea transporter inhibitor,

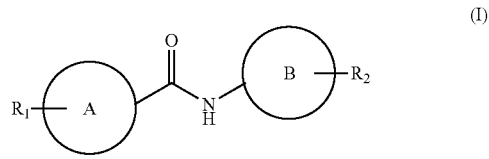

(I)

wherein, ring A and ring B are each independently a 5- to 6-membered heteroaryl group or a 5- to 6-membered aryl group;

ring A and ring B are optionally substituted with $R_1$ and $R_2$ respectively;

$R_1$ is selected from the group consisting of nitro, halogen, alkyl, alkylcarbonyl, alkylcarbonylamino, alkylsulfonyl and pyrido groups;

$R_2$ is selected from the group consisting of halogen, hydroxy, amino, cyano, alkyl, alkenyl, alkynyl, hydroxyalkyl, aminoalkyl, alkoxy, alkylcarbonyl, alkoxycarbonyl, pyrido, alkylcarbonylamino optionally substituted with $R_5$, heterocyclic or cyclic group optionally substituted with $R_5$, heteroarylcarbonylamino optionally substituted with $R_5$, N-alkylamino, N,N-di(alkyl)amino, and aminocarbonyl substituted with $R_3$ and $R_4$;

wherein, $R_3$ and $R_4$ are each independently selected from the group consisting of H, hydroxyl, alkyl, heterocyclic or cyclic group optionally substituted with $R_5$, heterocyclic or cyclic alkyl optionally substituted with $R_5$, heteroaryl or aryl alkyl optionally substituted with $R_5$, N-(alkyl)aminoalkyl, and N,N-di(alkyl)aminoalkyl; and $R_5$ is selected from the group consisting of alkyl, nitro, alkylcarbonylamino, N-(alkyl)amino, N,N-di(alkyl)amino, N,N-di(alkyl)aminoalkylamino, and heterocyclic or cyclic group.

In some embodiments, the definitions of the above each group satisfy one or more of the followings:

$R_1$ is selected from the group consisting of nitro, halogen, $C_{1-6}$ alkyl, $C_{1-6}$ alkylcarbonyl, $C_{1-6}$ alkylcarbonylamino, $C_{1-6}$ alkylsulfonyl and pyrido groups;

$R_2$ is selected from the group consisting of halogen, hydroxyl, amino, cyano, $C_{1-6}$ alkyl, $C_{2-6}$ alkenyl, $C_{2-6}$ alkynyl, hydroxy $C_{1-6}$ alkyl, amino $C_{1-6}$ alkyl, $C_{1-6}$ alkoxy, $C_{1-6}$ alkylcarbonyl, $C_{1-6}$ alkoxycarbonyl, pyrido, $C_{1-6}$ alkylcarbonylamino optionally substituted with $R_5$, 5- to 6-membered heterocyclic or cyclic group optionally substituted with $R_5$, 5- to 6-membered heteroarylcarbonylamino optionally substituted with $R_5$, N—($C_{1-6}$ alkyl)amino, N,N-di($C_{1-6}$ alkyl)amino, and aminocarbonyl substituted with $R_3$ and $R_4$;

wherein, $R_3$ and $R_4$ are each independently selected from the group consisting of H, hydroxyl, $C_{1-6}$ alkyl, 5- to 6-membered heterocyclic or cyclic group optionally substituted with $R_5$, 5- to 6-membered heterocyclic or cyclic $C_{1-6}$ alkyl optionally substituted with $R_5$, 5- to 6-membered heteroaryl or aryl $C_{1-6}$ alkyl optionally substituted with $R_5$, N—($C_{1-6}$ alkyl)amino $C_1$-$C_6$ alkyl, and N,N-di($C_{1-6}$ alkyl)amino $C_{1-6}$ alkyl; and $R_5$ is selected from the group consisting of $C_{1-6}$ alkyl, nitro, $C_{1-6}$ alkylcarbonylamino, N—($C_{1-6}$ alkyl)amino, N,N-di($C_{1-6}$ alkyl)amino, N,N-di($C_{1-6}$ alkyl)amino $C_{1-6}$ alkylamino, and 5- to 6-membered heterocyclic or cyclic group.

In some embodiments, the heteroatoms of the heteroaryl group and the heterocyclic group are independently selected from O, S and/or N, and the number of heteroatoms is selected from an integer of 1, 2, 3.

In some embodiments, the heteroaryl group is selected from the group consisting of furanyl, thienyl, thiazolyl, isothiazolyl, thiadiazolyl, pyrrolyl, oxazolyl, isoxazolyl, pyrazolyl, imidazolyl, pyridinyl, pyrazinyl, pyrimidinyl, pyridazinyl, quinolyl, isoquinolyl, quinoxalinyl, quinazolinyl, benzofuranyl, benzothienyl, benzimidazolyl, benzoxazolyl, benzoisoxazolyl, benzothiazolyl, indolyl.

In some embodiments, the heterocyclic group is selected from the group consisting of piperidinyl, dioxanyl, oxathianyl, morpholinyl, and piperazinyl.

In some embodiments, the cyclic group is selected from the group consisting of cyclopropyl, cyclobutyl, cyclopentyl, and cyclohexyl.

In some embodiments, ring A and ring B are each independently selected from the group consisting of the following heteroaryl or aryl groups: furanyl, thienyl, thiazolyl, isothiazolyl, thiadiazolyl, pyrrolyl, oxazolyl, isoxazolyl, pyrazolyl, imidazolyl, phenyl, pyridinyl, pyrazinyl, pyrimidinyl, pyridazinyl.

In some embodiments, the definitions of ring A and ring B satisfy one or more of the followings:

ring A is selected from the group consisting of the following heteroaryl or aryl groups: furanyl, thienyl, pyrrolyl, oxazolyl, pyrazolyl, phenyl; and ring B is selected from the group consisting of thienyl, oxazolyl, isoxazolyl, pyrazolyl, phenyl, pyridinyl, pyrazinyl, pyrimidinyl, and pyridazinyl.

In some embodiments, ring A and/or ring B are further substituted with $R_6$, $R_6$ is selected from the group consisting of hydroxyl, halogen, $C_1$-$C_6$ alkyl, $C_1$-$C_6$ alkoxycarbonyl, $C_1$-$C_6$ alkylaminocarbonyl, or $R_6$ forms an oxo 5-membered or 6-membered N-heterocycle with the ring on which it is located through a covalent bond, and the N-heterocycle is optionally substituted with $R_5$.

In some embodiments, the compound represented by formula (I) or the pharmaceutically acceptable salt thereof is selected from the group consisting of the following compounds (1) to (79), or the pharmaceutically acceptable salts thereof:
(1) N-(4-acetamidophenyl)-4-nitrobenzamide;
(2) N-(4-acetylphenyl)-5-nitrofuran-2-carboxamide;
(3) N-(4-acetamidophenyl)-5-nitrofuran-2-carboxamide;
(4) N-(4-acetamidophenyl)furan-2-carboxamide;
(5) N-phenyl-5-nitrofuran-2-carboxamide;
(6) N-(4-acetamidophenyl)thiophene-2-carboxamide;
(7) N-(4-acetamidophenyl)-1H-pyrrole-2-carboxamide;
(8) N-(4-acetamidophenyl)oxazole-5-carboxamide;
(9) N-(4-acetamidophenyl)-5-nitrothiophene-2-carboxamide;
(10) N-(pyridin-2-yl)-5-nitrofuran-2-carboxamide;
(11) N-(pyridin-3-yl)-5-nitrofuran-2-carboxamide;
(12) N-(pyridin-4-yl)-5-nitrofuran-2-carboxamide;
(13) N-(pyrazin-2-yl)-5-nitrofuran-2-carboxamide;
(14) N-(pyrimidin-2-yl)-5-nitrofuran-2-carboxamide;
(15) N-(pyridazin-3-yl)-5-nitrofuran-2-carboxamide;
(16) N-(quinolin-6-yl)-5-nitrofuran-2-carboxamide;
(17) N-(thiophen-3-yl)-5-nitrofuran-2-carboxamide;
(18) N-(thiophen-2-yl)-5-nitrofuran-2-carboxamide;
(19) N-(isoxazol-3-yl)-5-nitrofuran-2-carboxamide;
(20) N-(1H-pyrazol-5-yl)-5-nitrofuran-2-carboxamide;
(21) N-(1-methyl-1H-pyrazol-3-yl)-5-nitrofuran-2-carboxamide;
(22) N-(1-methyl-1H-pyrazol-4-yl)-5-nitrofuran-2-carboxamide;
(23) N-(4-acetamidophenyl)-5-bromofuran-2-carboxamide;
(24) N-(4-acetamidophenyl)-5-acetamidofuran-2-carboxamide;
(25) N-(4-acetamidophenyl)-5-methylsulfonylfuran-2-carboxamide;
(26) N-(2-acetamidophenyl)-5-nitrofuran-2-carboxamide;
(27) N-(3-acetamidophenyl)-5-nitrofuran-2-carboxamide;
(28) N-(3-methylphenyl)-5-nitrofuran-2-carboxamide;
(29) N-(2-methoxyphenyl)-5-nitrofuran-2-carboxamide;
(30) N-(3-methoxyphenyl)-5-nitrofuran-2-carboxamide;
(31) N-(4-methoxyphenyl)-5-nitrofuran-2-carboxamide;
(32) N-(3-hydroxyphenyl)-5-nitrofuran-2-carboxamide;
(33) N-(4-hydroxyphenyl)-5-nitrofuran-2-carboxamide;
(34) N-(3-aminophenyl)-5-nitrofuran-2-carboxamide;
(35) N-(2-fluorophenyl)-5-nitrofuran-2-carboxamide;
(36) N-(3-fluorophenyl)-5-nitrofuran-2-carboxamide;
(37) N-(4-fluorophenyl)-5-nitrofuran-2-carboxamide;
(38) N-(3-chlorophenyl)-5-nitrofuran-2-carboxamide;
(39) N-(4-chlorophenyl)-5-nitrofuran-2-carboxamide;
(40) N-(3-cyanophenyl)-5-nitrofuran-2-carboxamide;
(41) N-(4-cyanophenyl)-5-nitrofuran-2-carboxamide;
(42) ethyl 3-(5-nitrofuran-2-carboxamido)benzoate;
(43) ethyl 4-(5-nitrofuran-2-carboxamido)benzoate;
(44) N-(3-carbamoylphenyl)-5-nitrofuran-2-carboxamide;
(45) N-(4-carbamoylphenyl)-5-nitrofuran-2-carboxamide;
(46) N-(3-acetylphenyl)-5-nitrofuran-2-carboxamide;
(47) N-(4-dimethylaminophenyl)-5-nitrofuran-2-carboxamide;
(48) N-(4-morpholinylphenyl)-5-nitrofuran-2-carboxamide;

(49) N-(4-(4-ethylpiperazin-1-yl)phenyl)-5-nitrofuran-2-carboxamide;
(50) N-(4-(2-hydroxyethyl)phenyl)-5-nitrofuran-2-carboxamide;
(51) N-(4-aminomethylphenyl)-5-nitrofuran-2-carboxamide;
(52) N,N'-(1,4-phenylene)bis(5-nitrofuran-2-carboxamide);
(53) N-(3-(methylcarbamoyl)phenyl)-5-nitrofuran-2-carboxamide;
(54) N-(3-(dimethylcarbamoyl)phenyl)-5-nitrofuran-2-carboxamide;
(55) N-(3-(ethylcarbamoyl)phenyl)-5-nitrofuran-2-carboxamide;
(56) N-(3-(isopropylcarbamoyl)phenyl)-5-nitrofuran-2-carboxamide;
(57) N-(3-(isobutylcarbamoyl)phenyl)-5-nitrofuran-2-carboxamide;
(58) N-(3-(cyclohexylcarbamoyl)phenyl)-5-nitrofuran-2-carboxamide;
(59) N-(3-(benzylcarbamoyl)phenyl)-5-nitrofuran-2-carboxamide;
(60) N-(3-((2-dimethylaminoethyl)carbamoyl)phenyl)-5-nitrofuran-2-carboxamide;
(61) N-(3-((2-morpholinylethyl)carbamoyl)phenyl)-5-nitrofuran-2-carboxamide;
(62) N-(3-((3-morpholinylpropyl)carbamoyl)phenyl)-5-nitrofuran-2-carboxamide;
(63) N-(4-methyl-3-methylcarbamoylphenyl)-5-nitrofuran-2-carboxamide;
(64) N-(5-methyl-3-methylcarbamoylphenyl)-5-nitrofuran-2-carboxamide;
(65) N-(4-fluoro-3-methylcarbamoylphenyl)-5-nitrofuran-2-carboxamide;
(66) N-(5-fluoro-3-methylcarbamoylphenyl)-5-nitrofuran-2-carboxamide;
(67) N-(4-hydroxy-3-methylcarbomoylphenyl)-5-nitrofuran-2-carboxamide;
(68) $N^1,N^3$-dimethyl-5-(5-nitrofuran-2-carboxamido)isophthalamide;
(69) N-(2-methyl-1,3-dihydro-1,3-dioxo-2H-isoindol-5-yl)-5-nitrofuran-2-carboxamide;
(70) N-(4-acetamidophenyl)-5-acetylfuran-2-carboxamide;
(71) N-(4-(2-dimethylamino)acetamidophenyl)-5-nitrofuran-2-carboxamide;
(72) N-(4-(2-morpholinyl)acetamidophenyl)-5-nitrofuran-2-carboxamide;
(73) N-(4-(3-dimethylamino)propionamidophenyl)-5-nitrofuran-2-carboxamide;
(74) N-(4-((2-dimethylamino)ethylamino)acetamidophenyl)-5-nitrofuran-2-carboxamide;
(75) ethyl 2-acetamido-5-(5-nitrofuran-2-carboxamide)benzoate;
(76) ethyl 5-(5-nitrofuran-2-carboxamide)-1H-pyrazole-4-carboxylate;
(77) ethyl 5-(5-nitrofuran-2-carboxamide)-1H-pyrazole-3-carboxylate;
(78) 3-(5-acetyl-2-furoyl)carbamamide; and
(79) N-3-(ethynylphenyl)-5-nitrofuran-2-carboxamide.

In some embodiments, the drug is one for treating or preventing diseases related to the urea transporter inhibitor; preferably, the drug is a diuretic or antihypertensive drug and/or a tool drug for researching urea transporter; preferably, the urea transporter is UT-B protein or UT-A protein.

In some embodiments, the diseases related to the urea transporter inhibitor of the present invention are edema diseases related to the urea transporter inhibitor; wherein, the edema diseases preferably include: cardiogenic edema, preferably the cardiogenic edema is a cardiogenic edema due to congestive heart failure and/or constrictive pericarditis; nephrogenic edema, preferably the nephrogenic edema is a nephrogenic edema due to acute glomerulonephritis, chronic glomerulonephritis, nephrotic syndrome, renal arteriosclerosis and/or renal tubule diseases; hepatogenic edema, preferably the hepatogenic edema is a hepatogenic edema due to liver cirrhosis, liver necrosis, liver cancer and/or acute hepatitis; dystrophic edema, preferably the dystrophic edema is a dystrophic edema due to primary inadequate food intake, secondary malnutrition, digestion and absorption disorders and/or impaired protein synthesis; edema due to connective tissue diseases; allergic edema; endocrine edema; idiopathic edema; venous obstructive edema; lymphatic obstructive edema; inflammatory edema; angioneurotic edema; cerebral edema; laryngeal edema; pulmonary edema and/or lower extremity edema.

In some embodiments, the diseases related to the urea transporter inhibitor of the present invention are non-edematous diseases related to the urea transporter inhibitor; wherein, the non-edematous diseases preferably include: heart failure, preferably congestive heart failure, acute heart failure, chronic heart failure; cardiovascular and cerebrovascular diseases, preferably mild hypertension, moderate hypertension, senile systolic hypertension, hypertension with heart failure.

In some embodiments, the present invention also describes a method for treating or preventing diseases related to a urea transporter inhibitor, comprising administering a therapeutically effective amount of the compound represented by formula (I) according to the present invention, or the pharmaceutically acceptable salt thereof to a patient in need thereof.

In some embodiments, the present invention also describes the compound represented by formula (I) according to the present invention, or the pharmaceutically acceptable salt thereof for use in treating diseases related to a urea transporter inhibitor.

In some embodiments, the present invention also describes the compound represented by formula (I) according to the present invention, or the pharmaceutically acceptable salt thereof for use as a urea transporter inhibitor.

In some embodiments, the present invention also describes use of the compound represented by formula (I) according to the present invention, or the pharmaceutically acceptable salt thereof in the treatment of diseases related to a urea transporter inhibitor.

In other embodiments, the present invention describes a diarylamide compound, or a pharmaceutically acceptable salt thereof, selected from the group consisting of the following compounds, or the pharmaceutically acceptable salts thereof:

(15) N-(pyridazin-3-yl)-5-nitrofuran-2-carboxamide;
(17) N-(thiophen-3-yl)-5-nitrofuran-2-carboxamide;
(25) N-(4-acetamidophenyl)-5-methylsulfonylfuran-2-carboxamide;
(26) N-(2-acetamidophenyl)-5-nitrofuran-2-carboxamide;
(51) N-(4-aminomethylphenyl)-5-nitrofuran-2-carboxamide;
(53) N-(3-(methylcarbamoyl)phenyl)-5-nitrofuran-2-carboxamide;
(55) N-(3-(ethylcarbamoyl)phenyl)-5-nitrofuran-2-carboxamide;
(56) N-(3-(isopropylcarbamoyl)phenyl)-5-nitrofuran-2-carboxamide;

(57) N-(3-(isobutylcarbamoyl)phenyl)-5-nitrofuran-2-carboxamide;
(58) N-(3-(cyclohexylcarbamoyl)phenyl)-5-nitrofuran-2-carboxamide;
(59) N-(3-(benzylcarbamoyl)phenyl)-5-nitrofuran-2-carboxamide;
(60) N-(3-((2-dimethylaminoethyl)carbamoyl)phenyl)-5-nitrofuran-2-carboxamide;
(61) N-(3-((2-morpholinylethyl)carbamoyl)phenyl)-5-nitrofuran-2-carboxamide;
(62) N-(3-((3-morpholinylpropyl)carbamoyl)phenyl)-5-nitrofuran-2-carboxamide;
(63) N-(4-methyl-3-methylcarbamoylphenyl)-5-nitrofuran-2-carboxamide;
(64) N-(5-methyl-3-methylcarbamoylphenyl)-5-nitrofuran-2-carboxamide;
(65) N-(4-fluoro-3-methylcarbamoylphenyl)-5-nitrofuran-2-carboxamide;
(66) N-(5-fluoro-3-methylcarbamoylphenyl)-5-nitrofuran-2-carboxamide;
(67) N-(4-hydroxy-3-methylcarbamoylphenyl)-5-nitrofuran-2-carboxamide;
(68) $N^1,N^3$-dimethyl-5-(5-nitrofuran-2-carboxamido) isophthalamide;
(69) N-(2-methyl-1,3-dihydro-1,3-dioxo-2H-isoindol-5-yl)-5-nitrofuran-2-carboxamide;
(70) N-(4-acetamidophenyl)-5-acetylfuran-2-carboxamide;
(71) N-(4-(2-dimethylamino)acetamidophenyl)-5-nitrofuran-2-carboxamide;
(72) N-(4-(2-morpholinyl)acetamidophenyl)-5-nitrofuran-2-carboxamide;
(73) N-(4-(3-dimethylamino)propionamidophenyl)-5-nitrofuran-2-carboxamide;
(74) N-(4-((2-dimethylamino)ethylamino)acetamidophenyl)-5-nitrofuran-2-carboxamide;
(75) ethyl 2-acetamido-5-(5-nitrofuran-2-carboxamide) benzoate;
(76) ethyl 5-(5-nitrofuran-2-carboxamide)-1H-pyrazole-4-carboxylate;
(77) ethyl 5-(5-nitrofuran-2-carboxamide)-1H-pyrazole-3-carboxylate; and
(78) 3-(5-acetyl-2-furoyl)carbamamide.

In still other embodiments, the present invention describes a pharmaceutical composition comprising: the above-mentioned diarylamide compound or the pharmaceutically acceptable salt thereof; and a pharmaceutically acceptable carrier.

The term "pharmaceutical composition" refers to a mixture comprising one or more of the compounds of the present application or salts thereof, and a pharmaceutically acceptable carrier. The purpose of the pharmaceutical composition is to facilitate the administration of the compound of the present application to an organism.

The term "pharmaceutically acceptable" refers to those compounds, materials, compositions and/or dosage forms that are, within the scope of reliable medical judgment, suitable for use in contact with human and animal tissues without excessive toxicity, irritation, allergic response or other problems or complications, commensurate with a reasonable benefit/risk ratio.

The pharmaceutically acceptable salts of the diarylamide compounds of the present invention include acid addition salts formed with inorganic or organic acids, such as nitric acid, hydrochloric acid, hydrobromic acid, sulfuric acid, perchloric acid, phosphoric acid, acetic acid, trifluoroacetic acid, propionic acid, glycolic acid, fumaric acid, lactic acid, oxalic acid, malonic acid, malic acid, maleic acid, tartaric acid, citric acid, benzoic acid, cinnamic acid, mandelic acid, methanesulfonic acid, isethionic acid and salicylic acid. The pharmaceutically acceptable salts of the diarylamide compounds of the present invention also include salts formed with inorganic or organic bases, such as hydroxide, carbonate or bicarbonate of alkali metals or alkaline earth metals, especially sodium, potassium, calcium, ammonium or magnesium, as well as acyclic or cyclic amines, preferably methylamine, ethylamine, diethylamine, triethylamine, piperidine and the like.

The pharmaceutically acceptable carrier of the present invention includes but not limited to, water, brine solution, alcohol, polyethylene glycol, polyhydroxy-ethoxylated castor oil, peanut oil, olive oil, gelatin, lactose, gypsum powder, sucrose, dextrin, magnesium carbonate, sugar, cyclodextrin, amylose, magnesium stearate, talc, gelatin, agar, pectin, gum arabic, stearic acid or low alkyl cellulose ether, silicic acid, fatty acid, fatty-acid amine, fatty-acid monoglyceride and diglyceride, pentaerythritol fatty-acid ether, polyoxyethylene, hydroxymethyl cellulose and polyvinylpyrrolidone.

In some embodiments, the pharmaceutical composition may further include one or more pharmaceutically acceptable adjuvants, wetting agents, emulsifiers, suspending agents, preservatives, osmotic pressure regulators, buffering agents, sweetening agents, flavoring agents, coloring agents or any combinations of the above.

The pharmaceutical composition of the present invention can be produced into any dosage forms, such as capsule, tablet, aerosol, solution, suspension, sugar coating agent, lozenge, syrup, emulsion, soft ointment, ointment, injection, powder, granule, paste, sustained-release agent, foaming agent. According to different routes of administration, the pharmaceutical composition of the present invention can be produced into oral administration preparations, nasal administration preparations, pulmonary administration preparations, buccal administration preparations, subcutaneous administration preparations, intradermal administration preparations, transdermal administration preparations, parenteral administration preparations, rectal administration preparations, repository administration preparations, intravenous administration preparations, intraurethral administration preparations, intramuscular administration preparations, intranasal administration preparations, ophthalmic administration preparations, epidural administration preparations or topical administration preparations.

The compound of the present invention and composition thereof can inhibit the urea transporter UT-B-mediated permeation of urea by erythrocyte membrane, and its effect is in a dose-dependent relationship; in vivo test results show that, after intragastric or subcutaneous administration, the compound of the present invention can significantly increase the urine volume of rats and mice, reduce osmotic pressure thereof, and do not cause changes in the excretion of non-urea solutes; it can reduce the concentration of urea in the renal medulla of rats and mice, but does not cause changes in the concentration of non-urea solutes, indicating that the compound of the present invention can produce urea-selective diuretic effects in the body without obvious toxicity.

In this context, unless otherwise stated, the terms "comprise, comprises and comprising" or equivalents are open-ended expressions, meaning that in addition to the listed elements, components and steps, other unspecified elements, components and steps also can be covered.

For the purpose of describing and disclosing, all patents, patent applications and other publications identified are expressly incorporated herein by reference. These publications are provided solely for their disclosure prior to the filing date of the present application. All statements as to the dates of these documents or representation as to the contents of these documents are based on the information available to the applicants and do not constitute any admission as to the correctness of the dates or contents of these documents. Moreover, in any country, any reference to these publications in the present application does not constitute an admission that these publications form part of the common knowledge in the art.

EXAMPLES

Hereafter, the present invention will be described in detail by the following examples. The skilled in the art will understand that the following examples are only used to illustrate the present invention and should not be regarded as limiting the scope of the present invention. For those which do not indicate specific technologies or conditions in the examples, it shall be carried out in accordance with the technologies or conditions described in the literature in the art or in accordance with the product specification. The reagents, compounds or instruments used without indicating the manufacturer or source are all conventional products that can be purchased or known products that can be obtained by known methods.

Example 1:
N-(4-acetamidophenyl)-4-nitrobenzamide

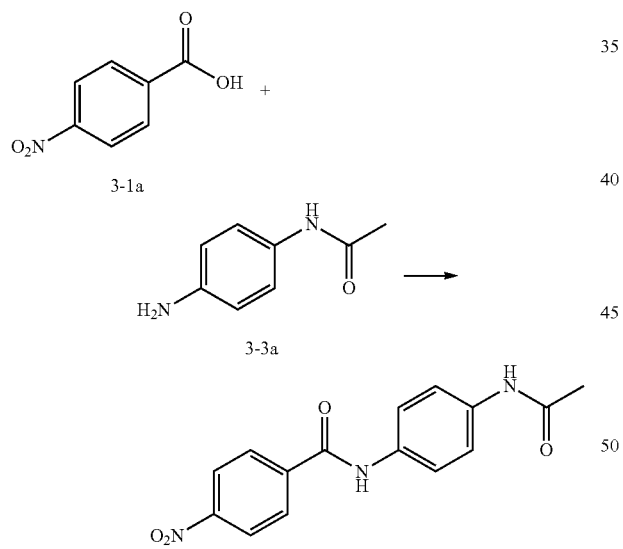

p-nitrobenzoic acid (3-1a, 167 mg, 1 mmol) was suspended in dichloromethane (5 mL), added with 2 drops of DMF, and cooled to 0° C. in an ice-water bath. Oxalyl chloride (190 mg, 0.13 mL, 1.5 mmol) was slowly added dropwise, and then stirred at room temperature for 2 h after the addition was completed. The reaction solution was concentrated to remove the solvent and excess oxalyl chloride to give p-nitrobenzoyl chloride (3-2a), added with tetrahydrofuran (1 mL) for use without purification. Acetaminoanilide (3-3a, 150 mg, 1 mmol) was dissolved in tetrahydrofuran (5 mL), added with triethylamine (152 mg, 1.5 mmol), and then added dropwise with the tetrahydrofuran solution of the above acyl chloride 3-2a under an ice bath. After the addition was completed, the reaction was carried out at room temperature until TLC ($CH_2Cl_2$:MeOH=15:1) showed that the reaction was completed. 30 mL of water was added to the reaction system, which was continued to stir for 10 min, and then filtered with suction. The filter cake was washed with 10 mL of 5% hydrochloric acid and 10 mL of distilled water successively. After drying, a yellow solid was obtained with a yield of 80% and a melting point of 301-330° C. (literature value[93] 293° C. (decomposition)).

$^1$H NMR (400 MHz, DMSO-$d_6$) δ 10.51 (s, 1H), 9.95 (s, 1H), 8.36 (d, J=8.4 Hz 2H), 8.17 (d, J=8.4 Hz, 2H), 7.69 (d, J=8.4 Hz, 2H), 7.57 (d, J=8.4 Hz, 2H), 2.04 (s, 3H). $^{13}$C NMR (101 MHz, DMSO-$d_6$) δ 168.54, 163.98, 149.54, 141.12, 134.27, 129.60, 124.00, 121.40, 119.65, 24.39.

Example 2:
N-(4-acetylphenyl)-5-nitrofuran-2-carboxamide

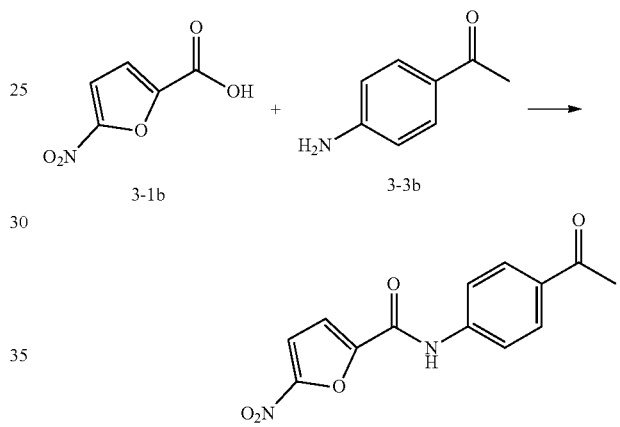

The synthesis method was the same as that in Example 1. Yellow solid, with a yield of 81%, and a melting point of 233-234° C.

$^1$H NMR (400 MHz, DMSO-$d_6$) δ 10.91 (s, 1H), 7.99 (d, J=8.0 Hz, 2H), 7.90 (d, J=8.0 Hz, 2H), 7.82 (d, J=24 Hz, 1H), 7.69 (d, J=2.4 Hz, 1H), 2.55 (s, 3H); $^{13}$C NMR (101 MHz, DMSO-$d_6$) δ 197.13, 155.33, 152.36, 147.92, 142.68, 133.14, 129.84, 120.31, 117.57, 113.90, 26.98.

Example 3:
N-(4-acetamidophenyl)-5-nitrofuran-2-carboxamide

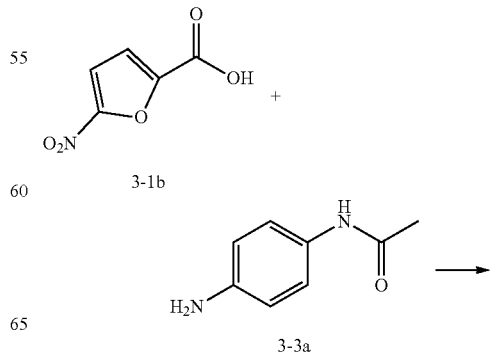

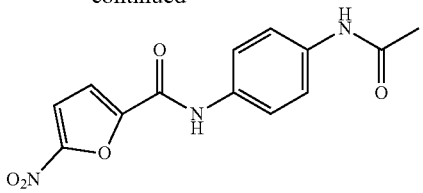

The synthesis method was the same as that in Example 1. Orange solid, with a yield of 80%, and a melting point of 233-234° C.

$^1$H NMR (400 MHz, DMSO-$d_6$) δ 10.59 (s, 1H), 9.97 (s, 1H), 7.81 (d, J=4.0 Hz, 1H), 7.62-7.66 (m, 3H), 7.57 (d, J=8.8 Hz 2H), 2.04 (s, 3H); $^{13}$C NMR (101 MHz, DMSO-$d_6$) δ 168.61, 154.79, 152.20, 148.56, 136.49, 133.32, 121.66, 119.71, 116.77, 113.97, 24.40. HRMS m/z: calcd for $C_{16}H_{13}N_3O_4$, ([M+H]$^+$): 285.08698, Found: 285.08696.

Example 4: N-(4-acetamidophenyl)furan-2-carboxamide

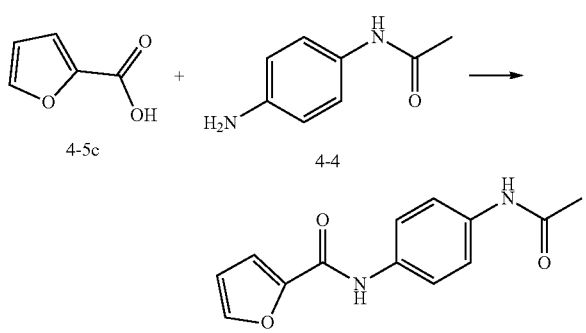

The synthesis method was the same as that in Example 1. White solid, with a yield of 68%, and a melting point of 212-214° C.

$^1$H NMR (400 MHz, DMSO-$d_6$) δ 10.11 (s, 1H), 9.91 (s, 1H), 7.92 (d, J=1.7 Hz, 1H), 7.64 (d, J=8.9 Hz, 2H), 7.53 (d, J=8.9 Hz, 2H), 7.30 (d, J=3.4 Hz, 1H), 6.69 (dd, J=3.4, 1.7 Hz, 1H), 2.03 (s, 3H). $^{13}$C NMR (101 MHz, DMSO-$d_6$) δ 168.46, 156.44, 148.06, 146.02, 135.77, 134.07, 121.28, 119.65, 114.89, 112.55, 24.37. HRMS m/z calcd for $C_{13}H_{13}N_2O_3$ [M+H]$^+$: 245.09207; found: 244.10848.

Example 5: N-phenyl-5-nitrofuran-2-carboxamide

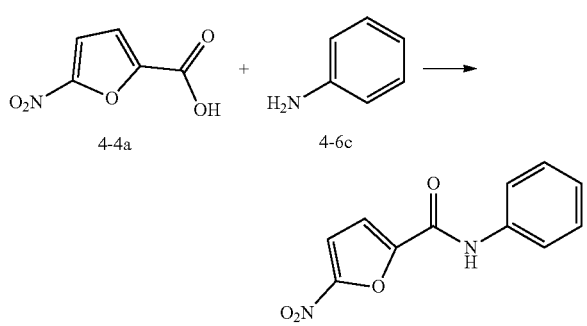

The synthesis method was the same as that in Example 1. Yellow solid, with a yield of 63%, and a melting point of 178-180° C.

$^1$H NMR (400 MHz, DMSO-$d_6$) δ 10.63 (s, 1H), 7.82 (d, J=3.9 Hz, 1H), 7.74 (d, J=7.7 Hz, 2H), 7.64 (d, J=3.9 Hz, 1H), 7.39 (t, J=7.9 Hz, 2H), 7.17 (t, J=7.4 Hz, 1H). $^{13}$C NMR (101 MHz, DMSO-$d_6$) δ 165.05, 152.22, 148.39, 138.26, 129.29, 125.04, 121.17, 116.98, 113.93. HRMS m/z calcd for $C_{11}H_9N_2O_4$ [M+H]$^+$: 233.05568; found: 233.05517.

Example 5A: N-methyl-5-nitrofuran-2-carboxamide

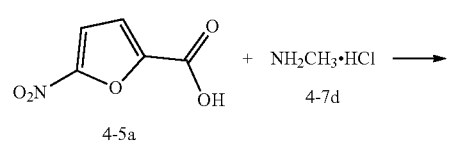

4-5a (141 mg, 1 mmol) was suspended in dichloromethane (5 mL), added with EDCI (230 mg, 1.2 mmol), HOBT (148 mg, 1.1 mmol), and stirred at room temperature for 30 min. Then 4-7d (74 mg, 1.1 mmol), triethylamine (253 mg, 2.5 mmol) were added, and the mixture was stirred at room temperature overnight. The solvent was removed by rotary evaporation, and 2N hydrochloric acid (5 mL) was added to the residue. After vigorous stirring, a solid precipitated out, which was filtered with suction. The solid was washed with water and dried to obtain 100 mg of a light yellow powder with a yield of 59% and a melting point of 187-190° C.

Example 6: N-(4-acetamidophenyl)thiophene-2-carboxamide

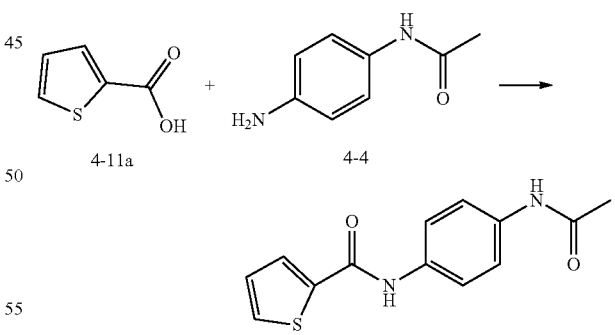

The synthesis method was the same as that in Example 1. White solid, with a yield of 55%, and a melting point of 247-248° C.

$^1$H NMR (400 MHz, DMSO-$d_6$) δ 10.17 (s, 1H), 9.91 (s, 1H), 7.99 (d, J=3.5 Hz, 1H), 7.84 (d, J=4.9 Hz, 1H), 7.62 (d, J=8.8 Hz, 2H), 7.54 (d, J=8.8 Hz, 2H), 7.22 (t, J=4.3 Hz, 1H), 2.03 (s, 3H). $^{13}$C NMR (101 MHz, DMSO-$d_6$) δ 168.57, 160.16, 140.71, 135.88, 134.34, 132.20, 129.40, 128.59, 121.43, 119.76, 24.47. HRMS m/z calcd for $C_{13}H_{13}N_2O_2S$ [M+H]$^+$: 261.06992; found: 261.06953.

Example 7: N-(4-acetamidophenyl)-1H-pyrrole-2-carboxamide

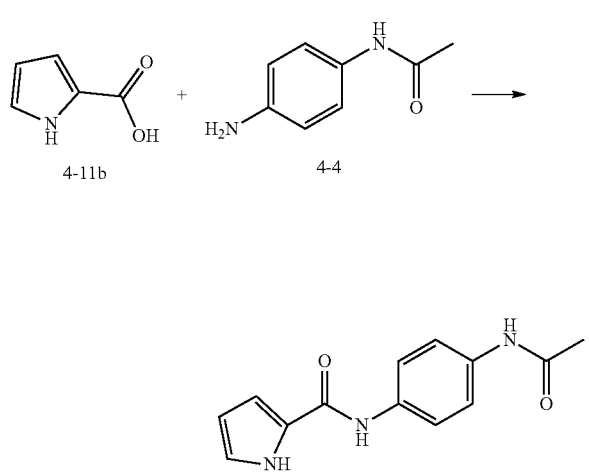

The synthesis method was the same as that in Example 5A. White solid, with a yield of 56%, and a melting point of 260-262° C.

$^1$H NMR (400 MHz, DMSO-$d_6$) δ 11.61 (s, 1H), 9.87 (s, 1H), 9.68 (s, 1H), 7.62 (d, J=8.8 Hz, 2H), 7.51 (d, J=8.8 Hz, 2H), 7.03 (s, 1H), 6.94 (s, 1H), 6.15 (d, J=2.9 Hz, 1H), 2.03 (s, 3H). $^{13}$C NMR (101 MHz, DMSO-$d_6$) δ 168.37, 159.39, 135.13, 134.95, 126.56, 122.77, 120.80, 119.70, 111.50, 109.27, 24.35. HRMS m/z calcd for $C_{13}H_{14}N_3O_2$ [M+H]$^+$: 244.10805; found: 244.10848.

Example 8: N-(4-acetamidophenyl)oxazole-5-carboxamide

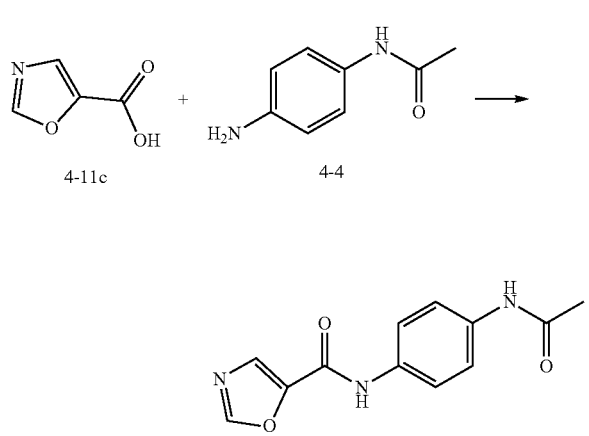

The synthesis method was the same as that in Example 1. White solid, with a yield of 62%, and a melting point of 255-257° C.

$^1$H NMR (400 MHz, DMSO-$d_6$) δ 10.37 (s, 1H), 9.94 (s, 1H), 8.64 (s, 1H), 7.96 (s, 1H), 7.63 (d, J=9.0 Hz, 2H), 7.56 (d, J=9.0 Hz, 2H), 2.04 (s, 3H). $^{13}$C NMR (101 MHz, DMSO-$d_6$) δ 168.55, 155.16, 154.21, 145.74, 136.17, 133.59, 130.29, 121.45, 119.71, 24.39. HRMS m/z calcd for $C_{12}H_{14}N_3O_3$ [M+H]$^+$: 246.08732; found: 246.08681.

Example 9: N-(4-acetamidophenyl)-5-nitrothiophene-2-carboxamide

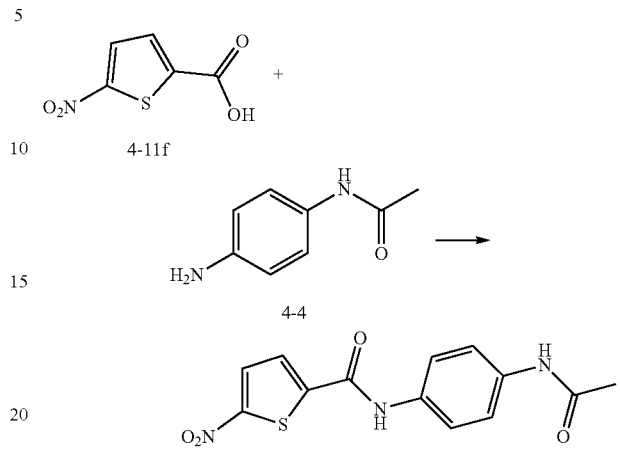

The synthesis method was the same as that in Example 1. Yellow solid, with a yield of 56%, and a melting point of 296° C. (decomposition).

$^1$H NMR (400 MHz, DMSO-$d_6$) δ 10.61 (s, 1H), 9.97 (s, 1H), 8.21 (d, J=4.4 Hz, 1H), 8.04 (d, J=4.4 Hz, 1H), 7.64 (d, J=9.0 Hz, 2H), 7.58 (d, J=9.0 Hz, 2H), 2.04 (s, 3H). $^{13}$C NMR (101 MHz, DMSO-$d_6$) δ 168.61, 158.37, 153.67, 147.07, 136.54, 133.38, 130.62, 128.57, 121.61, 119.71, 24.40. HRMS m/z calcd for $C_{13}H_{12}N_3O_4S$ [M+H]$^+$: 306.05430; found: 306.05418.

Example 10: N-(pyridin-2-yl)-5-nitrofuran-2-carboxamide

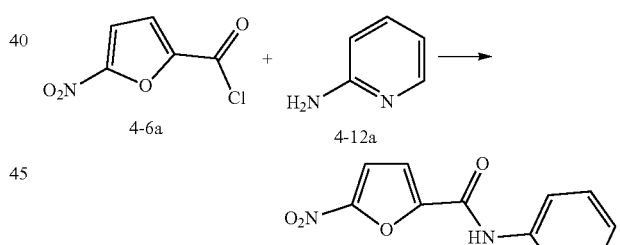

4-6a (263 mg, 1.5 mmol) was dissolved in dichloroethane (1 mL), and added dropwise to a solution of 4-12a (141 mg, 1.5 mmol) in dichloroethane (4 mL) under ice-water bath cooling. After the addition was completed, the temperature was raised to 65° C. and the mixture was stirred for 3 h. TLC (CH$_2$Cl$_2$:MeOH=15:1) showed that the reaction was almost completed. After the reaction solution was cooled to room temperature, 15 mL of water and 15 mL of ethyl acetate were added, mixed thoroughly and separated into layers. The aqueous phase was extracted with ethyl acetate (15 mL×2). After the organic phases were combined, they were successively extracted and washed with saturated NaHCO$_3$ solution, 10% citric acid, and saturated NaCl solution, dried over anhydrous sodium sulfate, and concentrated. The residue was separated by silica gel column chromatography (PE: EA=5:1), to give 160 mg of a yellow solid with a yield of 46% and a melting point of 189-190° C.

¹H NMR (400 MHz, CDCl₃) δ 8.94 (s, 1H), 8.38 (d, J=4.6 Hz, 1H), 8.29 (d, J=8.4 Hz, 1H), 7.79 (t, J=7.8 Hz, 1H), 7.42 (s, 2H), 7.15 (t, J=6.0 Hz, 1H). ¹³C NMR (101 MHz, CDCl₃) δ 154.15, 150.10, 148.30, 147.23, 138.64, 120.90, 117.22, 114.49, 112.42. HRMS m/z: calcd for C₁₀H₈N₃O₄ [M+H]⁺: 234.05093; found: 234.05065.

Example 11: N-(pyridin-3-yl)-5-nitrofuran-2-carboxamide

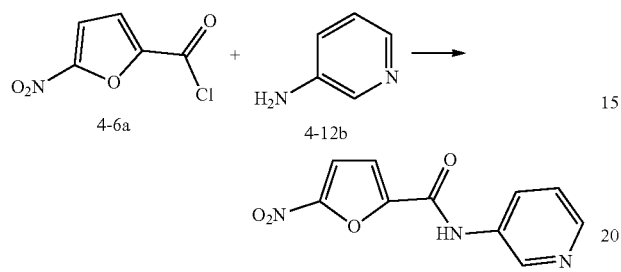

The synthesis method was the same as that in Example 10. The yield was 63%, and the melting point was 205-208° C.

¹H NMR (400 MHz, DMSO-d₆) δ 10.87 (s, 1H), 8.91 (s, 1H), 8.37 (d, J=3.8 Hz, 1H), 8.15 (d, J=8.2 Hz, 1H), 7.84 (d, J=3.2 Hz, 1H), 7.66 (d, J=3.2 Hz, 1H), 7.44 (dd, J=8.2, 3.8 Hz, 1H). ¹³C NMR (101 MHz, DMSO-d₆) δ 155.45, 152.30, 147.89, 145.88, 142.69, 135.04, 128.33, 124.16, 117.50, 113.93. HRMS m/z calcd for C₁₀H₈N₃O₄ [M+H]⁺: 234.05093; found: 234.05086.

Example 12: N-(pyridin-4-yl)-5-nitrofuran-2-carboxamide

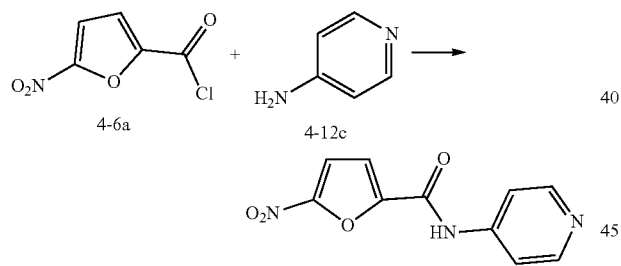

The synthesis method was the same as that in Example 10. The yield was 45%, and the melting point was 230-232° C.

¹H NMR (400 MHz, DMSO-d₆) δ 10.94 (s, 1H), 8.52 (d, J=5.2 Hz, 2H), 7.83 (d, J=3.2 Hz, 1H), 7.75 (d, J=5.2 Hz, 2H), 7.70 (d, J=3.2 Hz, 1H). ¹³C NMR (101 MHz, DMSO-d₆) δ 155.78, 152.42, 150.96, 147.54, 145.26, 117.91, 114.72, 113.84. HRMS m/z calcd for C₁₀H₈N₃O₄ [M+H]⁺: 234.05093; found: 234.05038.

Example 13: N-(pyrazin-2-yl)-5-nitrofuran-2-carboxamide

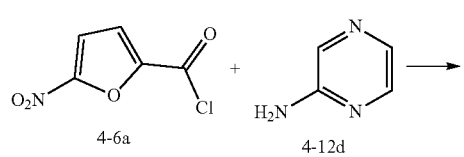

-continued

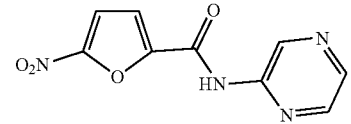

The synthesis method was the same as that in Example 10. The yield was 36%, and the melting point was 211-212° C.

¹H NMR (400 MHz, DMSO-d₆) δ 11.60 (s, 1H), 9.38 (s, 1H), 8.53 (s, 1H), 8.48 (d, J=2.4 Hz, 1H), 7.91 (d, J=4.0 Hz, 1H), 7.83 (d, J=4.0 Hz, 1H). ¹³C NMR (101 MHz, DMSO-d₆) δ 155.59, 152.72, 148.63, 147.10, 143.27, 137.86, 118.16, 113.70. HRMS m/z calcd for C₉H₇N₄O₄ [M+H]⁺: 235.04618; found: 235.04610.

Example 14: N-(pyrimidin-2-yl)-5-nitrofuran-2-carboxamide

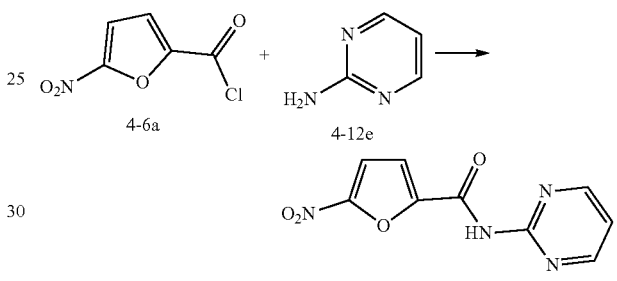

The synthesis method was the same as that in Example 10. The yield was 22%, and the melting point was 207-208° C.

¹H NMR (400 MHz, DMSO-d₆) δ 11.43 (s, 1H), 8.93-8.63 (m, 2H), 7.82 (d, J=2.0 Hz, 2H), 7.32 (t, J=4.8 Hz, 1H). ¹³C NMR (101 MHz, DMSO-d₆) δ 159.11, 157.78, 154.77, 152.64, 147.71, 118.42, 117.86, 113.70. HRMS m/z calcd for C₉H₇N₄O₄ [M+H]⁺: 235.04618; found: 235.04607.

Example 15: N-(pyridazin-3-yl)-5-nitrofuran-2-carboxamide

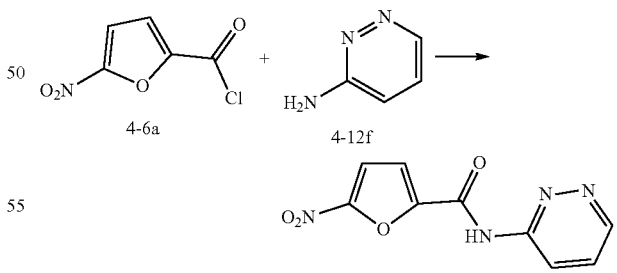

The synthesis method was the same as that in Example 10. The yield was 51%, and the melting point was 209-211° C.

¹H NMR (400 MHz, DMSO-d₆) δ 11.91 (s, 1H), 9.07 (d, J=4.2 Hz, 1H), 8.36 (d, J=9.0 Hz, 1H), 7.95 (d, J=3.2 Hz, 1H), 7.84 (d, J=3.2 Hz, 1H), 7.80-7.77 (m, 1H). ¹³C NMR (101 MHz, DMSO-d₆) δ 156.19, 155.61, 152.67, 149.67, 147.13, 129.17, 120.06, 118.10, 113.65. HRMS m/z calcd for C₉H₇N₄O₄ [M+H]⁺: 235.04618; found: 235.04607.

Example 16:
N-(quinolin-6-yl)-5-nitrofuran-2-carboxamide

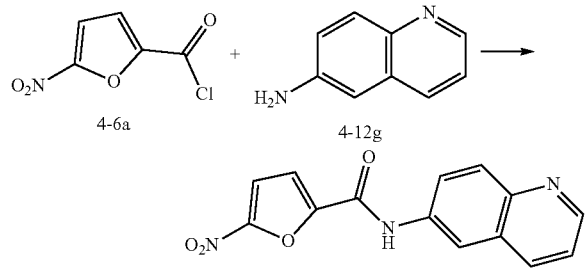

The synthesis method was the same as that in Example 1. The product was recrystallized with methanol, to give a yellow crystal with a yield of 42% and a melting point of 193-195° C.

$^1$H NMR (400 MHz, DMSO-$d_6$) δ 10.96 (s, 1H), 8.85 (dd, J=4.0, 1.2 Hz, 1H), 8.47 (s, 1H), 8.37 (d, J=8.4 Hz, 1H), 8.05 (s, 2H), 7.86 (d, J=4.0 Hz, 1H), 7.72 (d, J=4.0 Hz, 1H), 7.53 (q, J=4.0 Hz, 1H). $^{13}$C NMR (101 MHz, DMSO-$d_6$) δ 155.38, 152.34, 150.19, 148.18, 145.61, 136.28, 130.06, 128.55, 124.60, 122.41, 117.61, 117.32, 113.96. HRMS m/z: calcd for $C_{14}H_{10}N_3O_4$ [M+H]$^+$: 284.06658; found: 284.06597.

Example 17:
N-(thiophen-3-yl)-5-nitrofuran-2-carboxamide

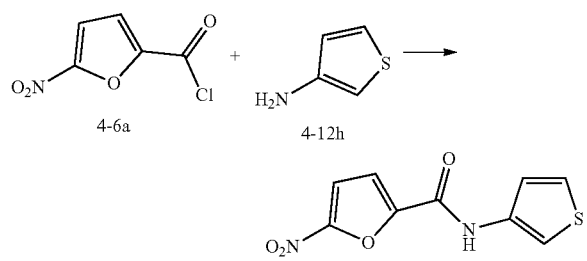

The synthesis method was the same as that in Example 1. Yellow solid, with a yield of 65%, and a melting point of 214-215° C.

$^1$H NMR (400 MHz, DMSO-$d_6$) δ 11.11 (s, 1H), 7.81 (s, 1H), 7.74 (s, 1H), 7.58 (d, J=2.8 Hz, 1H), 7.53 (t, J=2.4 Hz, 1H), 7.34 (d, J=5.0 Hz, 1H). $^{13}$C NMR (101 MHz, DMSO-$d_6$) δ 154.21, 152.21, 148.31, 136.07, 125.57, 122.41, 116.88, 114.03, 111.54. HRMS m/z calcd for $C_9H_7N_2O_4S$ [M+H]$^+$: 239.01210; found: 239.01212.

Example 18:
N-(thiophen-2-yl)-5-nitrofuran-2-carboxamide

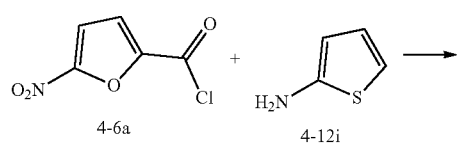

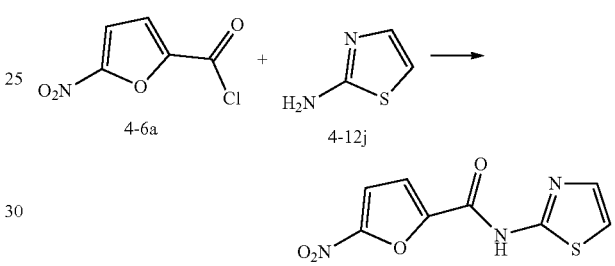

The synthesis method was the same as that in Example 1. Yellow solid, with a yield of 57%, and a melting point of 212-214° C.

$^1$H NMR (400 MHz, DMSO-$d_6$) δ 12.01 (s, 1H), 7.82 (d, J=4.0 Hz, 1H), 7.60 (d, J=4.0 Hz, 1H), 7.10 (d, J=5.4 Hz, 1H), 7.02 (d, J=3.1 Hz, 1H), 6.94 (dd, J=5.4 Hz, 4.0 Hz, 1H). $^{13}$C NMR (101 MHz, DMSO-$d_6$) δ 153.14, 152.33, 147.58, 139.05, 124.88, 119.04, 117.31, 114.08, 114.04. HRMS m/z calcd for $C_9H_7N_2O_4S$ [M+H]$^+$: 239.01210; found: 239.01156.

Example 18A:
N-(thiazol-2-yl)-5-nitrofuran-2-carboxamide

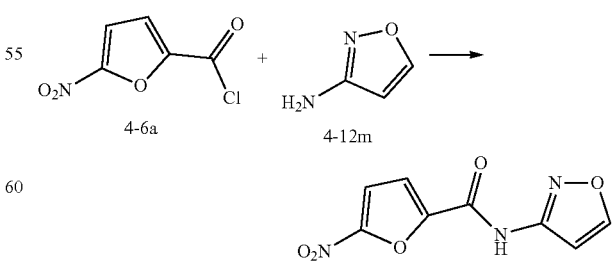

4-12j (100 mg, 1 mmol) was dissolved in dichloromethane (5 mL), and added with triethylamine (151 mg, 1.5 mmol). 4-6a (175 mg, 1 mmol) was dissolved in dichloromethane (1 mL) and added dropwise to the above solution under an ice bath. After the addition was completed, the temperature was raised to room temperature and the mixture was reacted overnight. TLC ($CH_2Cl_2$:MeOH=15:1) showed that the reaction was completed. The solvent was removed by rotary evaporation, and water (5 mL) was added to the residue, which was stirred vigorously for 30 min, and filtered with suction. The solid was washed with a small amount of methanol and dried to give 180 mg of a brown solid with a yield of 75% and a melting point of 265-268° C.

Example 19:
N-(isoxazol-3-yl)-5-nitrofuran-2-carboxamide

The synthesis method was the same as that in Example 18A. Light brown solid, with a yield of 58%, and a melting point of 230-232° C.

¹H NMR (400 MHz, DMSO-d₆) δ 11.96 (s, 1H), 8.90 (s, 1H), 7.81 (q, J=4.0 Hz, 2H), 7.02 (s, 1H). ¹³C NMR (101 MHz, DMSO-d₆) δ 161.07, 157.59, 155.00, 152.63, 146.93, 118.02, 113.65, 100.10. HRMS m/z: calcd for $C_8H_6N_3O_5$ [M+H]⁺: 224.03020; found: 224.03009.

Example 20:
N-(1H-pyrazol-5-yl)-5-nitrofuran-2-carboxamide

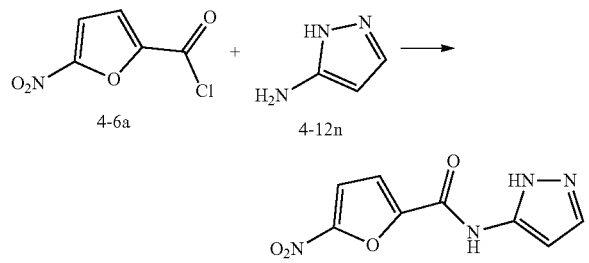

The synthesis method was the same as that in Example 18A. Orange solid, with a yield of 32%, and a melting point of 197-198° C.

¹H NMR (400 MHz, DMSO-d₆) δ 8.25 (d, J=3.0 Hz, 1H), 8.08 (d, J=3.9 Hz, 1H), 7.84 (d, J=3.9 Hz, 1H), 6.11 (d, J=3.0 Hz, 1H), 5.96 (s, 2H). ¹³C NMR (101 MHz, DMSO-d₆) δ 160.53, 153.13, 152.08, 145.52, 131.76, 124.39, 113.32, 104.04. HRMS m/z calcd for $C_8H_7N_4O_4$ [M+H]⁺: 223.04618; found: 223.04568.

Example 21: N-(1-methyl-1H-pyrazol-3-yl)-5-nitrofuran-2-carboxamide

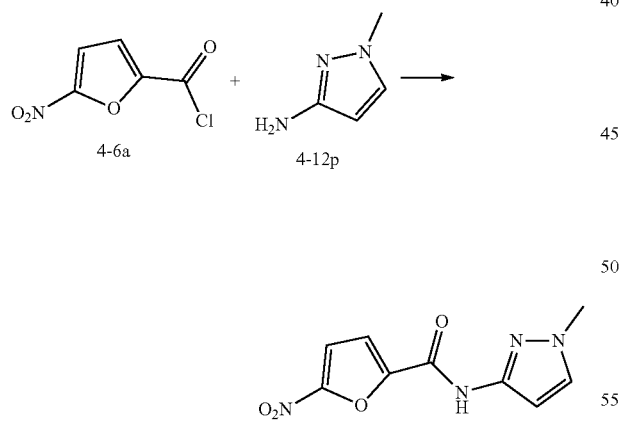

The synthesis method was the same as that in Example 1. Yellow solid, with a yield of 85%, and a melting point of 218-219° C.

¹H NMR (400 MHz, DMSO-d₆) δ 11.36 (s, 1H), 7.79 (d, J=3.8 Hz, 1H), 7.73 (d, J=3.8 Hz, 1H), 7.65 (d, J=1.8 Hz, 1H), 6.56 (d, J=1.8 Hz, 1H), 3.80 (s, 3H). ¹³C NMR (101 MHz, DMSO-d₆) δ 154.10, 152.37, 148.05, 146.24, 131.76, 116.57, 113.79, 97.94, 38.90. HRMS m/z calcd for $C_9H_9N_4O_4$ [M+H]⁺: 237.06183; found: 237.06160.

Example 22: N-(1-methyl-1H-pyrazol-4-yl)-5-nitrofuran-2-carboxamide

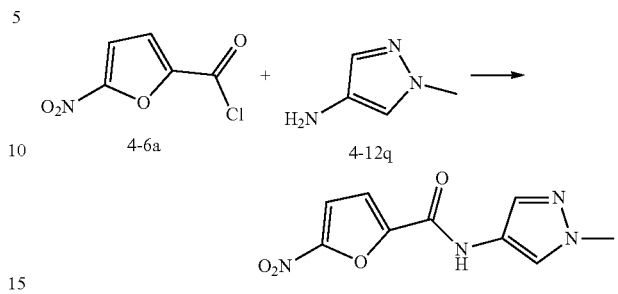

The synthesis method was the same as that in Example 1. Yellow solid, with a yield of 87%, and a melting point of 209-211° C.

¹H NMR (400 MHz, DMSO-d₆) δ 10.93 (s, 1H), 8.04 (s, 1H), 7.80 (d, J=3.8 Hz, 1H), 7.60 (s, 1H), 7.51 (d, J=3.8 Hz, 1H), 3.84 (s, 3H). ¹³C NMR (101 MHz, DMSO-d₆) δ 153.32, 152.05, 148.44, 130.81, 122.58, 120.87, 116.46, 114.09, 39.22. HRMS m/z calcd for $C_9H_9N_4O_4$ [M+H]⁺: 237.06183; found: 237.06160.

Example 23:
N-(4-acetamidophenyl)-5-bromofuran-2-carboxamide

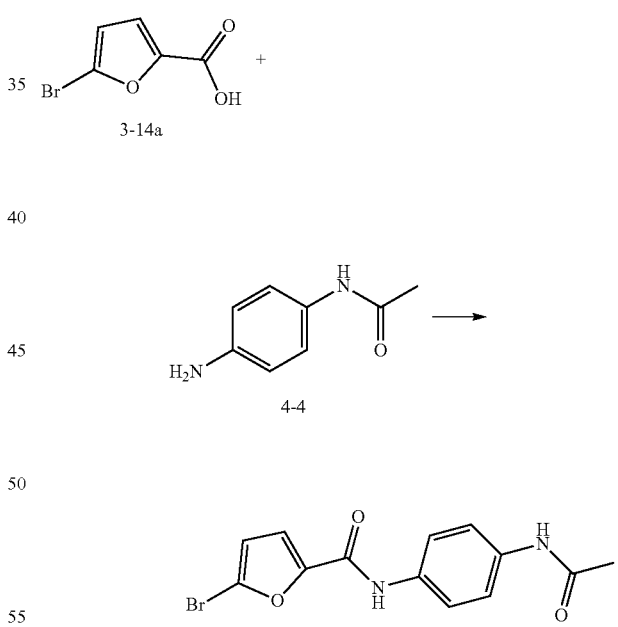

The synthesis method was the same as that in Example 1. Light yellow solid, with a yield of 85%, and a melting point of 217-219° C.

¹H NMR (400 MHz, DMSO-d₆) δ 10.15 (s, 1H), 9.92 (s, 1H), 7.62 (d, J=9.0 Hz, 2H), 7.53 (d, J=9.0 Hz, 2H), 7.34 (d, J=3.6 Hz, 1H), 6.83 (d, J=3.6 Hz, 1H), 2.03 (s, 3H). ¹³C NMR (101 MHz, DMSO-d₆) δ 168.50, 155.35, 149.84, 135.94, 133.81, 125.61, 121.39, 119.67, 117.32, 114.69, 24.38. HRMS m/z calcd for $C_{13}H_{12}BrN_2O_3$ [M+H]⁺: 323.00258; found: 323.00219.

Example 24: N-(4-acetamidophenyl)-5-acetamidofuran-2-carboxamide 5-acetamidofuran-2-carboxylic acid (4-14c)

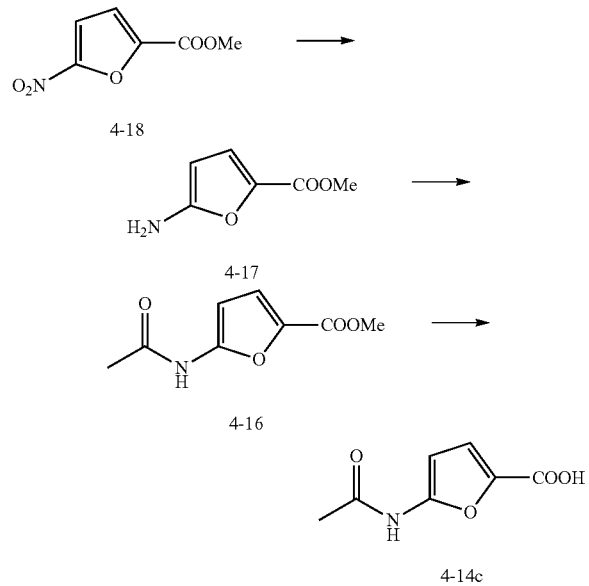

4-18 (171 mg, 1 mmol) was dissolved in methanol (10 mL), added with Pd/C (10%, 17 mg), and placed in a hydrogenator to react at room temperature for 2 h. TLC (PE:EA=3:1) showed that the reaction was completed. The reaction solution was filtered through celatom, and the filtrate was concentrated to give a yellow oil (4-17).

Acetic anhydride (2 mL) was added to 4-17, and stirred at room temperature for 1 h. The reaction solution became turbid, and TLC (PE:EA=3:1) showed that the reaction was completed. Water (10 mL) was added, and the mixture was stirred for another 15 min, and filtered with suction. The solid was washed with water to give a white solid (4-16).

Methanol (4 mL) and LiOH solution (4N, 1 mL) were added to the undried 4-16, and stirred at room temperature until the hydrolysis was completed. Water (5 mL×3) was added to the reaction solution, the organic phases were combined and dried with anhydrous $Na_2SO_4$, and concentrated to give 4-14c, 80 mg of a white solid. The total yield of the three steps was 47%.

N-(4-acetamidophenyl)-5-acetamidofuran-2-carboxamide (Example 24)

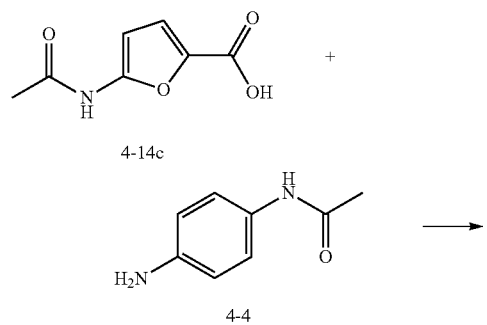

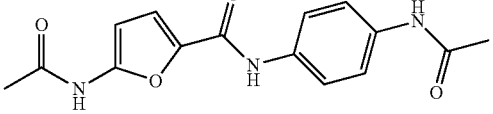

The synthesis method was the same as that in Example 1. Light yellow solid, with a yield of 85%, and a melting point of 250-251° C.

$^1$H NMR (400 MHz, DMSO-$d_6$) δ 10.37 (s, 1H), 9.95 (s, 1H), 7.64 (d, J=8.8 Hz, 2H), 7.58-7.54 (m, 3H), 7.45 (d, J=3.6 Hz, 1H), 2.53 (s, 3H), 2.04 (s, 3H). $^{13}$C NMR (101 MHz, DMSO-$d_6$) δ 187.18, 168.55, 155.92, 152.90, 150.25, 136.25, 133.57, 121.69, 119.67, 119.37, 116.04, 26.78, 24.40. HRMS m/z calcd for $C_{15}H_{15}N_2O_4$ [M+H]$^+$: 287.10263; found: 287.10235.

Example 25: N-(4-acetamidophenyl)-5-methylsulfonylfuran-2-carboxamide N-(4-acetamidophenyl)-5-methylsulfonylfuran-2-carboxamide 5-methylsulfonylfuran-2-carboxylic acid (4-14d)

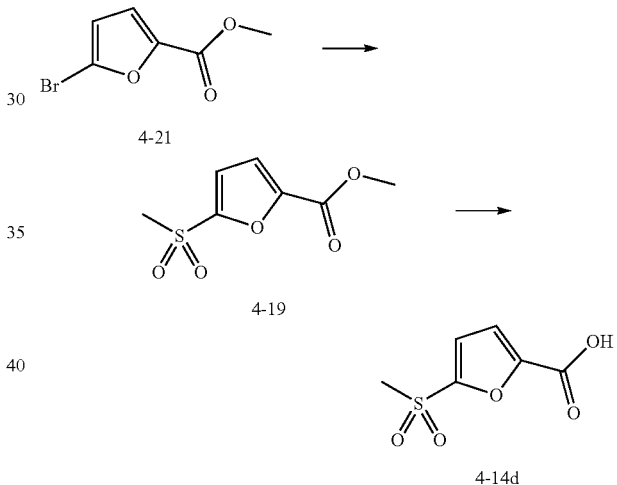

4-21 (205 mg, 1 mmol), sodium methanesulfonate (510 mg, 5 mmol), anhydrous DMSO (5 mL) were added to a reaction flask, and stirred at 110° C. for 20 h. TLC (PE:EA=4:1) showed that a small amount of raw materials remained unreacted in the reaction. The reaction solution was cooled to room temperature, added with ethyl acetate (20 mL), washed with saturated NaCl solution (15 mL×3), dried over anhydrous $Na_2SO_4$ and concentrated. The product was separated by silica gel column chromatography (PE:EA=4:1) to give 4-19, 72 mg of a light yellow solid, with a yield of 35%.

$^1$H NMR (400 MHz, CDCl$_3$) δ 10.37 (s, 1H), 9.95 (s, 1H), 7.64 (d, J=8.8 Hz, 2H), 7.58-7.54 (m, 3H), 7.45 (d, J=3.6 Hz, 1H), 2.53 (s, 3H), 2.04 (s, 3H). $^{13}$C NMR (101 MHz, CDCl$_3$) δ 157.89, 151.99, 147.77, 117.82, 117.70, 52.68, 43.07.

Tetrahydrofuran (4 mL) and LiOH aqueous solution (3N, 1 mL) were added to 4-19 (72 mg, 0.35 mmol), stirred at room temperature for 5 min, and TLC (PE:EA=2:1) showed that the reaction was completed. Most of the solvent was removed by rotary evaporation, and the residue was added with water (5 mL), adjusted with 4N hydrochloric acid to pH=3, and extracted with ethyl acetate (5 mL×3). The organic phases were combined and washed with saturated NaCl, dried over anhydrous $Na_2SO_4$, and concentrated to give 4-14d, 63 mg of a white solid, with a yield of 95%.

N-(4-acetamidophenyl)-5-methylsulfonylfuran-2-carboxamide (Example 25)

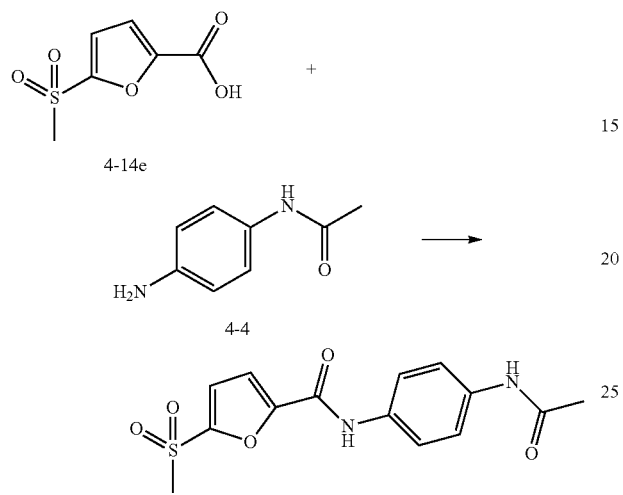

The synthesis method was the same as that in Example 5A. Off-white solid, with a yield of 37%, and a melting point of 251-253° C.

$^1$H NMR (400 MHz, DMSO-d$_6$) δ 10.40 (s, 1H), 9.96 (s, 1H), 7.62 (d, J=8.8 Hz, 2H), 7.57 (d, J=8.8 Hz, 2H), 7.48 (d, J=3.6 Hz, 1H), 7.44 (d, J=3.6 Hz, 1H), 3.43 (s, 3H), 2.04 (s, 3H). $^{13}$C NMR (101 MHz, DMSO-d$_6$) δ 168.58, 155.31, 151.01, 150.91, 136.39, 133.32, 121.76, 119.70, 118.23, 115.31, 43.28, 24.40. HRMS m/z calcd for $C_{14}H_{15}N_2O_5S$ [M+H]$^+$: 323.06962; found: 323.06897.

Example 26:
N-(2-acetamidophenyl)-5-nitrofuran-2-carboxamide

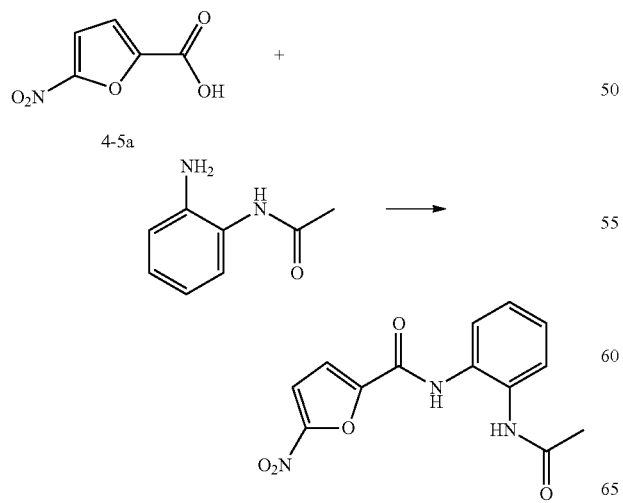

The synthesis method was the same as that in Example 1. Yellow crystal, with a yield of 64%, and a melting point of 212-213° C.

$^1$H NMR (400 MHz, DMSO-d$_6$) δ 10.16 (s, 1H), 9.73 (s, 1H), 7.83 (d, J=3.7 Hz, 1H), 7.60-7.56 (m, 3H), 7.27-7.20 (m, 2H), 2.10 (s, 3H). $^{13}$C NMR (101 MHz, DMSO-d$_6$) δ 169.66, 155.28, 152.01, 148.57, 132.47, 129.03, 126.66, 125.28, 124.85, 116.89, 114.01, 23.99. HRMS m/z: calcd for $C_{13}H_{12}N_3O_5$ [M+H]$^+$: 290.07715; found: 290.07695.

Example 27:
N-(3-acetamidophenyl)-5-nitrofuran-2-carboxamide

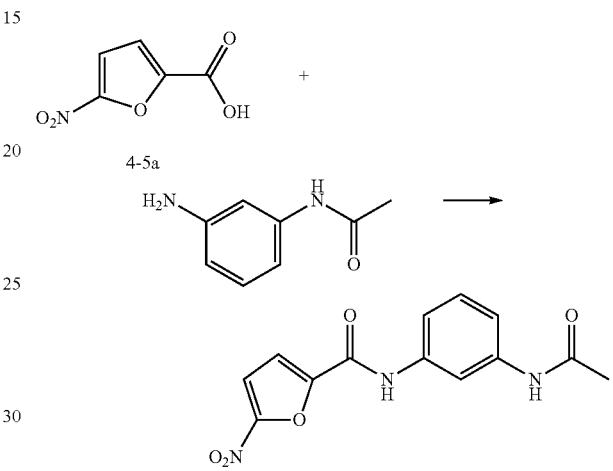

The synthesis method was the same as that in Example 1. Yellow solid, with a yield of 77%, and a melting point of 212-214° C.

$^1$H NMR (400 MHz, DMSO-d$_6$) δ 10.63 (s, 1H), 10.03 (s, 1H), 8.09 (s, 1H), 7.82 (d, J=3.9 Hz, 1H), 7.67 (d, J=3.9 Hz, 1H), 7.44 (d, J=7.8 Hz, 1H), 7.35-7.27 (m, 2H), 2.06 (s, 3H). $^{13}$C NMR (101 MHz, DMSO-d$_6$) δ 168.87, 155.05, 152.27, 148.41, 140.15, 138.57, 129.39, 116.95, 115.93, 115.76, 113.89, 111.87, 24.52. HRMS m/z calcd for $C_{13}H_{12}N_3O_5$ [M+H]$^+$: 290.07715; found: 290.07690.

Example 28:
N-(3-methylphenyl)-5-nitrofuran-2-carboxamide

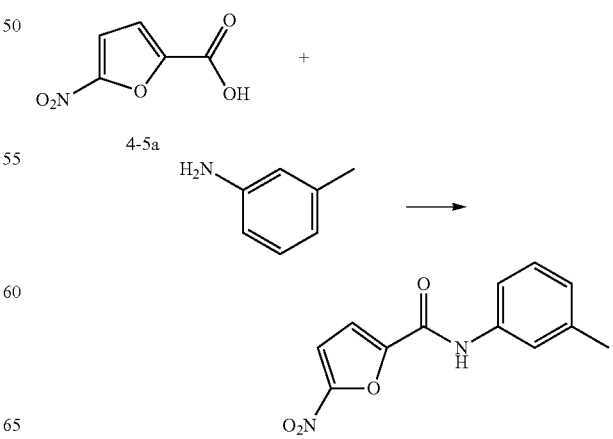

The synthesis method was the same as that in Example 1. The product was separated by silica gel column (PE:EA=6:1), to give a yellow solid with a yield of 62% and a melting point of 144-145° C.

$^1$H NMR (400 MHz, CDCl$_3$) δ 8.15 (s, 1H), 7.50-7.46 (m, 2H), 7.41 (d, J=3.8 Hz, 1H), 7.37 (d, J=3.8 Hz, 1H), 7.29 (d, J=7.6 Hz, 1H), 7.03 (d, J=7.6 Hz, 1H), 2.38 (s, 3H). $^{13}$C NMR (101 MHz, CDCl$_3$) δ 153.89, 147.94, 139.31, 136.24, 129.10, 126.40, 120.99, 117.49, 116.70, 112.68, 21.48. HRMS m/z calcd for C$_{12}$H$_{11}$N$_2$O$_4$ [M+H]$^+$: 247.07133; found: 247.07116.

Example 29:
N-(2-methoxyphenyl)-5-nitrofuran-2-carboxamide

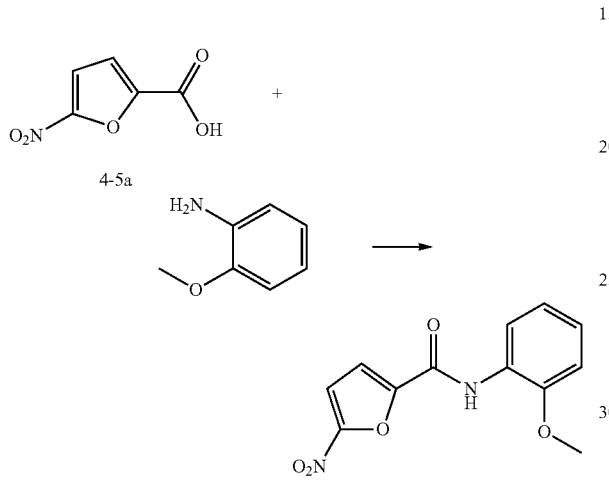

The synthesis method was the same as that in Example 1. Yellow solid, with a yield of 72%, and a melting point of 142-144° C.

$^1$H NMR (400 MHz, CDCl$_3$) δ 8.86 (s, 1H), 8.41 (d, J=8.0 Hz, 1H), 7.41 (d, J=3.7 Hz, 1H), 7.35 (d, J=3.7 Hz, 1H), 7.15 (t, J=7.8 Hz, 1H), 7.02 (t, J=7.8 Hz, 1H), 6.96 (d, J=8.0 Hz, 1H), 3.98 (s, 3H). $^{13}$C NMR (101 MHz, CDCl$_3$) δ 153.70, 148.39, 148.21, 126.24, 125.14, 121.14, 120.26, 116.39, 112.57, 110.18, 55.95. HRMS m/z calcd for C$_{12}$H$_{11}$N$_2$O$_5$ [M+H]$^+$: 263.06625; found: 263.06540.

Example 30:
N-(3-methoxyphenyl)-5-nitrofuran-2-carboxamide

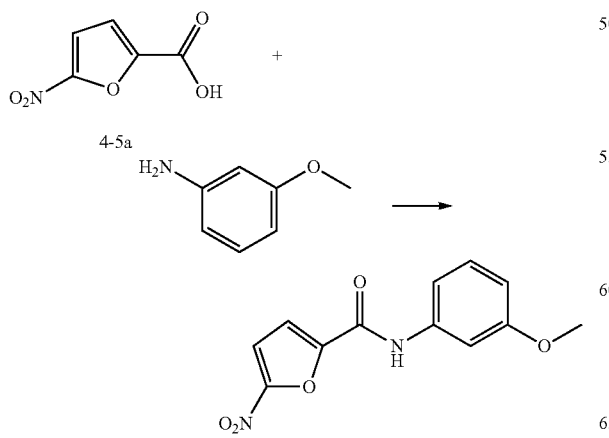

The synthesis method was the same as that in Example 1. Yellow solid, with a yield of 91%, and a melting point of 123-124° C.

$^1$H NMR (400 MHz, CDCl$_3$) δ 8.25 (s, 1H), 7.42-7.37 (m, 3H), 7.29 (t, J=8.0 Hz, 1H), 7.17 (d, J=7.2 Hz, 1H), 6.76 (dd, J=8.0, 1.8 Hz, 1H), 3.84 (s, 3H). $^{13}$C NMR (101 MHz, CDCl$_3$) δ 160.27, 153.94, 147.83, 137.53, 129.98, 116.80, 112.70, 112.53, 111.45, 106.09, 55.40. HRMS m/z calcd for C$_{12}$H$_{11}$N$_2$O$_5$ [M+H]$^+$: 263.06625; found: 263.06565.

Example 31:
N-(4-methoxyphenyl)-5-nitrofuran-2-carboxamide

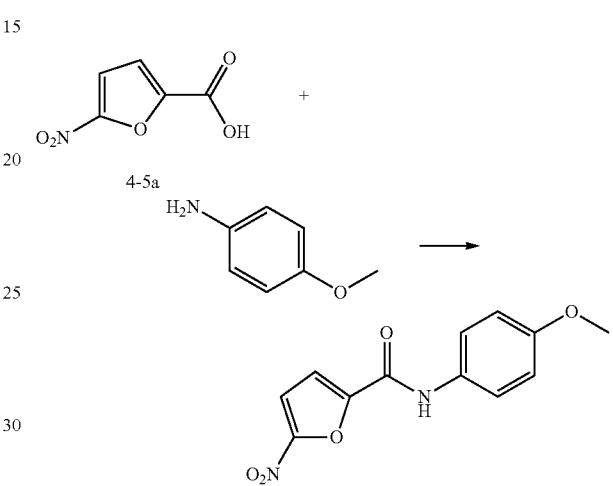

The synthesis method was the same as that in Example 1. Yellow solid, with a yield of 72%, and a melting point of 185-187° C.

$^1$H NMR (400 MHz, DMSO-d$_6$) δ 10.53 (s, 1H), 7.82 (d, J=3.8 Hz, 1H), 7.65 (d, J=8.8 Hz, 2H), 7.61 (d, J=3.8 Hz, 1H), 6.96 (d, J=8.8 Hz, 2H), 3.76 (s, 3H). $^{13}$C NMR (101 MHz, DMSO-d$_6$) δ 156.61, 154.71, 152.14, 148.85, 131.21, 122.78, 116.63, 114.40, 113.98, 55.67. HRMS m/z calcd for C$_{12}$H$_{11}$N$_2$O$_5$ [M+H]$^+$: 263.06625; found: 263.06567.

Example 32:
N-(3-hydroxyphenyl)-5-nitrofuran-2-carboxamide

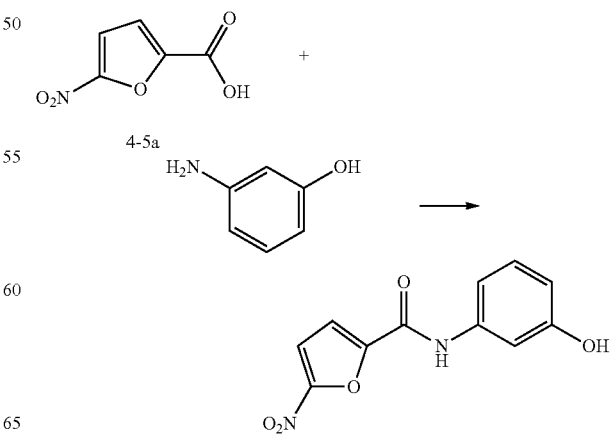

The synthesis method was the same as that in Example 5A. The product was recrystallized with ethanol, to give a yellow solid with a yield of 89% and a melting point of 226-228° C.

$^1$H NMR (400 MHz, DMSO-$d_6$) δ 10.47 (s, 1H), 9.52 (s, 1H), 7.81 (d, J=3.9 Hz, 1H), 7.64 (d, J=3.9 Hz, 1H), 7.30 (d, J=2.0 Hz, 1H), 7.18-7.12 (m, 2H), 6.56 (dt, J=7.6, 2.0 Hz, 1H). $^{13}$C NMR (101 MHz, DMSO-$d_6$) δ 158.06, 154.91, 152.20, 148.47, 139.29, 129.92, 116.83, 113.88, 112.15, 111.78, 108.17. HRMS m/z calcd for $C_{11}H_9N_2O_5$ [M+H]$^+$: 249.05060; found: 249.05046.

Example 33:
N-(4-hydroxyphenyl)-5-nitrofuran-2-carboxamide

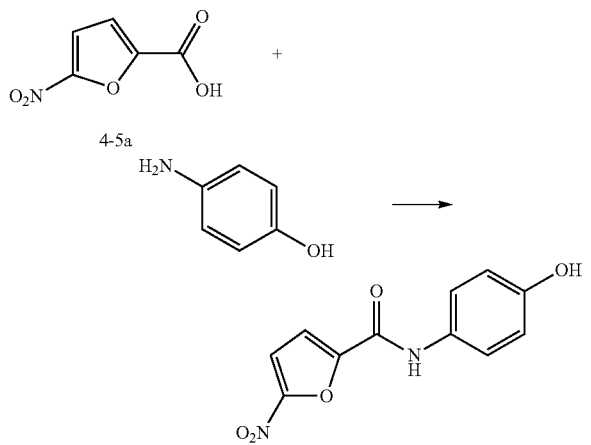

The synthesis method was the same as that in Example 5A. Yellow solid, with a yield of 86%, and a melting point of 247-249° C.

$^1$H NMR (400 MHz, DMSO-$d_6$) δ 10.42 (s, 1H), 9.39 (s, 1H), 7.80 (d, J=3.9 Hz, 1H), 7.58 (d, J=3.9 Hz, 1H), 7.50 (d, J=8.8 Hz, 2H), 6.77 (d, J=8.8 Hz, 2H). $^{13}$C NMR (101 MHz, DMSO-$d_6$) δ 154.89, 154.59, 152.10, 148.82, 129.67, 123.03, 116.42, 115.64, 113.97. HRMS m/z calcd for $C_{12}H_{11}N_2O_5$ [M+H]$^+$: 263.06625; found: 263.06567.

Example 34:
N-(3-aminophenyl)-5-nitrofuran-2-carboxamide

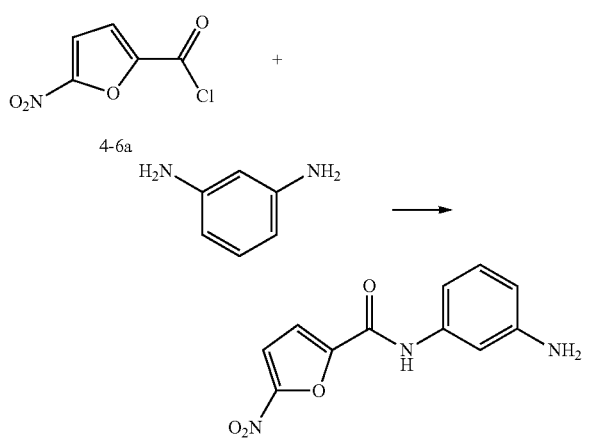

M-phenylenediamine (108 mg, 1 mmol) was dissolved in tetrahydrofuran (5 mL), added with triethylamine (151 mg, 1.5 mmol), and the mixture was cooled to 0° C. under an ice water bath. 4-6a (175 mg, 1 mmol) was dissolved in tetrahydrofuran (1 mL), added dropwise to the above solution in batches. After the addition was completed, the reaction was warmed to room temperature and reacted until TLC ($CH_2Cl_2$:MeOH=15:1) showed that the reaction was completed. 10 mL of 2N HCl solution was added to the reaction solution, and further stirred for another 10 min. The mixture was filtered with suction to remove insoluble materials, and the filtrate was adjusted to pH=9 with saturated sodium carbonate aqueous solution, extracted with ethyl acetate (8 mL×3). The organic phase was concentrated to give a yellow solid, which was washed with a small amount of water/methanol, and dried to give 100 mg of pure product. The yield was 41%, and the melting point was 191-193° C.

$^1$H NMR (400 MHz, DMSO-$d_6$) δ 10.30 (s, 1H), 7.80 (d, J=3.9 Hz, 1H), 7.62 (d, J=3.9 Hz, 1H), 7.03-6.97 (m, 2H), 6.83 (d, J=8.0 Hz, 1H), 6.36 (dd, J=8.0, 1.2 Hz, 1H), 5.17 (s, 2H). $^{13}$C NMR (101 MHz, DMSO-$d_6$) δ 5154.75, 152.17, 149.57, 148.69, 138.86, 129.47, 116.57, 113.88, 111.00, 108.85, 106.57. HRMS m/z calcd for $C_{11}H_{10}N_3O_4$ [M+H]$^+$: 248.06658; found: 248.06640.

Example 35:
N-(2-fluorophenyl)-5-nitrofuran-2-carboxamide

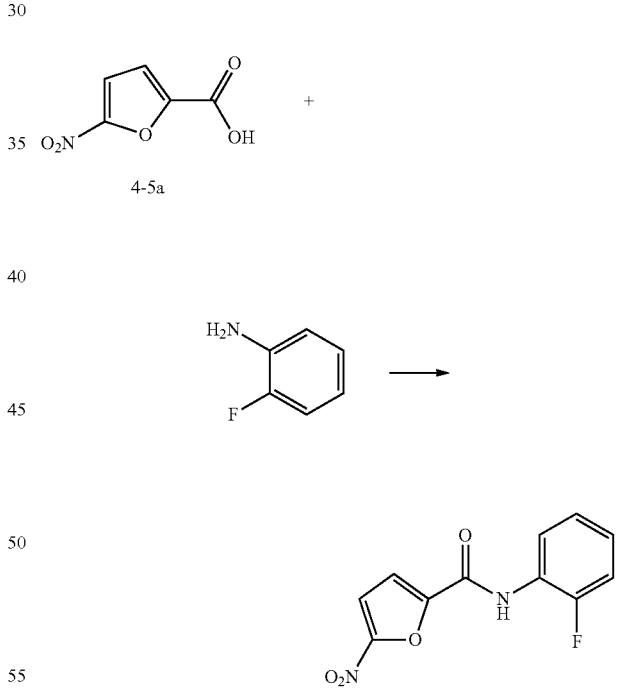

The synthesis method was the same as that in Example 1. Light yellow solid, with a yield of 92%, and a melting point of 164-165° C.

$^1$H NMR (400 MHz, DMSO-$d_6$) δ 10.57 (s, 1H), 7.82 (d, J=3.9 Hz, 1H), 7.64 (d, J=3.9 Hz, 1H), 7.58 (t, J=7.8 Hz, 1H), 7.35-7.32 (m, 2H), 7.27-7.23 (m, 1H). $^{13}$C NMR (101 MHz, DMSO-$d_6$) δ 157.46, 155.33, 154.99, 152.28, 147.88, 128.33, 128.25, 127.68, 125.01, 124.98, 124.63, 124.51, 117.35, 116.60, 116.40, 113.85. HRMS m/z calcd for $C_{11}H_8FN_2O_4$ [M+H]$^+$: 251.04626; found: 251.04616.

Example 36:
N-(3-fluorophenyl)-5-nitrofuran-2-carboxamide

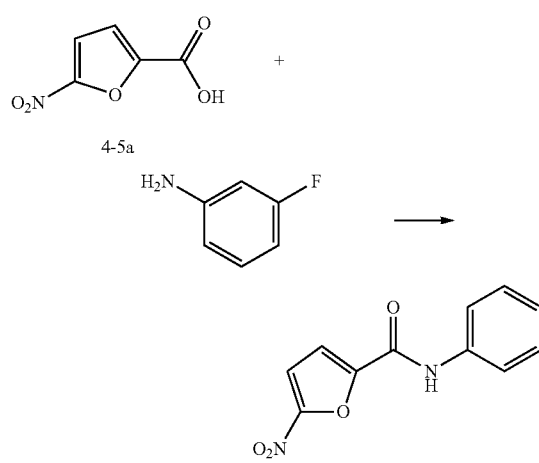

The synthesis method was the same as that in Example 1. The product was separated by silica gel column chromatography (PE:EA=5:1), to give a yellow solid with a yield of 50% and a melting point of 164-165° C.

$^1$H NMR (400 MHz, CDCl$_3$) δ 8.24 (s, 1H), 7.65 (d, J=10.6 Hz, 1H), 7.41 (dd, J=11.4, 3.8 Hz, 2H), 7.36-7.31 (m, 2H), 6.92 (t, J=8.0 Hz, 1H). $^{13}$C NMR (101 MHz, CDCl$_3$) δ 164.21, 161.76, 153.93, 147.42, 137.84, 137.73, 130.47, 130.38, 117.11, 115.64, 115.61, 112.65, 112.48, 112.27, 108.11, 107.84. HRMS m/z calcd for C$_{11}$H$_8$FN$_2$O$_4$ [M+H]$^+$: 251.04626; found: 251.04602.

Example 37:
N-(4-fluorophenyl)-5-nitrofuran-2-carboxamide

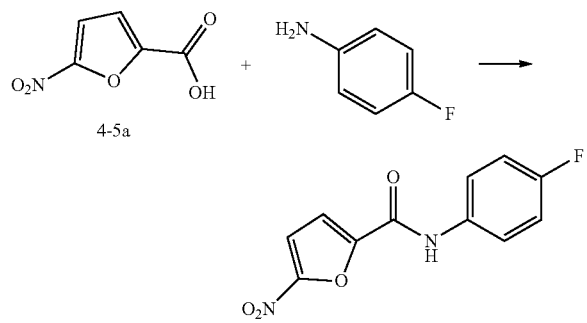

The synthesis method was the same as that in Example 1. The product was separated by silica gel column chromatography (PE:EA=5:1) to give a yellow solid with a yield of 46% and a melting point of 173-174° C.

$^1$H NMR (400 MHz, CDCl$_3$) δ 8.18 (s, 1H), 7.66-7.63 (m, 2H), 7.42 (d, J=3.8 Hz, 1H), 7.38 (d, J=3.8 Hz, 1H), 7.10 (t, J=8.6 Hz, 2H). $^{13}$C NMR (101 MHz, CDCl$_3$) δ 161.31, 158.86, 153.93, 147.65, 132.29, 122.35, 122.27, 116.87, 116.18, 115.95, 112.64. HRMS m/z calcd for C$_{11}$H$_7$FN$_2$O$_4$ [M+H]$^+$: 251.04626; found: 251.04611.

Example 38:
N-(3-chlorophenyl)-5-nitrofuran-2-carboxamide

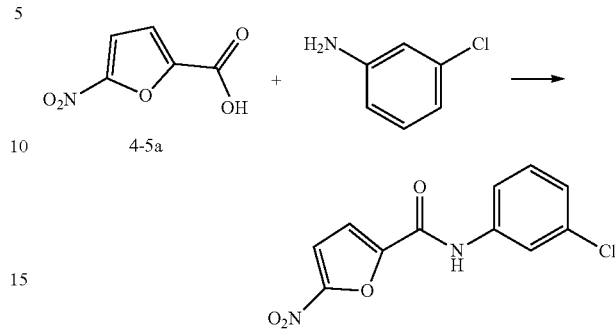

The synthesis method was the same as that in Example 1. Yellow solid, with a yield of 86%, and a melting point of 153-154° C.

$^1$H NMR (400 MHz, CDCl$_3$) δ 8.21 (s, 1H), 7.82 (t, J=1.8 Hz, 1H), 7.52 (d, J=8.0 Hz, 1H), 7.43 (d, J=4.0 Hz, 1H), 7.39 (d, J=4.0 Hz, 1H), 7.33 (t, J=8.0 Hz, 1H), 7.19 (d, J=8.0 Hz, 1H). $^{13}$C NMR (101 MHz, CDCl$_3$) δ 153.94, 147.38, 137.43, 135.00, 130.26, 125.65, 120.52, 118.33, 117.14, 112.64. HRMS m/z calcd for C$_{11}$H$_8$ClN$_2$O$_4$ [M+H]$^+$: 267.01671; found: 267.01600.

Example 39:
N-(4-chlorophenyl)-5-nitrofuran-2-carboxamide

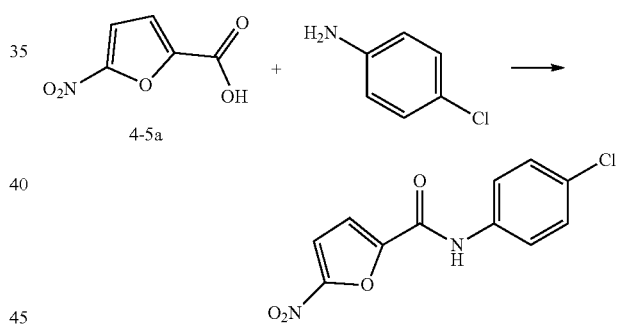

The synthesis method was the same as that in Example 1. Yellow solid, with a yield of 80%, and a melting point of 179-180° C.

$^1$H NMR (400 MHz, DMSO-d$_6$) δ 10.76 (s, 1H), 7.83 (d, J=3.7 Hz, 1H), 7.78 (d, J=8.6 Hz, 2H), 7.64 (d, J=3.7 Hz, 1H), 7.45 (d, J=8.6 Hz, 2H). $^{13}$C NMR (101 MHz, DMSO-d$_6$) δ 155.09, 152.26, 148.11, 137.26, 129.22, 128.70, 122.67, 117.24, 113.93. HRMS m/z calcd for C$_{11}$H$_7$FN$_2$O$_4$ [M+H]$^+$: 251.04626; found: 251.04611.

Example 40:
N-(3-cyanophenyl)-5-nitrofuran-2-carboxamide

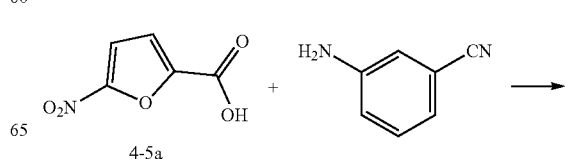

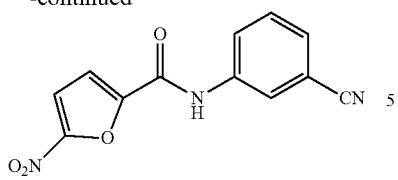

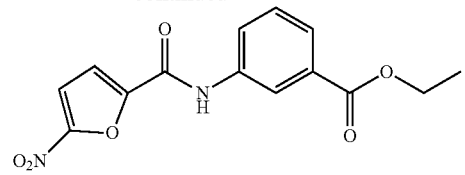

The synthesis method was the same as that in Example 1. Yellow solid, with a yield of 58%, and a melting point of 193-194° C.

$^1$H NMR (400 MHz, DMSO-d$_6$) δ 10.93 (s, 1H), 8.19 (s, 1H), 8.03 (d, J=7.2 Hz, 1H), 7.83 (d, J=4.0 Hz, 1H), 7.67-7.60 (m, 3H). $^{13}$C NMR (101 MHz, DMSO-d$_6$) δ 155.41, 152.34, 147.77, 139.14, 130.80, 128.51, 125.74, 123.96, 118.97, 117.66, 113.91, 112.11. HRMS m/z calcd for C$_{12}$H$_8$N$_3$O$_4$ [M+H]$^+$: 258.05093; found: 258.05055.

The synthesis method was the same as that in Example 1. The product was separated by silica gel column chromatography (PE:EA=4:1), to give a yellow solid with a yield of 66% and a melting point of 126-128° C.

$^1$H NMR (400 MHz, CDCl$_3$) δ 8.43 (s, 1H), 8.22 (s, 1H), 8.03 (d, J=8.0 Hz, 1H), 7.88 (d, J=8.0 Hz, 1H), 7.48 (t, J=8.0 Hz, 1H), 7.42-7.40 (m, 2H), 4.40 (q, J=6.8 Hz, 2H), 1.41 (t, J=6.8 Hz, 3H). $^{13}$C NMR (101 MHz, CDCl$_3$) δ 165.93, 154.21, 151.40, 147.61, 136.64, 131.68, 129.46, 126.59, 124.76, 121.37, 117.11, 112.72, 61.40, 14.37. HRMS m/z calcd for C$_{14}$H$_{13}$N$_2$O$_6$ [M+H]$^+$: 305.07681; found: 305.07662.

Example 41: N-(4-cyanophenyl)-5-nitrofuran-2-carboxamide

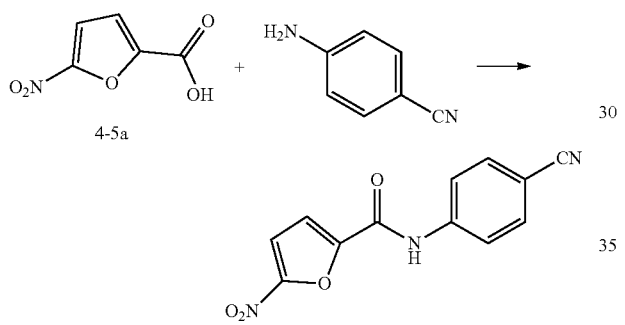

The synthesis method was the same as that in Example 1. Light yellow solid, with a yield of 65%, a melting point of 229-231° C.

$^1$H NMR (400 MHz, DMSO-d$_6$) δ 10.99 (s, 1H), 7.96 (d, J=8.8 Hz, 2H), 7.87 (d, J=8.8 Hz, 2H), 7.83 (d, J=4.0 Hz, 1H), 7.70 (d, J=4.0 Hz, 1H). $^{13}$C NMR (101 MHz, DMSO-d$_6$) δ 155.47, 152.39, 147.68, 142.64, 133.74, 121.07, 119.31, 117.84, 113.88, 106.76. HRMS m/z calcd for C$_{12}$H$_8$N$_3$O$_4$ [M+H]$^+$: 258.05093; found: 258.05055.

Example 42: Ethyl 3-(5-nitrofuran-2-carboxamido)benzoate

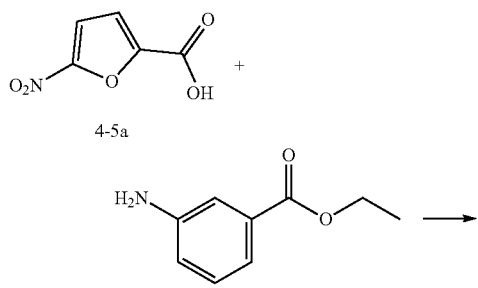

Example 43: Ethyl 4-(5-nitrofuran-2-carboxamido)benzoate

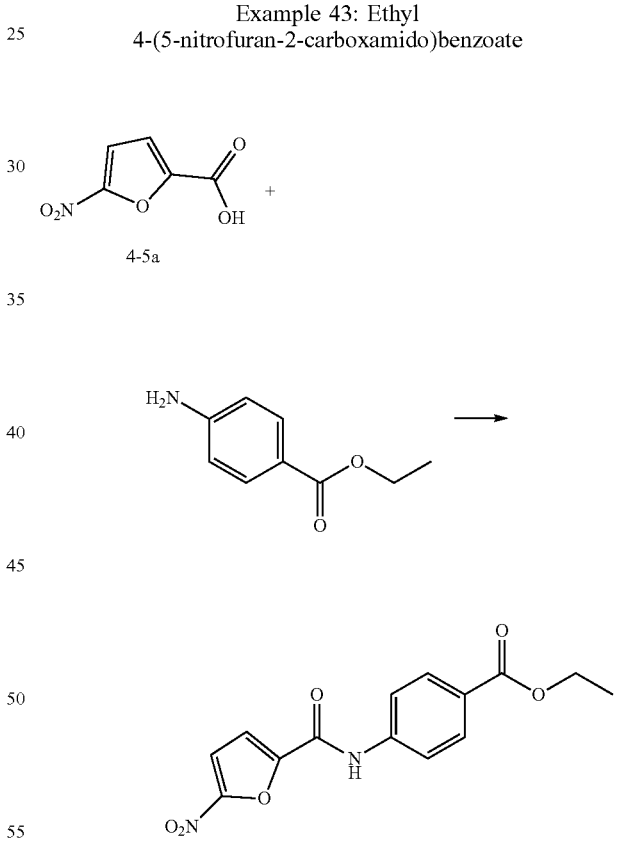

The synthesis method was the same as that in Example 1. Yellow solid, with a yield of 77%, and a melting point of 221-223° C.

$^1$H NMR (400 MHz, DMSO-d$_6$) δ 10.92 (s, 1H), 7.99 (d, J=8.8 Hz, 2H), 7.91 (d, J=8.8 Hz, 2H), 7.84 (d, J=3.9 Hz, 1H), 7.70 (d, J=3.9 Hz, 1H), 4.31 (q, J=7.2 Hz, 2H), 1.33 (t, J=7.2 Hz, 3H). $^{13}$C NMR (101 MHz, DMSO-d$_6$) δ 165.67, 155.31, 152.36, 147.89, 142.72, 130.64, 125.84, 120.41, 117.55, 113.89, 61.05, 14.66. HRMS m/z calcd for C$_{14}$H$_{13}$N$_2$O$_6$ [M+H]$^+$: 305.07681; found: 305.07648.

Example 44:
N-(3-carbamoylphenyl)-5-nitrofuran-2-carboxamide

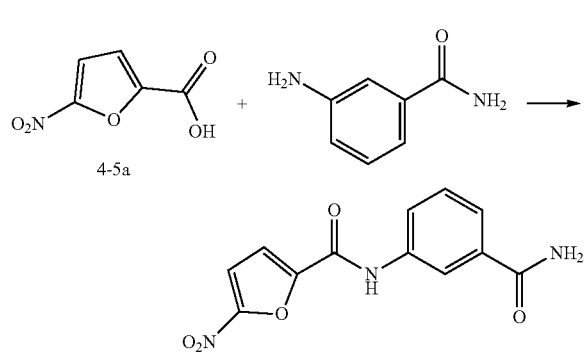

The synthesis method was the same as that in Example 1. Yellow solid, with a yield of 84%, and a melting point of 238-240° C.

$^1$H NMR (400 MHz, DMSO-$d_6$) δ 10.76 (s, 1H), 8.20 (s, 1H), 7.99-7.94 (m, 2H), 7.82 (d, J=4.0 Hz, 1H), 7.69-7.66 (m, 2H), 7.47 (t, J=8.0 Hz, 2H), 7.40 (s, 1H). $^{13}$C NMR (101 MHz, DMSO-$d_6$) δ 168.06, 155.14, 152.29, 148.21, 138.35, 135.57, 129.16, 123.80, 123.69, 120.81, 117.10, 113.91. HRMS m/z calcd for $C_{12}H_{10}N_3O_5$ [M+H]$^+$: 276.06150; found: 276.06126.

Example 45:
N-(4-carbamoylphenyl)-5-nitrofuran-2-carboxamide

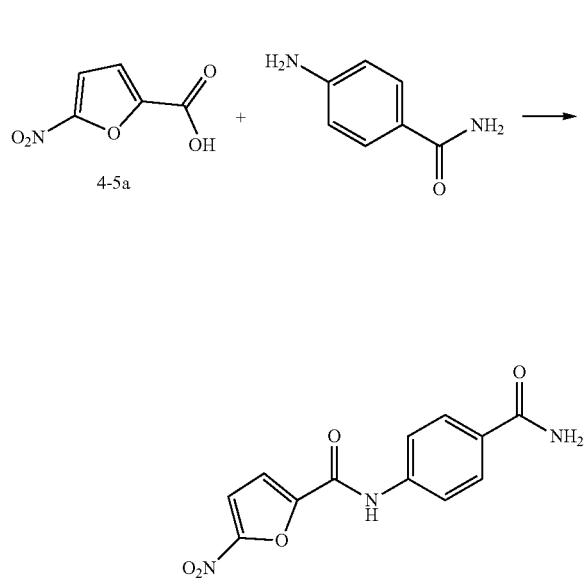

The synthesis method was the same as that in Example 1. Yellow solid, with a yield of 87%, and a melting point of 297° C. (decomposition).

$^1$H NMR (400 MHz, DMSO-$d_6$) δ 10.85 (s, 1H), 7.96-7.91 (m, 3H), 7.85-7.82 (m, 3H), 7.72-7.70 (m, 1H), 7.37 (s, 1H). $^{13}$C NMR (101 MHz, DMSO-$d_6$) δ 167.71, 155.21, 152.31, 148.93, 130.46, 128.81, 120.20, 117.37, 113.92. HRMS m/z calcd for $C_{12}H_{10}N_3O_5$ [M+H]$^+$: 276.06150; found: 276.06125.

Example 46:
N-(3-acetylphenyl)-5-nitrofuran-2-carboxamide

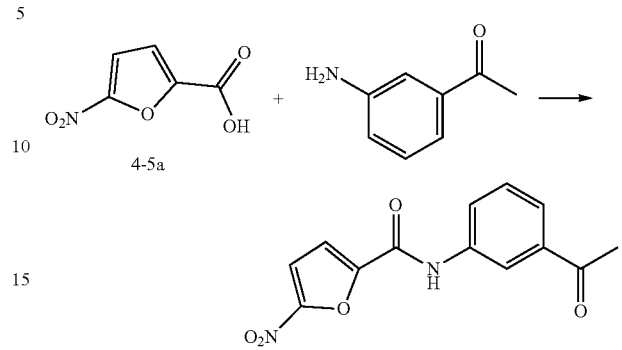

The synthesis method was the same as that in Example 1. Yellow solid, with a yield of 95%, and a melting point of 182-183° C.

$^1$H NMR (400 MHz, DMSO-$d_6$) δ 10.82 (s, 1H), 8.29 (t, J=2.0 Hz, 1H), 8.06 (dd, J=8.4, 1.2 Hz, 1H), 7.83 (d, J=3.9 Hz, 1H), 7.78 (d, J=7.8 Hz, 1H), 7.67 (d, J=3.9 Hz, 1H), 7.56 (t, J=7.8 Hz, 1H), 2.60 (s, 3H). $^{13}$C NMR (101 MHz, DMSO-$d_6$) δ 197.99, 155.26, 152.30, 148.11, 138.73, 129.77, 125.53, 125.03, 120.32, 117.26, 113.92, 27.23. HRMS m/z calcd for $C_{13}H_{11}N_2O_5$[M+H]$^+$: 275.06625; found: 275.06598.

Example 47: N-(4-dimethylaminophenyl)-5-nitrofuran-2-carboxamide

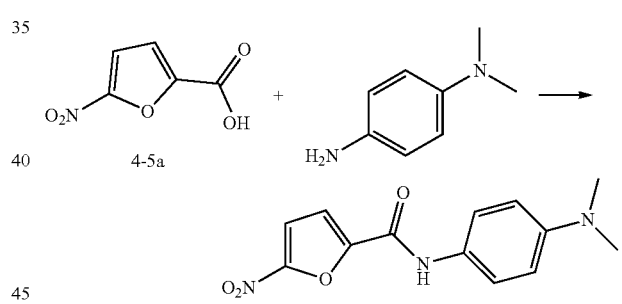

The synthesis method was the same as that in Example 1. Brown solid, with a yield of 63%, and a melting point of 202-205° C.

$^1$H NMR (400 MHz, CDCl$_3$) δ 8.09 (s, 1H), 7.52 (d, J=8.8 Hz, 2H), 7.40 (d, J=3.6 Hz, 1H), 7.34 (d, J=3.6 Hz, 1H), 6.74 (d, J=8.8 Hz, 2H), 2.96 (s, 6H). $^{13}$C NMR (101 MHz, CDCl$_3$) δ 153.58, 148.61, 148.45, 125.77, 122.02, 121.91, 116.19, 112.80, 112.73, 40.68. HRMS m/z: calcd for $C_{14}H_{10}N_3O_4$ [M+H]$^+$: 284.06658; found: 284.06597.

Example 48:
N-(4-morpholinylphenyl)-5-nitrofuran-2-carboxamide

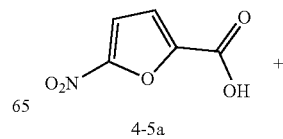

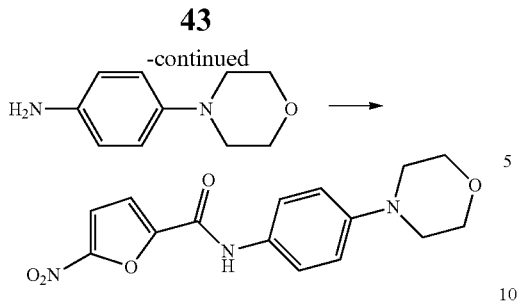

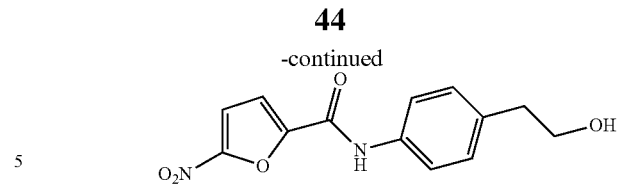

The synthesis method was the same as that in Example 1. Brown solid, with a yield of 35%, and a melting point of 208-209° C.

$^1$H NMR (400 MHz, CDCl$_3$) δ 8.11 (s, 1H), 7.58 (d, J=8.4 Hz, 2H), 7.41 (s, 1H), 7.36 (s, 1H), 6.94 (d, J=8.4 Hz, 2H), 3.87 (s, 4H), 3.17 (s, 4H). $^{13}$C NMR (101 MHz, CDCl$_3$) δ 153.69, 151.25, 149.06, 148.11, 128.70, 121.74, 116.49, 116.08, 112.81, 66.84, 49.32. HRMS m/z calcd for C$_{14}$H$_{10}$N$_3$O$_4$ [M+H]$^+$: 284.06658; found: 284.06597.

Example 49: N-(4-(4-ethylpiperazin-1-yl)phenyl)-5-nitrofuran-2-carboxamide

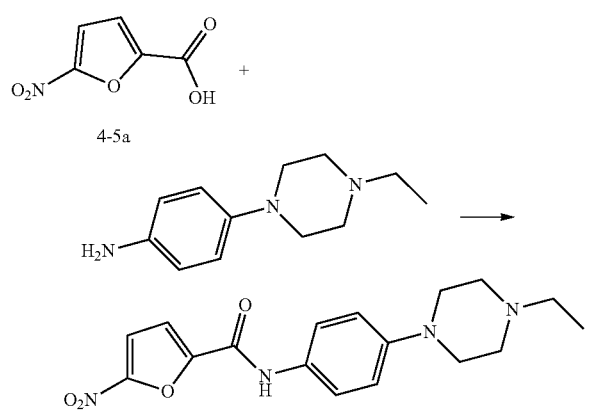

The synthesis method was the same as that in Example 1. Brown solid, with a yield of 71%, and a melting point of 185-186° C.

$^1$H NMR (400 MHz, CDCl$_3$) δ 8.10 (s, 1H), 7.55 (d, J=8.4 Hz, 2H), 7.41 (s, 1H), 7.35 (s, 1H), 6.95 (d, J=8.4 Hz, 2H), 3.23 (s, 4H), 2.62 (s, 4H), 2.49 (q, J=7.0 Hz, 2H), 1.14 (t, J=7.0 Hz, 3H). $^{13}$C NMR (101 MHz, CDCl$_3$) δ 153.73, 151.21, 149.10, 148.24, 128.38, 121.75, 116.43, 116.28, 112.86, 52.76, 52.38, 49.10, 12.05. HRMS m/z calcd for C$_{14}$H$_{10}$N$_3$O$_4$ [M+H]$^+$: 284.06658; found: 284.06597.

Example 50: N-(4-(2-hydroxyethyl)phenyl)-5-nitrofuran-2-carboxamide

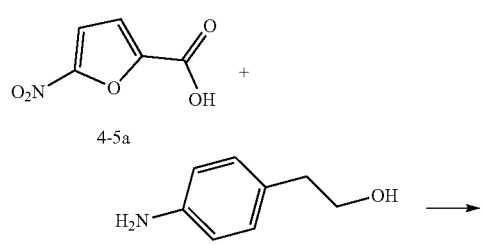

The synthesis method was the same as that in Example 1. The product was separated by silica gel column chromatography (CH$_2$Cl$_2$:MeOH=25:1) to give a yellow solid with a yield of 35% and a melting point of 147-148° C.

$^1$H NMR (400 MHz, DMSO-d$_6$) δ 10.55 (s, 1H), 7.81 (d, J=4.0 Hz, 1H), 7.64-7.62 (m, 3H), 7.23 (d, J=8.4 Hz, 2H), 4.62 (t, J=5.2 Hz, 1H), 3.60 (dd, J=12.4, 6.8 Hz, 2H), 2.71 (t, J=6.8 Hz, 2H). $^{13}$C NMR (101 MHz, DMSO-d$_6$) δ 154.90, 152.17, 148.53, 136.40, 136.13, 129.61, 121.11, 116.80, 113.93, 62.59, 38.96. HRMS m/z calcd for C$_{13}$H$_{13}$N$_2$O$_5$[M+H]$^+$: 277.08190; found: 277.08177.

Example 51: N-(4-aminomethylphenyl)-5-nitrofuran-2-carboxamide

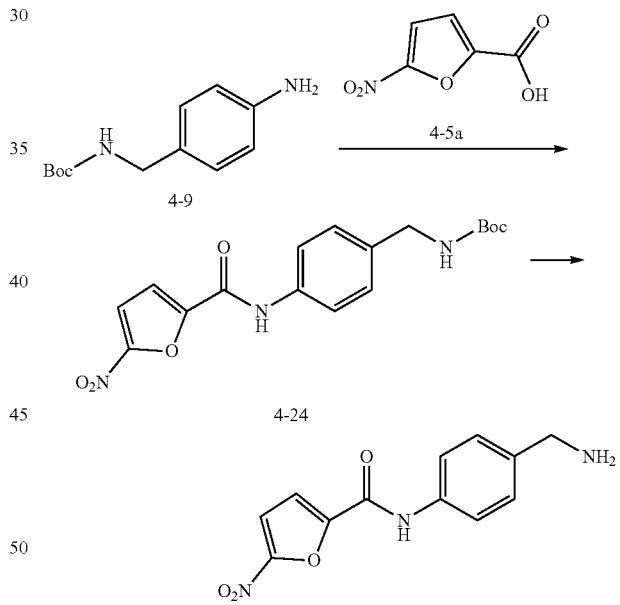

The synthesis method of 4-24 was the same as that in Example 1. 4-24 was added to 4N HCl ethyl acetate solution (2 mL), and stirred at room temperature until TLC (CH$_2$Cl$_2$: MeOH=15:1) showed that the reaction was completed. The mixture was filtered with suction to give 232 mg of a light yellow solid, which was the hydrochloride salt of Example 51. The yield was 60%, and the melting point was 249-252° C.

$^1$H NMR (400 MHz, D$_2$O) δ 7.84 (d, J=8.2 Hz, 2H), 7.59 (d, J=3.6 Hz, 1H), 7.50-7.48 (m, 3H), 4.12 (s, 2H). $^{13}$C NMR (101 MHz, D$_2$O) δ 155.49, 152.14, 147.75, 138.34, 129.55, 129.39, 121.15, 116.39, 111.98, 42.48. HRMS m/z calcd for C$_{14}$H$_{10}$N$_3$O$_4$ [M+H]$^+$: 284.06658; found: 284.06597.

Example 52: N,N'-(1,4-phenylene)bis(5-nitrofuran-2-carboxamide)

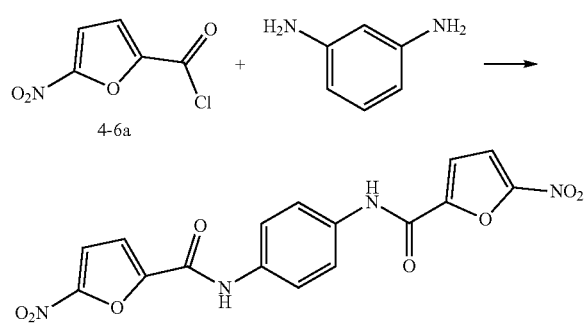

M-phenylenediamine (108 mg, 1 mmol) was dissolved in tetrahydrofuran (5 mL), added with triethylamine (302 mg, 3 mmol), and cooled under an ice-water bath. 4-6a (350 mg, 2 mmol) was dissolved in tetrahydrofuran (1 mL) and added dropwise to the above solution. After the addition was completed, the reaction was warmed to room temperature and stirred overnight. TLC (CH$_2$Cl$_2$:MeOH=15:1) showed that the reaction was completed. Water (20 mL) was added to the reaction solution, which was stirred thoroughly and filtered with suction. After drying, 232 mg of a yellow solid was obtained, with a yield of 60%, and a melting point of 185-186° C.

$^1$H NMR (400 MHz, CDCl$_3$) δ 10.73 (s, 2H), 8.26 (s, 1H), 7.82 (s, 2H), 7.68 (s, 2H), 7.54 (s, 1H), 7.52 (s, 1H), 7.40 (t, J=8.0 Hz, 1H). $^{13}$C NMR (101 MHz, CDCl$_3$) δ 155.12, 152.30, 148.30, 138.68, 129.59, 117.40, 117.10, 113.92, 113.46. HRMS m/z calcd for C$_{14}$H$_{10}$N$_3$O$_4$ [M+H]$^+$: 284.06658; found: 284.06597.

Example 53: N-(3-(methylcarbamoyl)phenyl)-5-nitrofuran-2-carboxamide 3-amino-N-methylbenzamide (4-25a)

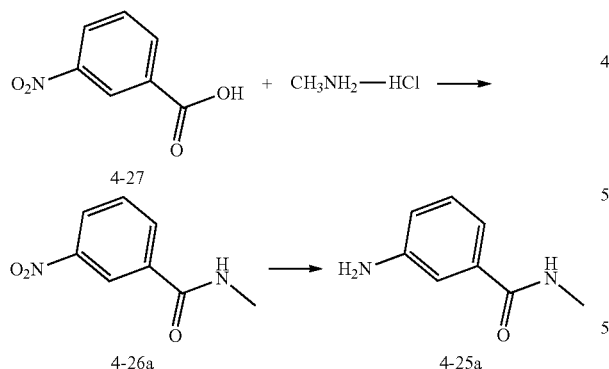

The synthesis method of 4-26a was the same as that in Example 5A. 4-26a (180 mg, 1 mmol) was dissolved in methanol (10 mL), added with Pd/C (10%, 18 mg), placed in a hydrogenator to react at room temperature for 2 h. TLC (CH$_2$Cl$_2$:MeOH=15:1) showed that the reaction was completed. The reaction solution was filtered through celatom, and the filtrate was concentrated to give 4-25a, a yellow solid, with a yield of 70%. 4-25b and 4-32a~n were synthesized in the same way.

N-(3-(methylcarbamoyl)phenyl)-5-nitrofuran-2-carboxamide (Example 53)

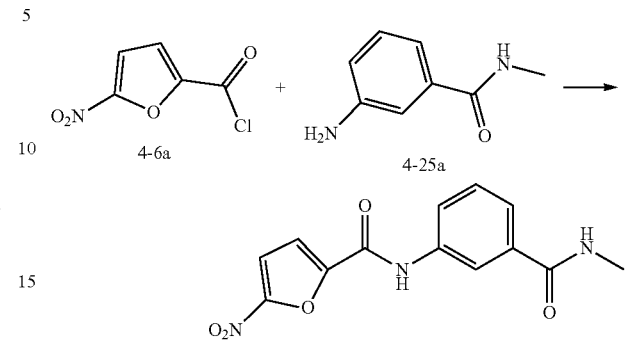

The synthesis method was the same as that in Example 1. Yellow solid, with a yield of 70%, and a melting point of 250-252° C.

$^1$H NMR (400 MHz, DMSO-d$_6$) δ 10.79 (s, 1H), 8.49 (s, 1H), 8.19 (s, 1H), 7.95 (d, J=7.8 Hz, 1H), 7.83 (s, 1H), 7.70 (s, 1H), 7.61 (d, J=7.8 Hz, 1H), 7.48 (t, J=7.8 Hz, 1H), 2.80 (d, J=2.8 Hz, 3H). $^{13}$C NMR (101 MHz, DMSO-d$_6$) δ 166.74, 155.13, 152.28, 148.16, 138.42, 135.71, 129.22, 123.51, 123.12, 120.40, 117.11, 113.90, 26.76. HRMS m/z calcd for C$_{13}$H$_{12}$N$_3$O$_5$ [M+H]$^+$: 290.07715; found: 290.07696.

Example 54: N-(3-(dimethylcarbamoyl)phenyl)-5-nitrofuran-2-carboxamide

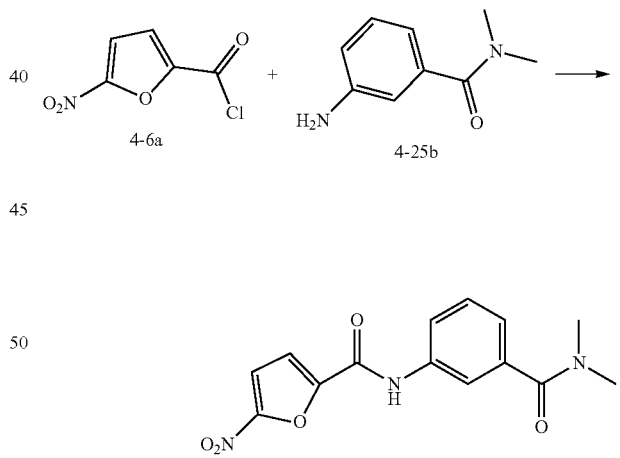

The synthesis method was the same as that in Example 1. The product was separated by silica gel column chromatography (PE:EA=1:3) to give a yellow solid, with a yield of 56% and a melting point of 157-159° C.

$^1$H NMR (400 MHz, CDCl$_3$) δ 9.45 (s, 1H), 7.77 (d, J=8.0 Hz, 1H), 7.66 (s, 1H), 7.38-7.30 (m, 3H), 7.16 (d, J=8.0 Hz, 1H), 3.12 (s, 1H), 3.00 (s, 1H). $^{13}$C NMR (101 MHz, CDCl$_3$) δ 171.19, 154.47, 151.41, 148.06, 137.06, 136.77, 129.12, 123.17, 121.73, 119.46, 116.73, 112.60, 39.57, 35.36. HRMS m/z calcd for C$_{14}$H$_{14}$N$_3$O$_5$ [M+H]$^+$: 304.09280; found: 304.09265.

Example 55: N-(3-(ethylcarbamoyl)phenyl)-5-nitrofuran-2-carboxamide

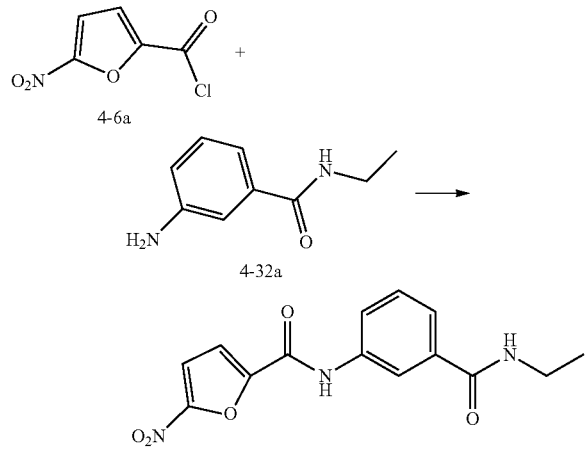

The synthesis method was the same as that in Example 1. Yellow solid, with a yield of 85%, and a melting point of 197-199° C.

$^1$H NMR (400 MHz, DMSO-d$_6$) δ 10.77 (s, 1H), 8.50 (t, J=5.2 Hz, 1H), 8.16 (t, J=1.8 Hz, 1H), 7.94 (dd, J=8.0, 1.2 Hz, 1H), 7.83 (d, J=3.9 Hz, 1H), 7.68 (d, J=3.9 Hz, 1H), 7.62 (d, J=8.0 Hz, 1H), 7.47 (t, J=8.0 Hz, 1H), 3.32-3.26 (m, 2H), 1.13 (t, J=7.2 Hz, 3H). $^{13}$C NMR (101 MHz, DMSO-d$_6$) δ 166.08, 155.15, 152.30, 148.18, 138.37, 135.94, 129.19, 123.53, 123.26, 120.47, 117.12, 113.92, 34.55, 15.24. HRMS m/z calcd for C$_{14}$H$_{14}$N$_3$O$_5$ [M+H]$^+$: 304.09280; found: 304.09286.

Example 56: N-(3-(isopropylcarbamoyl)phenyl)-5-nitrofuran-2-carboxamide

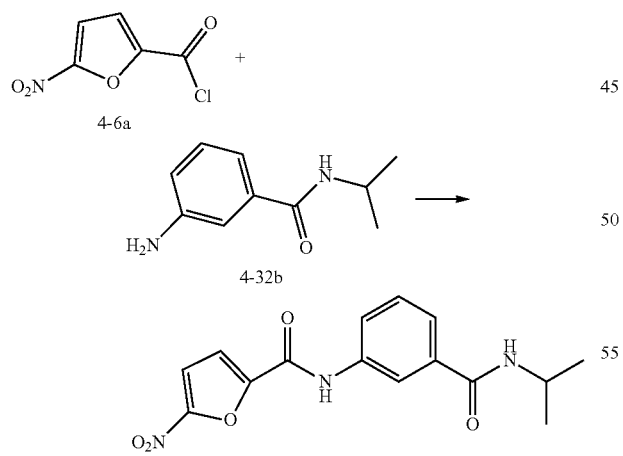

The synthesis method was the same as that in Example 1. Yellow solid, with a yield of 31%, and a melting point of 196-198° C.

$^1$H NMR (400 MHz, DMSO-d$_6$) δ 10.77 (s, 1H), 8.26 (d, J=8.0 Hz, 1H), 8.12 (t, J=1.6 Hz, 1H), 7.95 (dd, J=8.0, 1.6 Hz, 1H), 7.83 (d, J=3.9 Hz, 1H), 7.68 (d, J=3.9 Hz, 1H), 7.63 (d, J=8.0 Hz, 1H), 7.46 (t, J=8.0 Hz, 1H), 4.14-4.07 (m, 1H), 1.17 (d, J=6.8 Hz, 6H). $^{13}$C NMR (101 MHz, DMSO-d$_6$) δ 165.53, 155.14, 152.29, 148.17, 138.27, 136.14, 129.09, 123.48, 120.55, 117.10, 113.92, 41.50, 22.77. HRMS m/z calcd for C$_{15}$H$_{16}$N$_3$O$_5$ [M+H]$^+$: 318.10845; found: 318.10893.

Example 57: N-(3-(isobutylcarbamoyl)phenyl)-5-nitrofuran-2-carboxamide

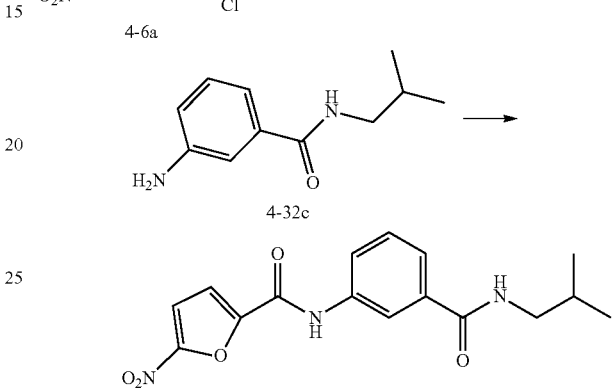

The synthesis method was the same as that in Example 1. Yellow solid, with a yield of 45%, and a melting point of 191-192° C.

$^1$H NMR (400 MHz, DMSO-d$_6$) δ 10.78 (s, 1H), 8.50 (t, J=5.4 Hz, 1H), 8.15 (s, 1H), 7.94 (d, J=8.0 Hz, 1H), 7.83 (d, J=3.9 Hz, 1H), 7.68 (d, J=3.9 Hz, 1H), 7.62 (d, J=8.0 Hz, 1H), 7.47 (t, J=8.0 Hz, 1H), 3.08 (t, J=6.4 Hz, 2H), 1.88-1.81 (m, 1H), 0.89 (d, J=6.4 Hz, 6H). $^{13}$C NMR (101 MHz, DMSO-d$_6$) δ 166.48, 155.16, 152.31, 148.20, 138.37, 136.11, 129.19, 123.53, 123.35, 120.19, 117.13, 113.94, 47.21, 28.57, 20.69. HRMS m/z calcd for C$_{15}$H$_{16}$N$_3$O$_5$ [M+H]$^+$: 318.10845; found: 318.10893.

Example 58: N-(3-(cyclohexylcarbamoyl)phenyl)-5-nitrofuran-2-carboxamide

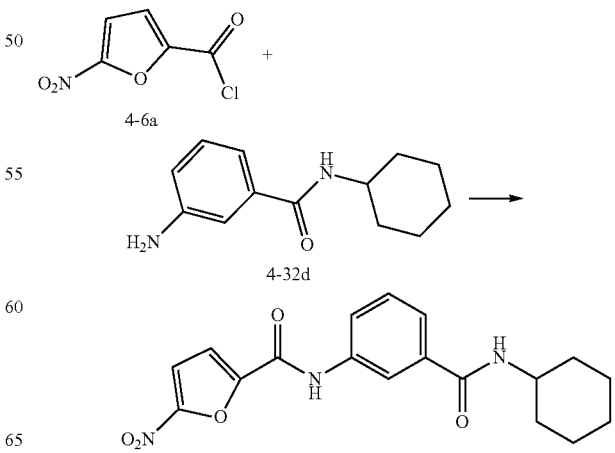

The synthesis method was the same as that in Example 1. Yellow solid, with a yield of 48%, and a melting point of 249-252° C.

¹H NMR (400 MHz, DMSO-d₆) δ 10.78 (s, 1H), 8.25 (d, J=7.8 Hz, 1H), 8.12 (s, 1H), 7.97 (d, J=7.8 Hz, 1H), 7.84 (d, J=3.9 Hz, 1H), 7.70 (d, J=3.9 Hz, 1H), 7.64 (d, J=7.8 Hz, 1H), 7.46 (d, J=7.8 Hz, 1H), 3.78 (s, 1H), 1.88-1.72 (m, 4H), 1.62 (d, J=11.8 Hz, 1H), 1.38-1.24 (m, 4H), 1.20-1.10 (m, 1H). ¹³C NMR (101 MHz, DMSO-d₆) δ 165.54, 155.15, 152.31, 148.20, 138.28, 136.17, 129.09, 123.51, 120.59, 117.11, 113.93, 48.86, 32.85, 25.73, 25.41. HRMS m/z calcd for $C_{15}H_{16}N_3O_5$ [M+H]⁺: 318.10845; found: 318.10893.

Example 59 N-(3-(benzylcarbamoyl)phenyl)-5-nitrofuran-2-carboxamide

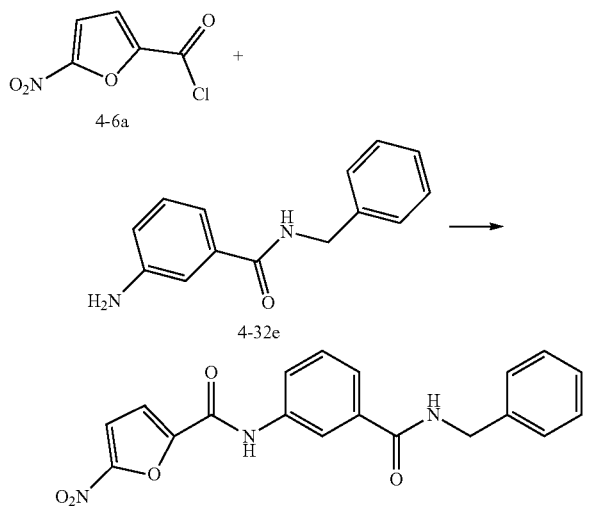

The synthesis method was the same as that in Example 1. Yellow solid, with a yield of 69%, and a melting point of 165-167° C.

¹H NMR (400 MHz, DMSO-d₆) δ 10.80 (s, 1H), 9.10 (s, 1H), 8.21 (s, 1H), 7.97 (d, J=7.8 Hz, 1H), 7.82 (d, J=3.2 Hz, 1H), 7.70-7.68 (m, 2H), 7.49 (t, J=7.8 Hz, 1H), 7.40-7.19 (m, 5H), 4.49 (d, J=5.4 Hz, 2H). ¹³C NMR (101 MHz, DMSO-d₆) δ 166.39, 155.15, 152.29, 148.15, 140.06, 138.44, 135.60, 129.30, 128.75, 127.65, 127.21, 123.76, 123.37, 120.57, 117.14, 113.91, 43.09. HRMS m/z calcd for $C_{15}H_{16}N_3O_5$ [M+H]⁺: 318.10845; found: 318.10893.

Example 60: N-(3-((2-dimethylaminoethyl)carbamoyl)phenyl)-5-nitrofuran-2-carboxamide

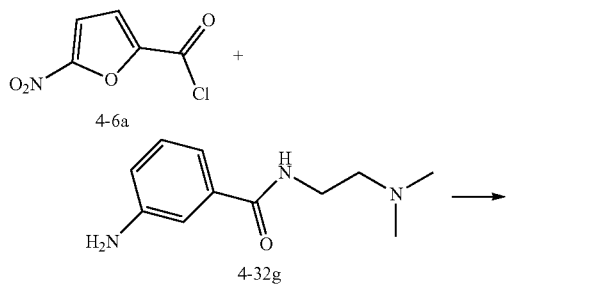

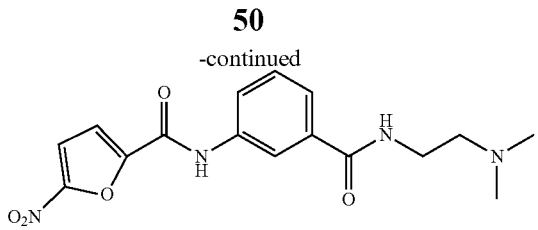

The synthesis method was the same as that in Example 1. Yellow solid, with a yield of 85%, and a melting point of 149-150° C.

¹H NMR (400 MHz, CDCl₃) δ 8.71 (s, 1H), 8.02 (s, 1H), 7.97 (dd, J=8.0, 1.2 Hz, 1H), 7.60 (d, J=8.0 Hz, 1H), 7.46 (t, J=8.0 Hz, 1H), 7.42 (d, J=3.8 Hz, 1H), 7.39 (d, J=3.8 Hz, 1H), 6.97 (s, 1H), 3.53 (q, J=5.6 Hz, 2H), 2.53 (t, J=5.6 Hz, 2H), 2.28 (s, 6H). ¹³C NMR (101 MHz, DMSO-d₆) δ 166.24, 155.18, 152.27, 148.28, 138.53, 135.77, 129.20, 123.64, 123.24, 120.46, 117.09, 113.93, 58.62, 45.74, 37.91. HRMS m/z calcd for $C_{15}H_{16}N_3O_5$ [M+H]⁺: 318.10845; found: 318.10893.

Example 61: N-(3-((2-morpholinylethyl)carbamoyl)phenyl)-5-nitrofuran-2-carboxamide

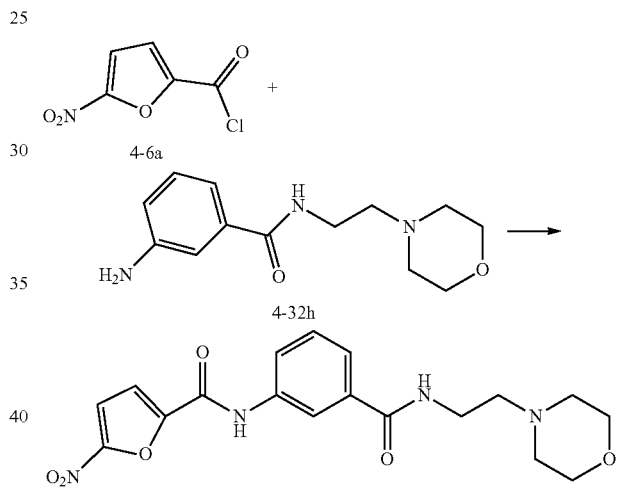

The synthesis method was the same as that in Example 1. White solid, with a yield of 49%, and a melting point of 193-194° C.

¹H NMR (400 MHz, DMSO-d₆) δ 10.78 (s, 1H), 8.44 (t, J=5.6 Hz, 1H), 8.16 (t, J=1.6 Hz, 1H), 7.94 (dd, J=8.0, 1.2 Hz, 1H), 7.82 (d, J=3.9 Hz, 1H), 7.67 (d, J=3.9 Hz, 1H), 7.60 (d, J=8.0 Hz, 1H), 7.47 (t, J=8.0 Hz, 1H), 3.57 (t, J=4.4 Hz, 4H), 3.40 (q, J=6.4 Hz, 3H), 2.52-2.40 (m, 6H). ¹³C NMR (101 MHz, DMSO-d₆) δ 166.32, 155.22, 152.26, 148.41, 138.69, 135.79, 129.21, 123.69, 123.18, 120.51, 117.04, 113.94, 66.66, 57.80, 53.76, 37.05. HRMS m/z calcd for $C_{18}H_{21}N_4O_6$ [M+H]⁺: 389.14556; found: 389.14653.

Example 62: N-(3-((3-morpholinylpropyl)carbamoyl)phenyl)-5-nitrofuran-2-carboxamide

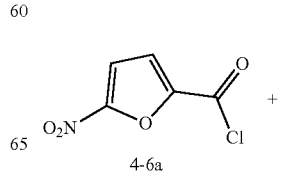

-continued

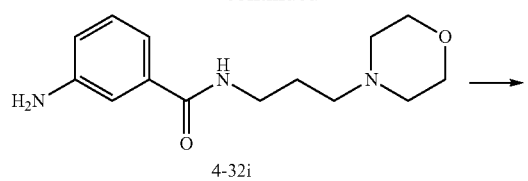

4-32i

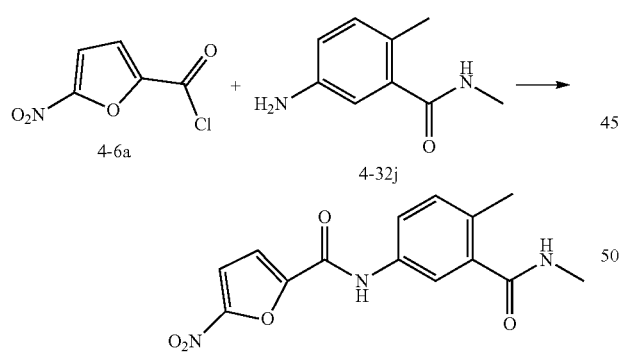

The synthesis method was the same as that in Example 1. Yellow solid, with a yield of 68%, and a melting point of 156-158° C.

$^1$H NMR (400 MHz, CDCl$_3$) δ 8.44 (s, 1H), 8.10 (s, 1H), 8.03 (s, 1H), 7.92 (d, J=8.0 Hz, 1H), 7.61 (d, J=8.0 Hz, 1H), 7.48 (t, J=8.0 Hz, 1H), 7.41 (d, J=8.0 Hz, 2H), 3.69 (s, 4H), 3.59 (d, J=5.2 Hz, 2H), 2.66-2.42 (m, 6H), 1.80 (s, 2H). $^{13}$C NMR (101 MHz, CDCl$_3$) δ 166.63, 154.12, 147.49, 136.91, 136.19, 129.48, 123.57, 122.97, 119.06, 117.01, 112.63, 66.95, 58.70, 53.83, 40.74, 24.13. HRMS m/z calcd for C$_{18}$H$_{21}$N$_4$O$_6$ [M+H]$^+$: 389.14556; found: 389.14653.

Example 63: N-(4-methyl-3-methylcarbamoylphenyl)-5-nitrofuran-2-carboxamide

The synthesis method was the same as that in Example 1. Yellow solid, with a yield of 65%, and a melting point of 225-226° C.

$^1$H NMR (400 MHz, DMSO-d$_6$) δ 10.65 (s, 1H), 8.20 (d, J=4.4 Hz, 1H), 7.82 (d, J=3.6 Hz, 1H), 7.72 (s, 2H), 7.64 (d, J=3.6 Hz, 1H), 7.25 (d, J=8.8 Hz, 1H), 2.76 (d, J=4.4 Hz, 3H), 2.29 (s, 3H). $^{13}$C NMR (101 MHz, DMSO-d$_6$) δ 169.59, 154.96, 148.27, 138.14, 135.84, 131.51, 131.22, 121.59, 119.67, 116.97, 113.94, 26.37, 19.27. HRMS m/z calcd for C$_{18}$H$_{21}$N$_4$O$_6$ [M+H]$^+$: 389.14556; found: 389.14653.

Example 64: N-(5-methyl-3-methylcarbamoylphenyl)-5-nitrofuran-2-carboxamide

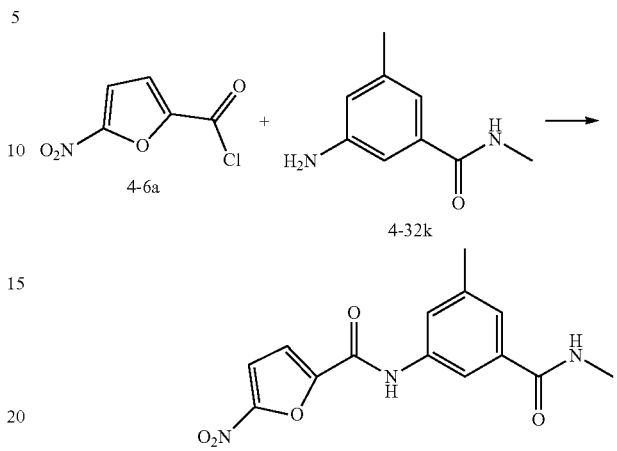

The synthesis method was the same as that in Example 1. Yellow solid, with a yield of 63%, and a melting point of 195-198° C.

$^1$H NMR (400 MHz, DMSO-d$_6$) δ 10.69 (s, 1H), 8.42 (d, J=4.8 Hz, 1H), 7.97 (s, 1H), 7.82 (d, J=3.9 Hz, 1H), 7.76 (s, 1H), 7.67 (d, J=3.9 Hz, 1H), 7.44 (s, 1H), 2.78 (d, J=4.4 Hz, 3H), 2.37 (s, 3H). $^{13}$C NMR (101 MHz, DMSO-d$_6$) δ 166.89, 155.07, 152.29, 148.20, 138.60, 138.30, 135.73, 123.97, 117.73, 117.04, 113.92, 26.76, 21.64. HRMS m/z calcd for C$_{18}$H$_{21}$N$_4$O$_6$ [M+H]$^+$: 389.14556; found: 389.14653.

Example 65: N-(4-fluoro-3-methylcarbomoylphenyl)-5-nitrofuran-2-carboxamide

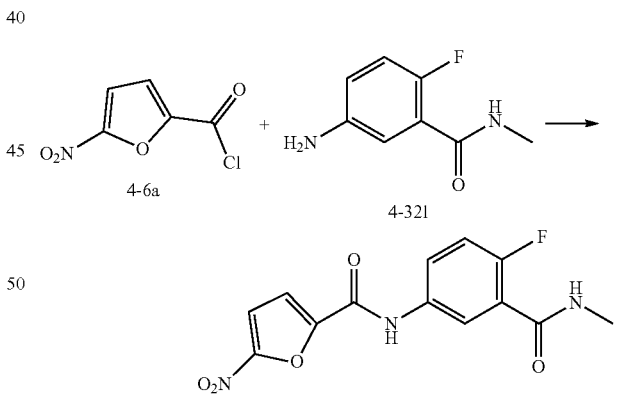

The synthesis method was the same as that in Example 1. Yellow solid, with a yield of 35%, and a melting point of 195-198° C.

$^1$H NMR (400 MHz, DMSO-d$_6$) δ 10.69 (s, 1H), 8.42 (d, J=4.8 Hz, 1H), 7.97 (s, 1H), 7.82 (d, J=3.9 Hz, 1H), 7.76 (s, 1H), 7.67 (d, J=3.9 Hz, 1H), 7.44 (s, 1H), 2.78 (d, J=4.4 Hz, 3H), 2.37 (s, 3H). $^{13}$C NMR (101 MHz, DMSO-d$_6$) δ 166.89, 155.07, 152.29, 148.20, 138.60, 138.30, 135.73, 123.97, 117.73, 117.04, 113.92, 26.76, 21.64. HRMS m/z calcd for C$_{18}$H$_{21}$N$_4$O$_6$ [M+H]$^+$: 389.14556; found: 389.14653.

Example 66: N-(5-fluoro-3-methylcarbomoylphenyl)-5-nitrofuran-2-carboxamide

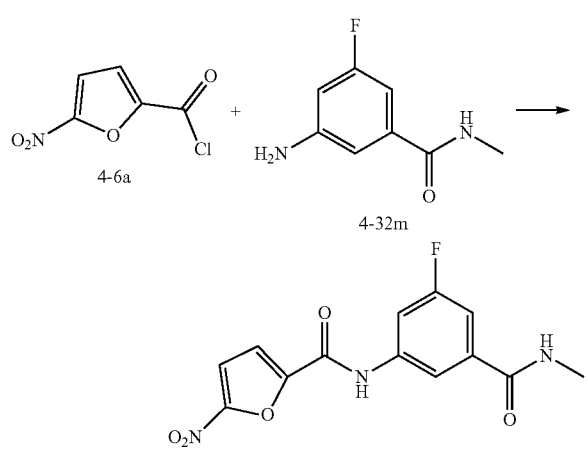

The synthesis method was the same as that in Example 1. The product was separated by silica gel column chromatography (CH$_2$Cl$_2$:MeOH=25:1) to give a yellow solid, with a yield of 40% and a melting point of 211-213° C.

$^1$H NMR (400 MHz, DMSO-d$_6$) δ 10.97 (s, 1H), 8.58 (d, J=4.2 Hz, 1H), 8.05 (s, 1H), 7.92 (d, J=10.8 Hz, 1H), 7.85 (d, J=3.9 Hz, 1H), 7.71 (d, J=3.9 Hz, 1H), 7.47 (d, J=9.2 Hz, 1H), 2.82 (d, J=4.4 Hz, 3H). $^{13}$C NMR (101 MHz, DMSO-d$_6$) δ 165.48, 163.31, 160.90, 155.31, 152.36, 147.75, 140.07, 139.95, 137.41, 137.33, 117.51, 116.29, 113.88, 110.26, 110.00, 109.82, 109.59, 26.80. HRMS m/z calcd for C$_{18}$H$_{21}$N$_4$O$_6$ [M+H]$^+$: 389.14556; found: 389.14653.

Example 67: N-(4-hydroxy-3-methylcarbomoylphenyl)-5-nitrofuran-2-carboxamide

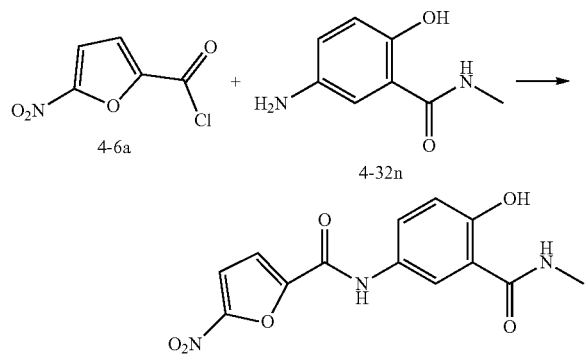

The synthesis method was the same as that in Example 5A. Yellow solid, with a yield of 30%, and a melting point of 260-262° C.

$^1$H NMR (400 MHz, DMSO-d$_6$) δ 12.16 (s, 1H), 10.60 (s, 1H), 8.73 (d, J=3.6 Hz, 1H), 8.09 (s, 1H), 7.82 (d, J=3.6 Hz, 1H), 7.66-7.59 (m, 2H), 6.94 (d, J=8.8 Hz, 1H), 2.82 (d, J=4.0 Hz, 3H). $^{13}$C NMR (101 MHz, DMSO-d$_6$) δ 168.45, 156.53, 154.94, 152.21, 148.50, 129.13, 127.72, 122.35, 117.81, 116.70, 114.00, 26.61. HRMS m/z calcd for C$_{18}$H$_{21}$N$_4$O$_6$ [M+H]$^+$: 389.14556; found: 389.14653.

Example 68: N$^1$,N$^3$-dimethyl-5-(5-nitrofuran-2-carboxamide) isophthalamide

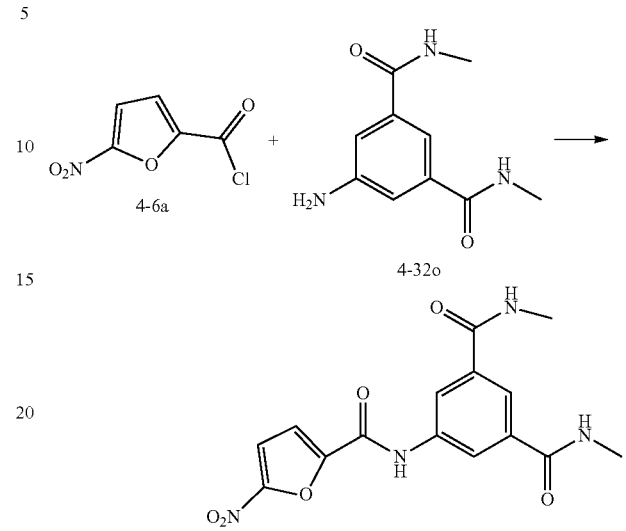

The synthesis method was the same as that in Example 1. Yellow solid, with a yield of 55%, and a melting point of 151-153° C.

$^1$H NMR (400 MHz, DMSO-d$_6$) δ 10.92 (s, 1H), 8.56 (d, J=4.4 Hz, 2H), 8.35 (s, 2H), 8.06 (s, 1H), 7.86 (d, J=3.9 Hz, 1H), 7.73 (d, J=3.9 Hz, 1H), 2.83 (d, J=4.4 Hz, 6H). $^{13}$C NMR (101 MHz, DMSO-d$_6$) δ 166.59, 155.23, 152.36, 147.96, 138.50, 135.99, 122.46, 121.86, 117.30, 113.92, 26.82. HRMS m/z calcd for C$_{18}$H$_{21}$N$_4$O$_6$ [M+H]$^+$: 389.14556; found: 389.14653.

Example 69

N-(2-methyl-1,3-dihydro-1,3-dioxo-2H-isoindol-5-yl)-5-nitrofuran-2-carboxamide

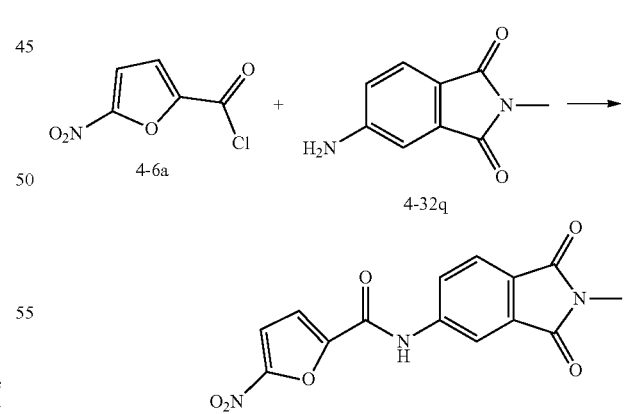

The synthesis method was the same as that in Example 1. Yellow solid, with a yield of 50%, and a melting point of 252-254° C.

$^1$H NMR (400 MHz, DMSO-d$_6$) δ 11.09 (s, 1H), 8.26 (d, J=1.6 Hz, 1H), 8.09 (dd, J=8.2, 1.6 Hz, 1H), 7.87 (d, J=8.2 Hz, 1H), 7.83 (d, J=3.9 Hz, 1H), 7.69 (d, J=3.9 Hz, 1H), 3.02 (s, 3H). $^{13}$C NMR (101 MHz, DMSO-d$_6$) δ 168.11, 168.01, 155.52, 152.42, 147.61, 143.68, 133.64, 127.29, 125.09, 124.50, 117.92, 114.60, 113.90, 24.24. HRMS m/z calcd for $C_{18}H_{21}N_4O_6$ [M+H]$^+$: 389.14556; found: 389.14653.

Example 70: N-(4-acetamidophenyl)-5-acetylfuran-2-carboxamide 5-acetylfuran-2-carboxylic acid (4-14e)

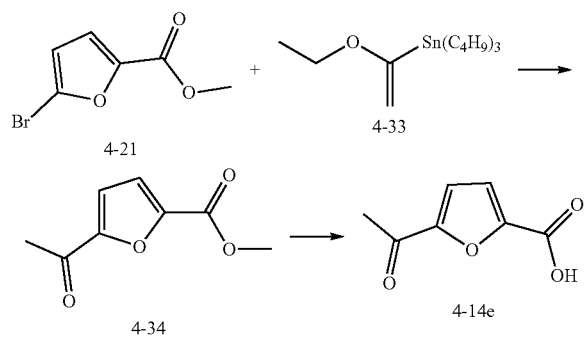

4-21 (205 mg, 1 mmol) was dissolved in anhydrous DMF (5 mL), added with 4-33 (361 mg, 1.5 mmol), PdCl$_2$(PPh$_3$)$_2$ (70 mg, 0.1 mmol), and stirred at 115° C. for 18 h under argon protection. TLC (PE:EA=3:1) showed that the reaction was almost completed. The reaction solution was cooled to room temperature, added with hydrochloric acid (4N, 0.5 mL), and the mixture was stirred for 30 min. 15 mL of water was added to the reaction system, which was extracted with ethyl acetate (15 mL×3). The organic phases were combined, dried over anhydrous Na$_2$SO$_4$ and concentrated. The product was separated by silica gel column chromatography (PE:EA=10:1) to give 4-34, 100 mg of a white solid, with a yield of 60%.

Tetrahydrofuran (4 mL) and LiOH aqueous solution (3N, 1 mL) were added to 4-34 (100 mg, 6 mmol), stirred at room temperature for 5 min, and TLC (PE:EA=3:1) showed that the reaction was completed. Most of the solvent was removed by rotary evaporation, and the residue was added with water (5 mL), adjusted to pH=3-4 with 4N hydrochloric acid, and extracted with ethyl acetate (5 mL×3). The organic phases were combined, washed with saturated NaCl, dried over anhydrous Na$_2$SO$_4$, and concentrated to give 4-14e, 90 mg of a white solid, with a yield of 98%.

N-(4-acetamidophenyl)-5-acetylfuran-2-carboxamide (Example 70)

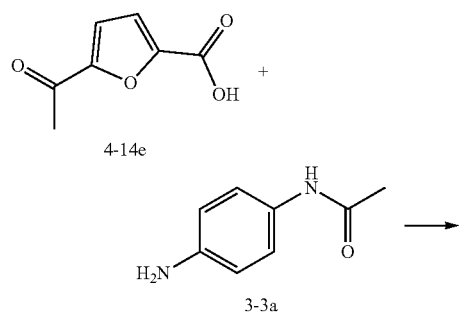

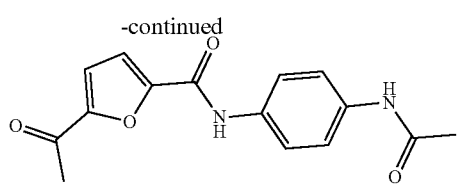

The synthesis method was the same as that in Example 5A. Light yellow solid, with a yield of 82%, and a melting point of 250-251° C.

$^1$H NMR (400 MHz, DMSO-d$_6$) δ 10.37 (s, 1H), 9.95 (s, 1H), 7.64 (d, J=8.8 Hz, 2H), 7.58-7.54 (m, 3H), 7.45 (d, J=3.6 Hz, 1H), 2.53 (s, 3H), 2.04 (s, 3H). $^{13}$C NMR (101 MHz, DMSO-d$_6$) δ 187.18, 168.55, 155.92, 152.90, 150.25, 136.25, 133.57, 121.69, 119.67, 119.37, 116.04, 26.78, 24.40. HRMS m/z calcd for $C_{15}H_{15}N_2O_4$ [M+H]$^+$: 287.10263; found: 287.10235.

Example 71: N-(4-(2-dimethylamino)acetamidophenyl)-5-nitrofuran-2-carboxamide

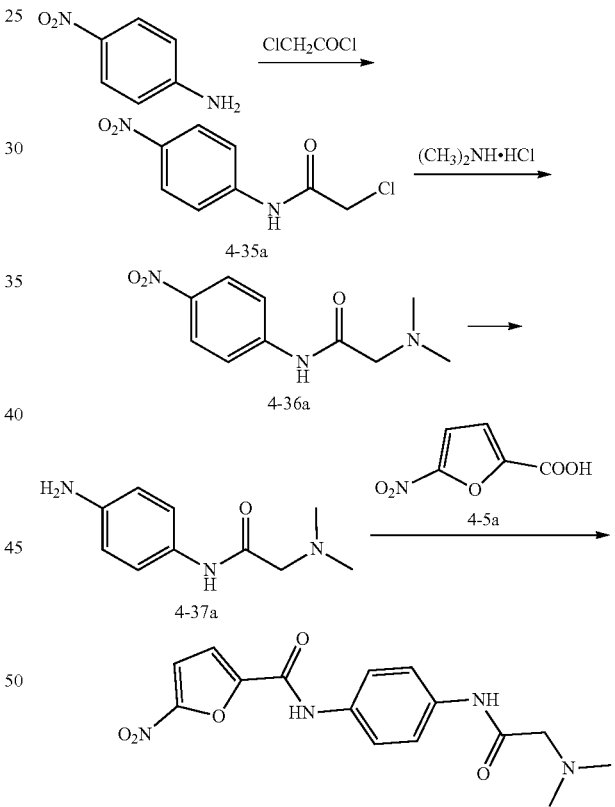

P-nitroaniline (276 mg, 2 mmol) and triethylamine (303 mg, 3 mmol) were added to tetrahydrofuran (10 mL), and added dropwise with chloroacetyl chloride (226 mg, 2 mmol) under an ice water bath. After the addition was completed, the reaction was stirred at room temperature for 2 h, and TLC (CH$_2$Cl$_2$:MeOH=10:1) showed that the reaction was completed. 1N HCl (20 mL) was added to the reaction solution, which was stirred for another 15 min, filtered with suction, and dried to give 408 mg of a yellow powder 4-35a, with a yield of 95%. 4-35a (214 mg, 1 mmol), dimethylamine hydrochloride (163 mg, 2 mmol), anhydrous potassium carbonate (414 mg, 3 mmol), sodium iodide (165 mg, 1.1 mmol), and acetonitrile (15 mL) were added into the reaction flask, stirred at 80° C. for 3 h, then TLC (CH$_2$Cl$_2$: MeOH=10:1) showed that the reaction was completed. The reaction solution was cooled and filtered with suction. The filtrate was concentrated. The residue was added with 15 mL of water and 15 mL of ethyl acetate. After mixing, the mixture was allowed to stand for separation. The aqueous phase was discarded. The organic phase was extracted with 2N hydrochloric acid (3 mL×3). The extracts were combined, and adjusted to pH=9 with saturated sodium bicarbonate aqueous solution. A yellow solid was precipitated, filtered and dried to give 4-36a, 150 mg, with a yield of 64%.

The synthesis method of 4-37a was the same as that of 4-25a, and it was directly used in the next reaction without separation.

The synthesis method of Example 71 was the same as that of Example 5A. Yellow solid, with a yield of 68%, and a melting point of 207-209° C.

$^1$H NMR (400 MHz, DMSO-d$_6$) δ 10.61 (s, 1H), 9.76 (s, 1H), 7.82 (d, J=3.5 Hz, 1H), 7.71-7.49 (m, 5H), 3.06 (s, 2H), 2.27 (s, 6H). $^{13}$C NMR (101 MHz, DMSO-d$_6$) δ 168.98, 154.79, 152.19, 148.50, 135.81, 133.60, 121.53, 120.23, 116.80, 113.98, 63.73, 45.83. HRMS m/z calcd for C$_{15}$H$_{16}$N$_4$O$_5$ [M+H]$^+$: 333.11935; found: 333.11900.

Example 72: N-(4-(2-morpholinyl)acetamidophenyl)-5-nitrofuran-2-carboxamide

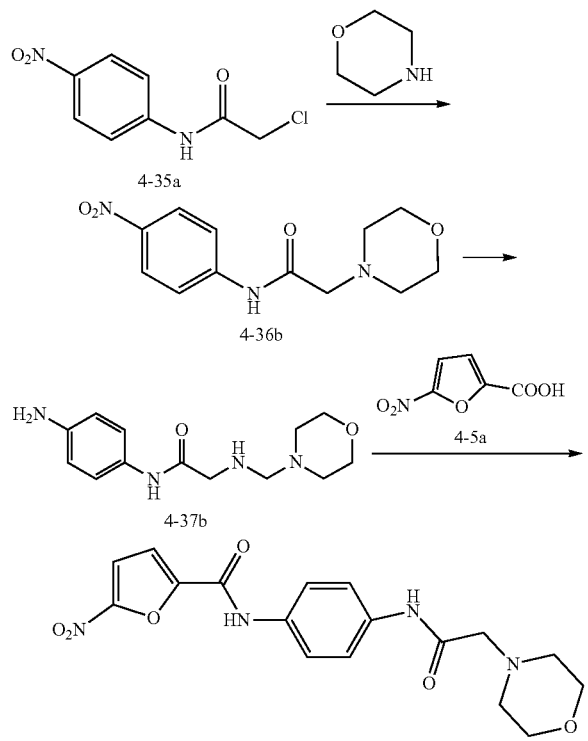

The synthesis method was the same as that in Example 71. Yellow solid, with a yield of 32%, and a melting point of 255-257° C.

$^1$H NMR (400 MHz, DMSO-d$_6$) δ 10.63 (s, 1H), 9.80 (s, 1H), 7.83 (d, J=3.8 Hz, 1H), 7.69-7.61 (m, 5H), 3.64 (t, J=4.0 Hz, 4H), 3.13 (s, 2H), 2.51 (t, J=4.0 Hz, 4H). $^{13}$C NMR (101 MHz, DMSO-d$_6$) δ 168.41, 154.81, 152.20, 148.49, 135.68, 133.71, 121.55, 120.29, 116.82, 113.99, 66.53, 62.48, 53.64. HRMS m/z calcd for C$_{17}$H$_{18}$N$_4$O$_6$ [M+H]$^+$: 375.12991; found: 375.13017.

Example 73: N-(4-(3-dimethylamino)propionylaminophenyl)-5-nitrofuran-2-carboxamide

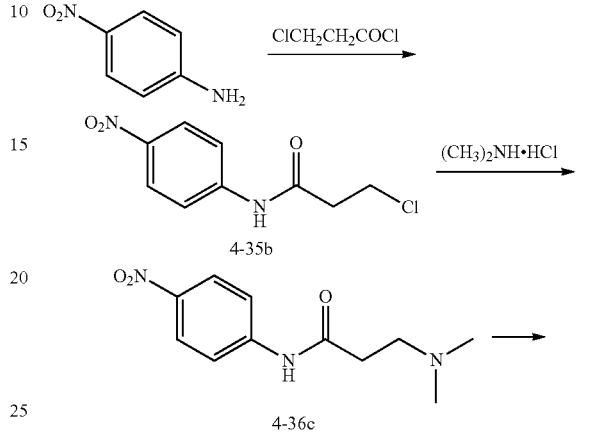

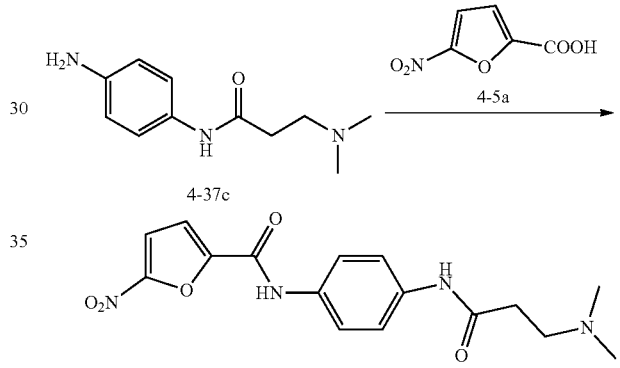

The synthesis method was the same as that in Example 71. Yellow solid, with a yield of 30%, and a melting point of 213-215° C.

$^1$H NMR (400 MHz, DMSO-d$_6$) δ 10.78 (s, 1H), 10.18 (s, 1H), 7.81 (d, J=1.5 Hz, 2H), 7.70 (d, J=8.8 Hz, 2H), 7.60 (d, J=8.8 Hz, 2H), 2.54 (t, J=6.9 Hz, 2H), 2.44 (t, J=6.9 Hz, 2H), 2.16 (s, 6H). $^{13}$C NMR (101 MHz, DMSO-d$_6$) δ 170.55, 154.79, 152.22, 148.58, 136.44, 133.45, 121.59, 119.68, 116.92, 113.95, 55.61, 45.44, 35.16. HRMS m/z calcd for C$_{16}$H$_{18}$N$_4$O$_5$ [M+H]$^+$: 347.13500; found: 347.13491.

Example 74

N-(4-((2-dimethylamino)ethylamino)acetamidophenyl)-5-nitrofuran-2-carboxamide

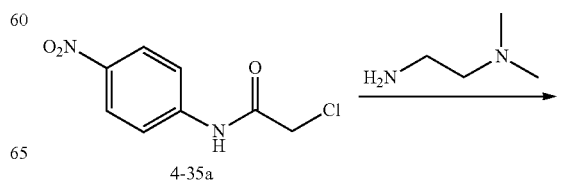

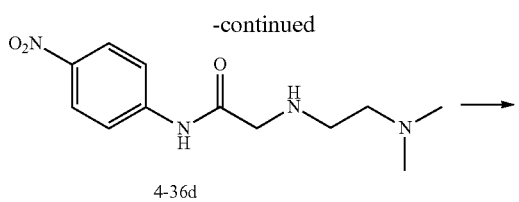

4-36d

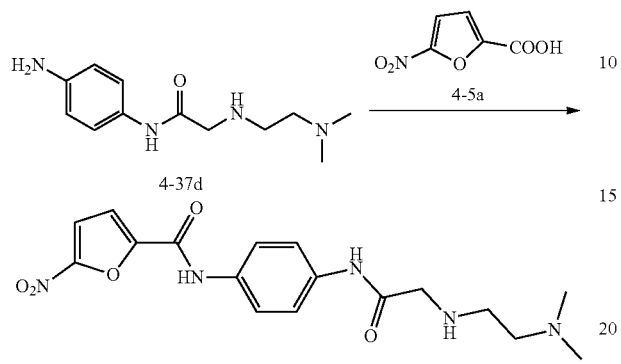

The synthesis method was the same as that in Example 71. Orange solid, with a yield of 28%, and a melting point of 160-162° C.

$^1$H NMR (400 MHz, CDCl$_3$) δ 9.80 (s, 1H), 8.24 (s, 1H), 7.80-7.53 (m, 4H), 7.42 (d, J=3.6 Hz, 1H), 7.37 (d, J=3.6 Hz, 1H), 3.41 (d, J=2.2 Hz, 2H), 2.78 (s, 2H), 2.45 (s, 2H), 2.28 (d, J=2.2 Hz, 6H). $^{13}$C NMR (101 MHz, CDCl$_3$) δ 170.42, 153.79, 147.94, 135.58, 132.19, 121.06, 120.08, 116.68, 112.73, 58.77, 53.09, 47.43, 45.34. HRMS m/z calcd for C$_{17}$H$_{21}$N$_5$O$_5$ [M+H]$^+$: 376.16155; found: 376.16271.

Example 75: ethyl 2-acetamido-5-(5-nitrofuran-2-carboxamide) benzoate

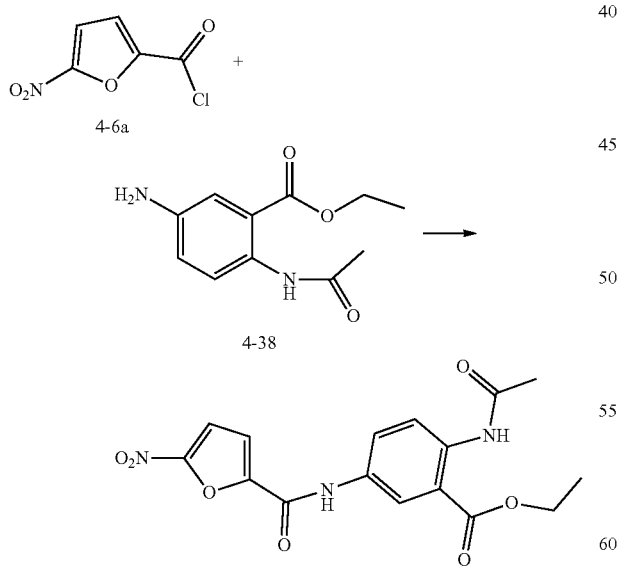

The synthesis method was the same as that in Example 1. Yellow solid, with a yield of 89%, and a melting point of 214-215° C.

$^1$H NMR (400 MHz, DMSO-d$_6$) δ 10.79 (s, 1H), 10.46 (s, 1H), 8.34 (d, J=2.5 Hz, 1H), 8.19 (d, J=9.0 Hz, 1H), 7.98 (dd, J=9.0, 2.5 Hz, 1H), 7.82 (d, J=3.9 Hz, 1H), 7.64 (d, J=3.9 Hz, 1H), 3.88 (s, 3H), 2.13 (s, 3H). $^{13}$C NMR (101 MHz, DMSO-d$_6$) δ 168.81, 167.57, 155.00, 152.25, 148.15, 136.39, 133.54, 126.29, 122.46, 117.08, 113.91, 52.84, 25.01. HRMS m/z calcd for C$_{15}$H$_{13}$N$_3$O$_7$ [M+H]$^+$: 348.08263; found: 348.08242.

Example 76: ethyl 5-(5-nitrofuran-2-carboxamide)-1H-pyrazole-4-carboxylate

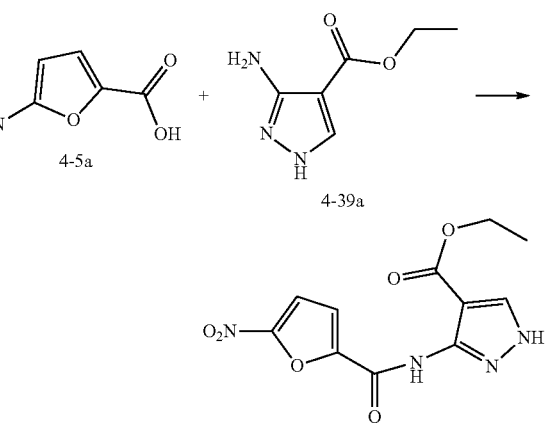

The synthesis method was the same as that in Example 5A. Yellow solid, with a yield of 48%, and a melting point of 174-175° C.

$^1$H NMR (400 MHz, CDCl$_3$) δ 8.15 (d, J=3.8 Hz, 1H), 7.80 (s, 1H), 7.41 (d, J=3.8 Hz, 1H), 4.32 (q, J=7.1 Hz, 2H), 1.37 (t, J=7.1 Hz, 3H). $^{13}$C NMR (101 MHz, CDCl$_3$) δ 163.67, 156.79, 154.70, 153.38, 144.86, 144.32, 125.33, 111.45, 94.67, 60.22, 14.48.

Example 77: ethyl 5-(5-nitrofuran-2-carboxamide)-1H-pyrazole-3-carboxylate

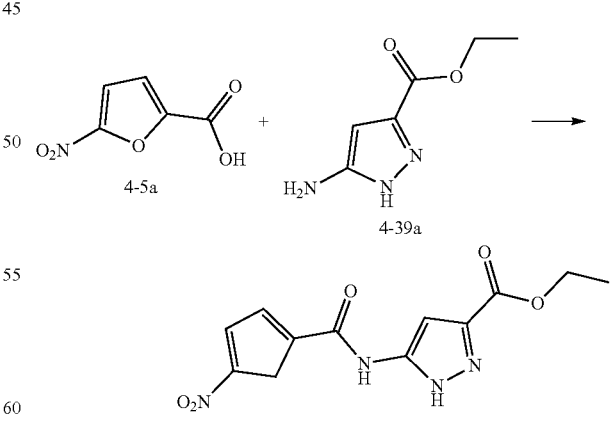

The synthesis method was the same as that in Example 5A. Yellow solid, with a yield of 30%.

$^1$H NMR (400 MHz, DMSO-d$_6$) δ 13.79 (s, 1H), 11.62 (s, 1H), 7.81 (d, J=3.8 Hz, 1H), 7.75 (d, J=3.8 Hz, 1H), 7.06 (s, 1H), 4.33 (q, J=7.1 Hz, 2H), 1.33 (t, J=7.1 Hz, 3H).

Example 78: 3-(5-acetyl-2-furoyl)carbamamide

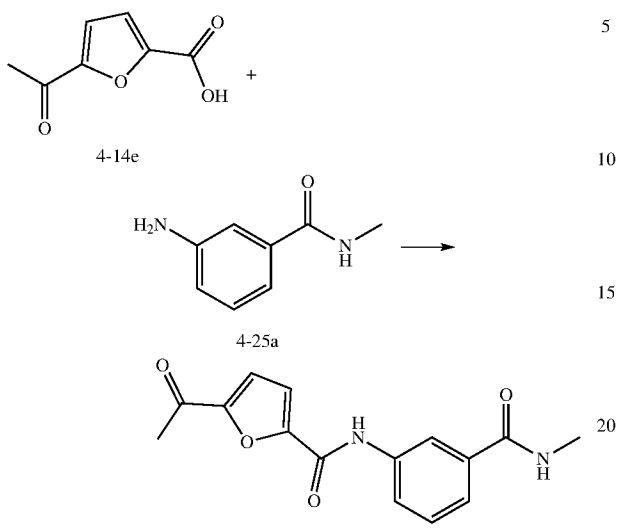

The synthesis method was the same as that in Example 5A. White solid, with a yield of 36%.

$^1$H NMR (400 MHz, CDCl$_3$) δ 8.63 (s, 1H), 8.09 (s, 1H), 7.85 (d, J=8.0 Hz, 1H), 7.59 (d, J=8.0 Hz, 1H), 7.44 (t, J=8.0 Hz, 1H), 7.31 (d, J=3.8 Hz, 1H), 7.26 (d, J=3.8 Hz, 1H), 6.38 (s, 1H), 3.02 (d, J=4.8 Hz, 3H), 2.56 (s, 3H). $^{13}$C NMR (101 MHz, CDCl$_3$) δ 186.51, 167.56, 155.52, 152.33, 149.69, 137.27, 135.60, 129.53, 123.50, 122.91, 119.12, 118.47, 116.52, 26.90, 26.29. HRMS m/z calcd for C$_{15}$H$_{14}$N$_2$O$_4$ [M+H]$^+$: 287.10263; found: 287.10218.

Example 79: N-3-(ethynylphenyl)-5-nitrofuran-2-carboxamide

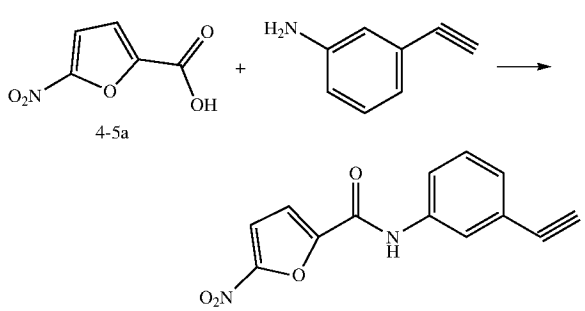

The synthesis method was the same as that in Example 1. The product was separated by silica gel column chromatography (PE:EA=5:1) to give a yellow solid, with a yield of 46% and a melting point of 173-174° C.

$^1$H NMR (400 MHz, CDCl$_3$) δ 8.20 (s, 1H), 7.82 (s, 1H), 7.69 (dt, J=7.4, 2.0 Hz, 1H), 7.42 (d, J=3.8 Hz, 1H), 7.39 (d, J=3.8 Hz, 1H), 7.34-7.31 (m, 2H), 3.11 (s, 1H). $^{13}$C NMR (101 MHz, CDCl$_3$) δ 153.96, 147.53, 136.39, 129.31, 129.22, 123.78, 123.28, 120.81, 117.02, 112.63, 82.72, 78.03.

Test Examples

Screening and Pharmacodynamic Evaluation of UT-B Inhibitors

1. Screening Test Method
   1) Blood was taken, placed in a 15 mL graduated centrifuge tube (suspended in PBS containing heparin sodium), and centrifuged at 3000 r/min for 10 min, then the supernatant was discarded;
   2) The same amount of PBS as blood was added, and centrifuged at 3000 r/min for 10 min, then the supernatant was discarded;
   3) The erythrocytes were diluted with hypertonic PBS containing 1.25 M urea to give a cell suspension with a specific volume of 2%;
   4) The erythrocyte suspension was incubated at room temperature for 2 h to balance the urea concentration inside and outside the cell, and mixed with a pipette regularly;
   5) 99 μL of the above erythrocyte suspension was put into each well of a 96-well round-bottom microplate, then added with 1 μL of the test compound, mixed well, and incubated at room temperature for 6 min (the final concentration of the test compound was 20 μM, and the final concentration of DMSO was 1%);
   6) Another 96-well flat-bottomed black wall microplate was taken, and added with 180 μL of isotonic PBS (containing 1% DMSO) to each well;
   7) 20 μL of the erythrocyte suspension in the above step 5) was taken, quickly added to a 96-well plate, and mixed well quickly;
   8) The absorbance value at a wavelength of 710 nm was measured with a microplate reader within 5 min;
   9) Each microplate was equipped with positive control wells (non-specific UT-B inhibitor phloretin) and negative control wells (PBS).

Erythrocyte lysis rate was calculated:

$$\% \ RBC \ \text{Lysis} = \frac{A_{neg} - A_{test}}{A_{neg} - A_{pos}} \times 100\%$$

The formula for calculating the lysis rate percentage of erythrocytes, wherein $A_{test}$ was the absorbance value of the test well, $A_{neg}$ was the absorbance value of the negative control well, and $A_{pos}$ was the absorbance value of the positive control well. Erythrocyte lysis rate was calculated by measuring absorption at a wavelength of 710 nm.

2. Discovery of Potential Compounds as Urea Transporter Inhibitors

In order to increase the chances of discovering potential urea transporter compounds, the present invention firstly screened out 1,040 compounds that may have UT-B inhibitory activity based on the molecular structure of UT-B protein by using computer simulation. The above compounds were dissolved in DMSO and diluted to 1 mM application solution in 96-well microtiter plates as a screening compound library.

The erythrocytes of three species of human, rats (SD rats) and mice (C57 mice) were taken, and urea transporter inhibitors were preliminarily screened from the above screening compound library by using the erythrocyte urea transporter inhibitor screening model. The concentration of the screened compounds was 10 μM, and the screening was repeated once to determine the potential compounds.

3. The Potential Compounds Specifically Inhibit the Urea Transporter

In order to determine the specificity of the potential compounds, erythrocytes were equilibrated with isotonic PBS or PBS containing 1.25 M urea, and the potential compounds (10 μM) were incubated and quickly transferred to isotonic PBS to detect the lysis rate of erythrocytes. Results: no obvious lysis was seen in the erythrocytes incubated with isotonic PBS, while the erythrocytes were lysed in those incubated with 1.25 M urea PBS. It indicated that, the rupture of the erythrocytes was caused by the specific inhibition of urea permeability of urea transporter proteins by the potential compounds.

4. Determination of the Best Potential Compound

Based on the parent nucleus structure of the obtained potential compounds, substituent replacement was carried out to obtain chemical structural analogues, so as to establish a secondary screening small molecule library. The above models and methods were used to screen and determine the activity, to obtain the results of the dose-effect experiment (Table 3) (Note: the $IC_{50}$ in Table 3 is the concentration when the erythrocyte lysis rate of mice, rats, and human was 50% respectively). As shown in Table 3, the compounds of the present invention all have urea transporter inhibitory effects and can be used as urea transporter inhibitors. After analysis and comparison, the compound of Example 3, which has a good inhibitory effect on the three species, was selected as an exemplary preferred compound (FIG. 2, part A to FIG. 2, part C).

5. The Inhibitory Effect of the Compound of Example 3 on the Urea Transporter UT-A In order to determine the inhibitory effect of the compound of Example 3 on UT-A, MDCK cells stably expressing UT-A1 were cultured into a compact monolayer in Transwell, and forskolin was used to stimulate the transfer of UT-A protein to the plasma membrane. The cells were incubated with the compound of Example 3 for 15 min, the culture medium under the Transwell was replaced by a culture medium containing 15 mM urea, and the urea concentration in the culture medium on the Transwell was detected at a specific time to evaluate the inhibitory effect of the compound of Example 3 on the permeability of UT-A urea.

The experimental results showed that, the exemplary compound of Example 3 of the present invention significantly inhibited the urea permeability mediated by UT-A1 (FIG. 2, part D), and the compound of Example 3 had a stronger inhibitory activity on UT-A than UT-B (FIG. 2, part E, FIG. 2, part F).

6. The Compound of Example 3 has an Obvious Diuretic Effect (1) SD rats, male, 6 in each group, weighing about 200 g, were taken. The animals were placed in a metabolic cage and acclimatized for three days prior to the experiment, on a standard diet with free access to water. The urine collection system was siliconized in advance to prevent urine loss. After the acclimatization, urine of 2 h was collected, and transferred to a pre-weighed EP tube. 100 mg/kg of the compound of Example 3 was injected subcutaneously, and urine was collected every two hours for a total of 12 h. Solvent control: corn oil. The weight of urine was measured by the weight loss method and converted to volume (1 g≈1 mL). The curve was drawn by taking time as the abscissa and urine volume as the ordinate, and the results were shown in FIG. 4, part A; compared with the solvent control group, the compound of Example 3 exhibited an obvious diuretic effect. The peak of the diuretic effect was at 4 h after administration, and the duration of the diuretic effect was about 6-8 h. The results were shown as means±SEM, n=6. The urine osmotic pressure of the collected urine was measured by using a freezing point osmometer. The curve was drawn by taking time as the abscissa and urine osmotic pressure as the ordinate, and the results were shown in FIG. 4, part B; compared with the solvent control group, the compound of Example 3 can significantly reduce the urine osmotic pressure. The peak of action was at 4 h after administration, and returned to the level before administration at 6-8 h after administration. The results were shown as means±SEM, n=6. The urine samples were detected by using a urea kit for the level of urea in the urine. According to the previously measured urine volume, urine osmotic pressure and urea excretion per 2 h, the excretion of non-urea solutes per 2 h was calculated. Compared with the control group, the non-urea solute excretion per 2 h of each dose group had no significant change (FIG. 3, part C). The results were shown as means±SEM, n=6.

(2) C57BL/6J mice, male, 6 in each group, weighing 20~22 g, were taken. The animals were placed in a metabolic cage and acclimatized for three days prior to the experiment, on a standard diet with free access to water. The urine collection system was siliconized in advance to prevent urine loss. After the acclimatization, urine of 2 h was collected, transferred to a pre-weighed test tube. 100 mg/kg of the compound of Example 3 was injected subcutaneously, and urine was collected every two hours for a total of 12 h. Solvent control: 40% corn oil. The weight of urine was measured by the weight loss method and converted to volume (1 g≈1 mL). The curve was drawn by taking time as the abscissa and urine volume as the ordinate, and the results were shown in FIG. 4, part A; compared with the solvent control group, the compound of Example 3 exhibited an obvious diuretic effect. The results were shown as means±SEM, n=6. The urine osmotic pressure of the collected urine was measured by using a freezing point osmometer. The curve was drawn by taking time as the abscissa and urine osmotic pressure as the ordinate, and the results were shown in FIG. 4, part B; compared with the solvent control group, the compound of Example 3 can significantly reduce the urine osmotic pressure. The results were shown as means±SEM, n=6. The urine samples were detected by using a urea kit for the level of urea in the urine. According to the previously measured urine volume, urine osmotic pressure and urea excretion per 2 h, the excretion of non-urea solutes per 2 h was calculated. Compared with the control group, the non-urea solute excretion per 2 h of each dose group had no significant change (FIG. 4, part C). The results were shown as means±SEM, n=6.

Figure 5:
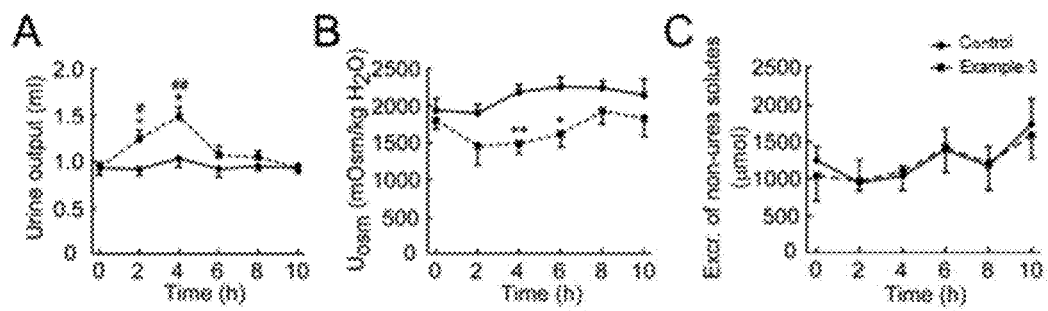
FIG. 5 exemplarily shows the diuretic effect and non-urea excretion of a single intragastric administration of the compound of Example 3 of the present invention in rats. The rats were put into a metabolic cage, and urine of 0~2 h was collected as the basal urine volume. Then, the experimental group was intragastrically administrated with 100 mg/kg of the compound of Example 3, and the control group was administrated with sodium carboxymethyl cellulose. A: urine volume; B: osmotic pressure; C: non-urea solute excretion. The results are shown as means ±standard error, n=6, *P<0.05, **P<0.01, representing the rats in the group administrated with the compound of Example 3 compared with the rats in the solvent control group; #P<0.05, ##P<0.01, representing the level after administrating with the compound of Example 3 compared with the basal level.
Figure 6:
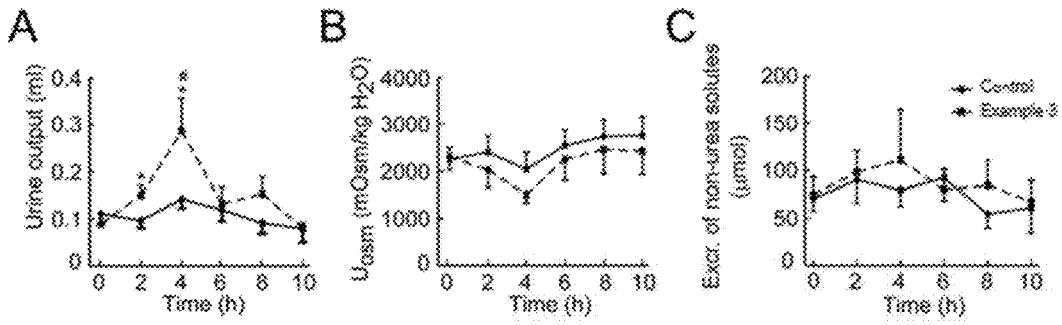
FIG. 6 exemplarily shows the diuretic effect and non-urea excretion of a single intragastric administration of the compound of Example 3 of the present invention in mice. The mice were put into a metabolic cage, and urine of 0~2 h was collected as the basal urine volume. Then, the experimental group was intragastrically administrated with 100 mg/kg of the compound of Example 3, and the control group was administrated with sodium carboxymethyl cellulose. A: urine volume; B: osmotic pressure; C: non-urea solute excretion. The results are shown as means ±standard error, n=6, *P<0.05, representing the mice in the group administrated with the compound of Example 3 compared with the mice in the solvent control group; #P<0.05, representing the level after administrating with the compound of Example 3 compared with the basal level.

(3) SD rats, male, 6 in each group, weighing about 200 g, were taken. The animals were placed in a metabolic cage and acclimatized for three days prior to the experiment, on a standard diet with free access to water. The urine collection system was siliconized in advance to prevent urine loss. After the acclimatization, urine of 2 h was collected, and transferred to a pre-weighed test tube. 100 mg/kg of the compound of Example 3 was injected subcutaneously, and urine was collected every two hours for a total of 12 h. Solvent control: 0.5% sodium carboxymethyl cellulose (CMC-Na). The weight of urine was measured by the weight loss method and converted to volume (1 g≈1 mL). The curve was drawn by taking time as the abscissa and urine volume as the ordinate, and the results were shown in FIG. 5, part A; compared with the solvent control group, the compound of Example 3 exhibited an obvious diuretic effect. Urine volume began to rise at 2 h after administration, the peak of diuretic effect was at 4 h after administration, and the duration of diuretic effect was about 6-8 h. The results were shown as means±SEM, n=6. The urine osmotic pressure of the collected urine was measured by using a freezing point osmometer. The curve was drawn by taking time as the abscissa and urine osmotic pressure as the ordinate, and the results were shown in FIG. 5, part B; compared with the solvent control group, the compound of Example 3 can significantly reduce the urine osmotic pressure. The peak of action was at 4 h after administration, and recovered to the level before administration at 6-8 h after administration. The results were shown as means±SEM, n=6. Urine samples were detected by using a urea kit for the level of urea in the urine. According to the previously measured urine volume, urine osmotic pressure and urea excretion per 2 h, the excretion of non-urea solutes per 2 h was calculated. Compared with the control group, the non-urea solute excretion per 2 h of each dose group had no significant change, as shown in FIG. 5, part C. C57BL/6J mice, male, 6 in each group, weighing 20~22 g, were taken. The animals were placed in a metabolic cage and acclimatized for three days prior to the experiment, on a standard diet with free access to water. The urine collection system was siliconized in advance to prevent urine loss. After the acclimatization, urine of 2 h was collected, and transferred to a pre-weighed test tube. 100 mg/kg of the compound of Example 3 was administrated intragastrically, and urine was collected every two hours for a total of 12 h. Solvent control: CMC-Na. The weight of urine was measured by the weight loss method and converted to volume (1 g≈1 mL). The curve was drawn by taking time as the abscissa and urine volume as the ordinate, and the results were shown in FIG. 6, part A; compared with the solvent control group, the compound of Example 3 exhibited an obvious diuretic effect. The results were shown as means±SEM, n=6. The urine osmotic pressure of the collected urine was measured by using a freezing point osmometer. The curve was drawn by taking time as the abscissa and urine osmotic pressure as the ordinate, and the results were shown in FIG. 6, part B; compared with the solvent control group, the compound of Example 3 can significantly reduce the urine osmotic pressure. The results were shown as means±SEM, n=6. The urine samples were detected by using a urea kit for the level of urea in the urine. According to the previously measured urine volume, urine osmotic pressure and urea excretion per 2 h, the excretion of non-urea solutes per 2 h was calculated. Compared with the control group, the non-urea solute excretion per 2 h of each dose group had no significant change (FIG. 6, part C). The results were shown as means ±SEM, n=6.

Subsequently, the present inventors further observed the long-term diuretic effect of the compound of Example 3. Normal C57BL/6J mice, 8 weeks old, male, 8 mice in each group were taken. The animals were placed in a metabolic cage and acclimatized for three days prior to the experiment, on a standard diet with free access to water. After the acclimatization, 100 mg/kg of the compound of Example 3 was administrated intragastrically (the first dose was doubled) every 8 h. Solvent control: 0.5% sodium carboxymethyl cellulose (CMC-Na). Urine was collected every 24 h, and transferred to a pre-weighed test tube. The administration was continued for 7 days, the body weight was recorded, and the results were shown in FIG. 7. The weight of urine was measured by the weight loss method and converted to volume (1 g≈1 mL). The curve was drawn by taking time as the abscissa and urine volume as the ordinate, and the results were shown in FIG. 7, part A; compared with the solvent control group, the urine volume began to increase on the first day after the administration of the compound of Example 3, and lasted to the 7th day. Compared with the solvent control group, the compound of Example 3 had an obvious diuretic effect. The results were shown as means±SEM, n=8. The urine osmotic pressure was measured by using a freezing point osmometer. The curve was drawn by taking time as the abscissa and urine osmotic pressure as the ordinate, and the results were shown in FIG. 7, part A; compared with the solvent control group, the urine osmotic pressure began to reduce on the first day after the administration of the compound of Example 3, and lasted to the 7th day, which indicated that the continuous administration of the compound of Example 3 can reduce the osmotic pressure of the urine of mice. The results were shown as means±SEM, n=8.

Figure 7:
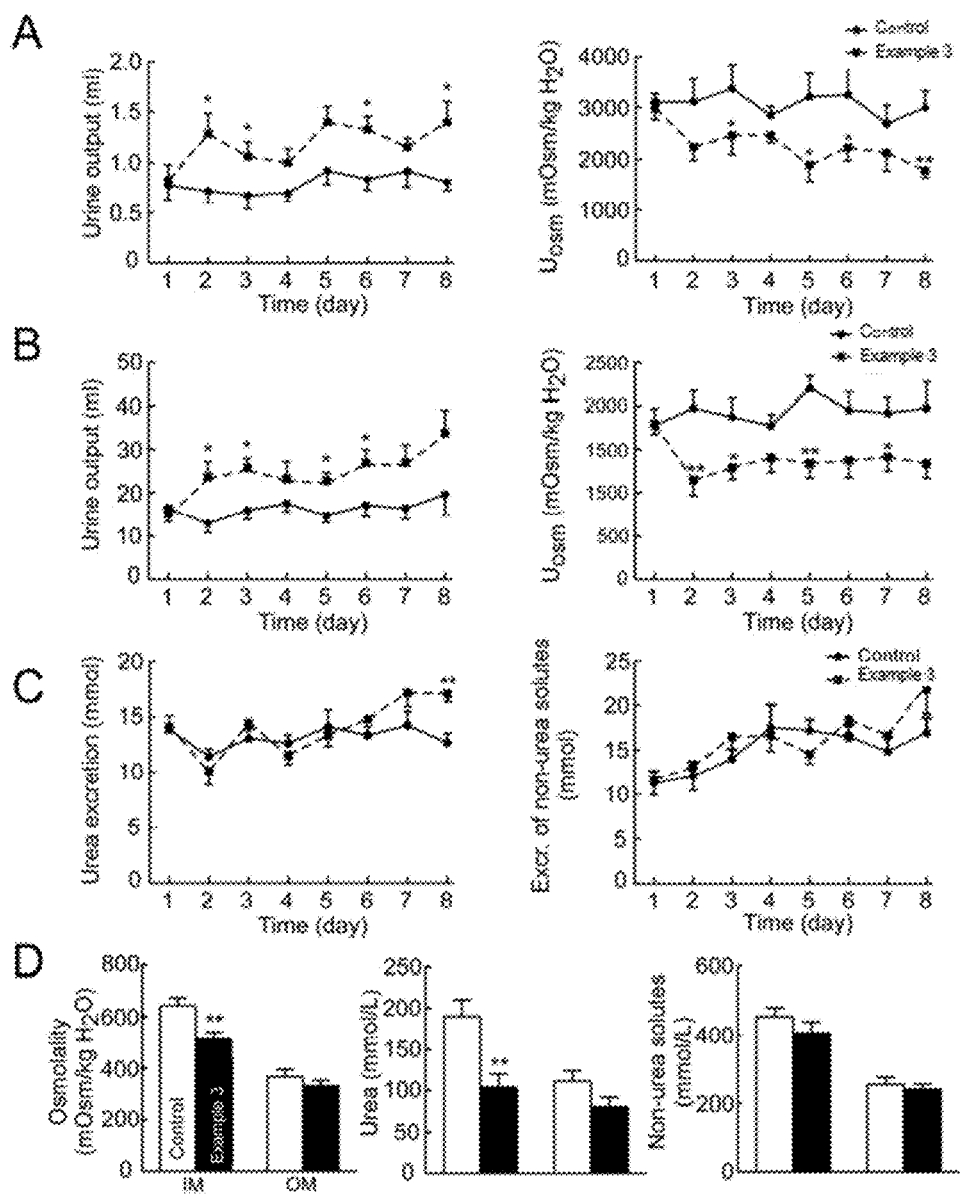
FIG. 7 exemplarily shows the diuretic effect of the compound of Example 3 of the present invention after long-term intragastric administration to rats and mice. Rats and mice were placed in metabolic cages, and one day's urine was taken as the basal urine volume. The experimental group was intragastrically administrated with 100 mg/kg of the compound of Example 3, and the control group was administrated with sodium carboxymethyl cellulose, three times a day (the first dose was doubled), continuously administrated for 7 days, and after the last administration, the inner and outer medulla of kidney were taken for analysis. A: urine volume of mice (left); urine osmotic pressure of mice (right). B: urine volume of rats (left); urine osmotic pressure of rats (right). C: urea excretion of rats (left); non-urea solute excretion of rats (right). D: inner and outer medullary osmotic pressure (left); inner and outer medullary urea concentration; inner and outer medullary non-urea concentration. Data are shown as means ±standard error; n=8; *P<0.05, **P<0.01, representing a comparison to the control group.

Normal SD rats, 8 weeks, male, 8 rats in each group were taken. The animals were placed in a metabolic cage and acclimatized for three days prior to the experiment, on a standard diet with free access to water. After the acclimatization, 100 mg/kg of the compound of Example 3 was administrated intragastrically (the first dose was doubled) every 8 h. Solvent control: 0.5% sodium carboxymethyl cellulose (CMC-Na). Urine was collected every 24 h, and transferred to a pre-weighed test tube. The administration was continued for 7 days. The body weight was recorded, and the results were shown in FIG. 7. The weight of urine was measured by the weight loss method and converted to volume (1 g≈1 mL). The curve was drawn by taking time as the abscissa and urine volume as the ordinate, and the results were shown in FIG. 7, part B; compared with the solvent control group, the urine volume began to increase on the first day after the administration of the compound of Example 3, and lasted to the 7th day. Compared with the solvent control group, the compound of Example 3 had an obvious diuretic effect. The results were shown as means±SEM, n=8. The urine osmotic pressure was measured by using a freezing point osmometer. The curve was drawn by taking time as the abscissa and urine osmotic pressure as the ordinate, and the results were shown in FIG. 7, part B; compared with the solvent control group, the urine osmotic pressure began to reduce on the first day after the administration of the compound of Example 3, and lasted to the 7th day, which indicated that the continuous administration of the compound of Example 3 can reduce the osmotic pressure of the urine of mice. The results were shown as means±SEM, n=8. According to the previously measured urine volume, urine osmotic pressure and urea excretion per 24 h, the excretion of non-urea solutes per 24 h was calculated. Compared with the control group, the urea and non-urea solute excretion per 24 h of each dose group had no significant change (FIG. 7, part C). The results were shown as means±SEM, n=8. Normal SD rats, 8 weeks, male, 8 rats in each group were taken. The animals were placed in a metabolic cage and acclimatized for three days prior to the experiment, on a standard diet with free access to water. After the acclimatization, 100 mg/kg of the compound of Example 3 was administrated intragastrically (the first dose was doubled) every 8 h. Solvent control: 0.5% sodium carboxymethyl cellulose (CMC-Na). The administration was continued and recorded for 7 days. On the 7th day, the rats were anesthetized with sodium pentobarbital, and the changes in osmotic pressure, urea and non-urea solute concentrations in the renal inner and outer medulla tissues were detected. The results were shown in FIG. 7, part D. The osmotic pressure in the renal inner medulla tissue fluid reduced significantly mainly due to the decreased concentration of urea, while the concentration of non-urea solutes had no significant change.

7. The Compound of Example 3 has No Obvious Toxicity

In order to study the cytotoxicity of the compound of the present invention, an MDCK cytotoxicity test was completed by using a CCK-8 kit. The results were shown in FIG. 8, part A, which indicated that the compound of Example 3 had no significant cytotoxic effect. In this study, a CCK-8 kit was used to detect the cytotoxicity of compounds: MDCK cell suspension in logarithmic growth phase was inoculated into a 96-well culture plate ($1\times10^4$ cells/well/100 μL), and 100 μL of DMEM culture solution containing 10% fetal bovine serum, 100 U/mL penicillin and 100 μg/mL streptomycin was administrated to each well, then cultured in a 37° C., 5% $CO_2$ incubator. When the cells were 70%-80% confluent, serum starvation was performed for 12 h for synchronization. Then each well was administrated with 100 μL of DMEM medium containing different concentrations (7.8, 15.6, 31.3, 62.5 and 125 μM) of the compound, and cultured for 12 h. Each well was administrated with 10 μL of CCK-8 detection solution, incubated at 37° C. in dark for 1 h, and detected the OD value at 470 nm. At the same time, blank wells (medium, CCK-8) and control wells (cells, dissolving medium of the same concentration compound, medium, CCK-8) were set up, 3 replicate wells per group. Cell survival rate was calculated: cell survival rate (%)= [($OD_{experimental\ well}-OD_{blank\ well}$)/($OD_{control\ well}-OD_{blank\ well}$)]×100%, wherein OD refers to the absorbance value of each well.

Figure 8:
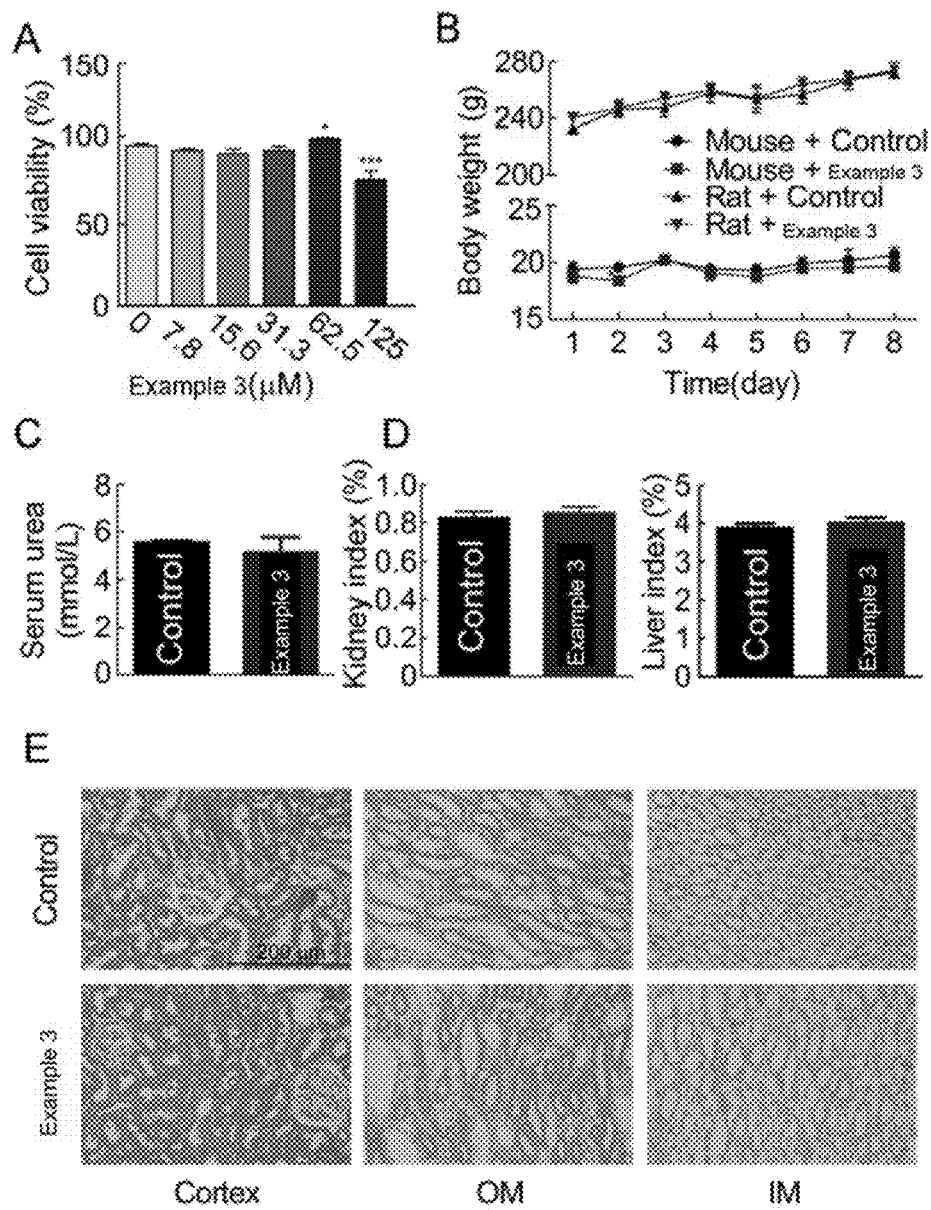
FIG. 8 exemplarily shows the verification of the toxicity of the compound of Example 3 of the present invention. Cell viability assays were performed using CCK-8 after 24 h of observation of MDCK cells added with the compounds of Example 3. Rats and mice were placed in metabolic cages. The experimental group was intragastrically administrated with 100 mg/kg of the compound of Example 3, and the control group was administrated with sodium carboxymethyl cellulose, three times a day (the first dose was doubled), continuously administrated for 7 days, observed and weighed, and after the last administration, the blood, kidney, and liver tissues were taken for analysis. A: cell survival rate; B: body weights of rats and mice; C: blood urea of rats; D: kidney index of rats (left), liver weight index of rats (right); E: kidney morphology of rats. Data are shown as means±standard error; n=8; *P<0.05, ***P<0.001, representing a comparison to the control group.

Normal SD rats, 8 weeks old, male, 8 rats in each group were taken. The animals were placed in a metabolic cage and acclimatized for three days prior to the experiment, on a standard diet with free access to water. After the acclimatization, 100 mg/kg of the compound of Example 3 was administered intragastrically (the first dose was doubled) every 8 h. Solvent control: 0.5% sodium carboxymethyl cellulose (CMC-Na). The administration was continued for 7 days. On the 7th day, the rats were anesthetized with sodium pentobarbital, and the liver and kidney were taken, weighed, and the kidney weight index and liver weight index were calculated. There was no significant difference with the control group (FIG. 8, part B, FIG. 8, part D). The effect of the compound of Example 3 on the serum urea level after the long-term administration was detected by using a urea kit, and it was found that there was no significant statistical difference with the control group (FIG. 8, part C). The kidney tissue was immersed in a fixative solution (4% paraformaldehyde), embedded with a paraffin embedding machine, and then cut into 6 μm thick paraffin sections by a paraffin microtome. The sections were treated with xylene for 15 min, twice; with xylene: anhydrous ethanol=1:1 for 2 min; with 100% ethanol for 5 min, twice; with 80% ethanol for 5 min, and distilled water for 5 min; and then firstly stained with hematoxylin semen for 5 min, subsequently washed to remove the hematoxylin semen by running water (1~3 s), then treated with 1% hydrochloric acid and ethanol for 1~3 s, washed with water for 10~30 s, overwashed with distilled water for 1~2 s, after then stained with 0.5% eosin solution for 1~3 min, then washed with distilled water for 1~2 s, washed with 80% ethanol for 1~2 s, 95% ethanol (I) for 2~3 s, 95% ethanol (II) for 3~5 s, anhydrous ethanol for 5~10 min, carboxylol for 5~10 min, xylene for 2 min, three times, and then sealed with neutral gum. The sections were observed under an optical microscope. The inner medulla, outer medulla, and cortex of each kidney were selected for comparative observation by an optical microscope. It was found that the compound of Example 3 did not significantly affect the histological morphology of the kidney. However, since the compound of Example 3 exerted a significant diuretic effect, tubule swelling appeared in the inner medullary after the administration of the compound of Example 3. Blood was collected by cardiac puncture, then centrifuged to obtain serum, which was used to measure serum indexes by instruments. It was found that the compound of Example 3 did not affect glucose metabolism and lipid metabolism (Table 2).

TABLE 1

Compound structures of Example 1 to Example 79 of the present invention

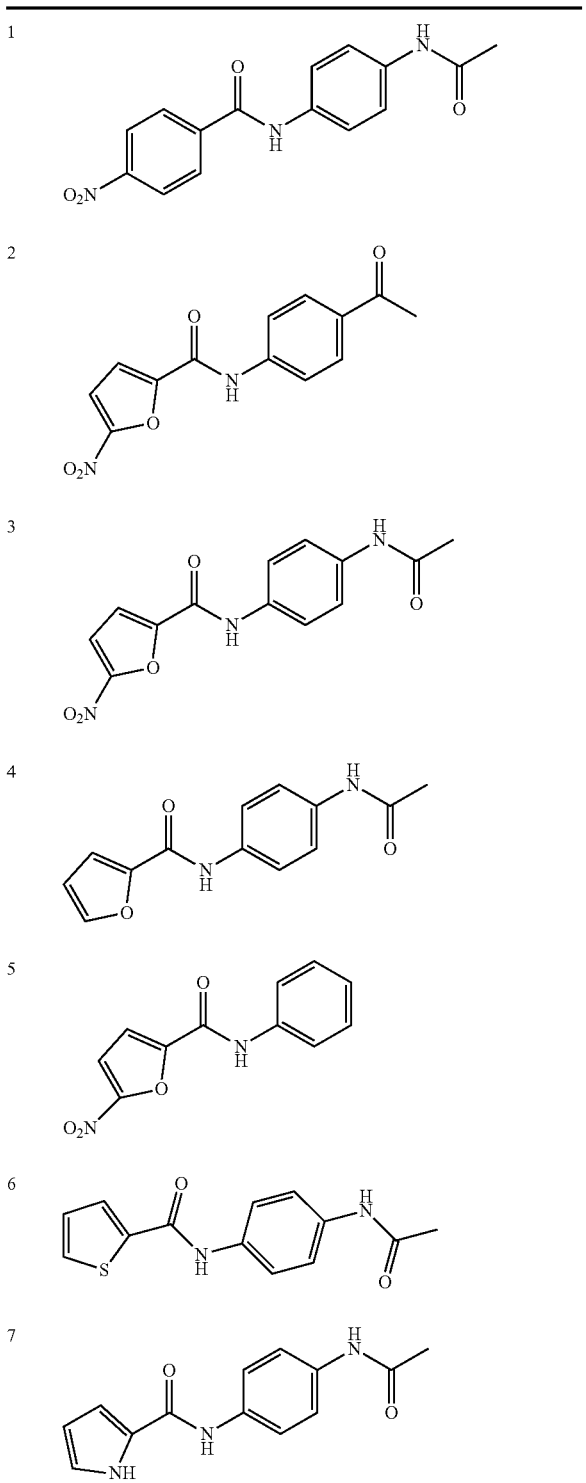

TABLE 1-continued

Compound structures of Example 1 to Example 79 of the present invention

| Ex. | Structure |
|---|---|
| 8 | oxazole-5-carboxamide with N-(4-acetamidophenyl) |
| 9 | 5-nitrothiophene-2-carboxamide with N-(4-acetamidophenyl) |
| 10 | 5-nitrofuran-2-carboxamide with N-(pyridin-2-yl) |
| 11 | 5-nitrofuran-2-carboxamide with N-(pyridin-3-yl) |
| 12 | 5-nitrofuran-2-carboxamide with N-(pyridin-4-yl) |
| 13 | 5-nitrofuran-2-carboxamide with N-(pyrazin-2-yl) |
| 14 | 5-nitrofuran-2-carboxamide with N-(pyrimidin-2-yl) |
| 15 | 5-nitrofuran-2-carboxamide with N-(pyridazin-3-yl) |
| 16 | 5-nitrofuran-2-carboxamide with N-(quinolin-6-yl) |
| 17 | 5-nitrofuran-2-carboxamide with N-(thiophen-3-yl) |
| 18 | 5-nitrofuran-2-carboxamide with N-(thiophen-2-yl) |
| 19 | 5-nitrofuran-2-carboxamide with N-(isoxazol-3-yl) |
| 20 | 5-nitrofuran-2-carboxamide with N-(1H-pyrazol-3-yl) |
| 21 | 5-nitrofuran-2-carboxamide with N-(1-methyl-1H-pyrazol-3-yl) |
| 22 | 5-nitrofuran-2-carboxamide with N-(1-methyl-1H-pyrazol-4-yl) |
| 23 | 5-bromofuran-2-carboxamide with N-(4-acetamidophenyl) |
| 24 | 5-acetamidofuran-2-carboxamide with N-(4-acetamidophenyl) |
| 25 | 5-(methylsulfonyl)furan-2-carboxamide with N-(4-acetamidophenyl) |
| 26 | 5-nitrofuran-2-carboxamide with N-(2-acetamidophenyl) |
| 27 | 5-nitrofuran-2-carboxamide with N-(3-acetamidophenyl) |
| 28 | 5-nitrofuran-2-carboxamide with N-(3-methylphenyl) |

TABLE 1-continued
Compound structures of Example 1 to Example 79 of the present invention
| Ex. | Structure |
|-----|-----------|
| 29 | 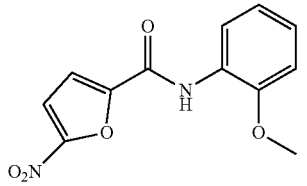 [SMILES: COc1ccccc1NC(=O)c1ccc([N+](=O)[O-])o1] |
| 30 | 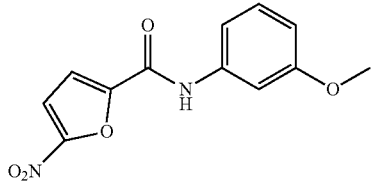 [SMILES: COc1cccc(NC(=O)c2ccc([N+](=O)[O-])o2)c1] |
| 31 | 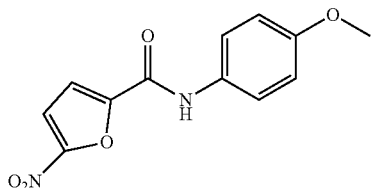 |
| 32 | 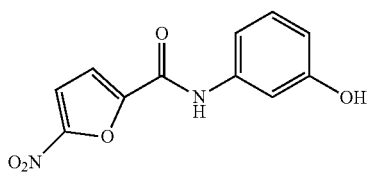 [SMILES: O=C(Nc1cccc(O)c1)c1ccc([N+](=O)[O-])o1] |
| 33 | 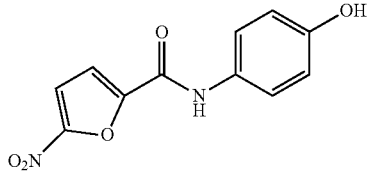 |
| 34 | 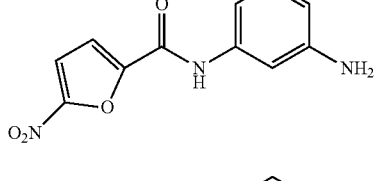 |
| 35 | 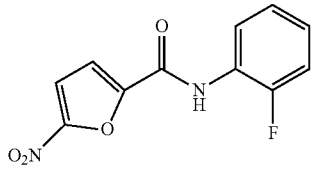 [SMILES: O=C(Nc1ccccc1F)c1ccc([N+](=O)[O-])o1] |
| 36 | 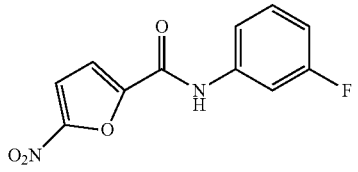 [SMILES: O=C(Nc1cccc(F)c1)c1ccc([N+](=O)[O-])o1] |
| 37 | 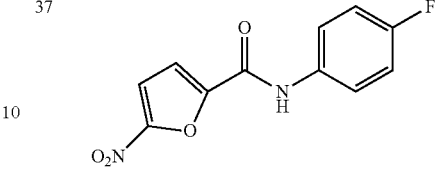 |
| 38 | 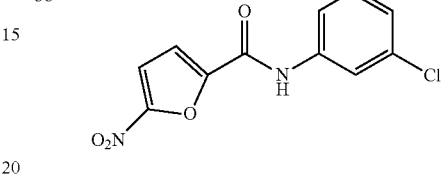 |
| 39 | 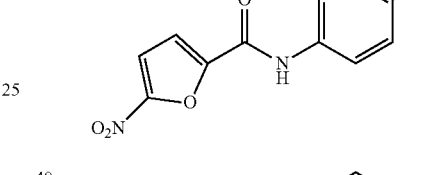 |
| 40 | 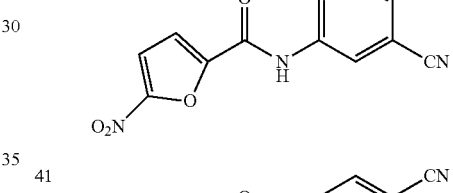 |
| 41 | 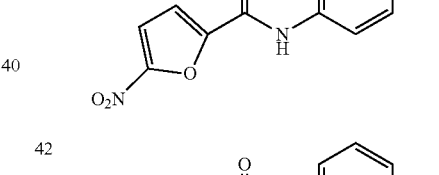 |
| 42 | 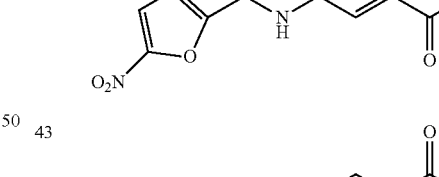 |
| 43 | 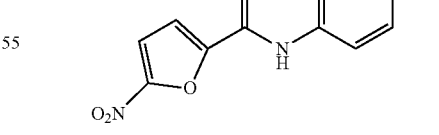 |
| 44 | 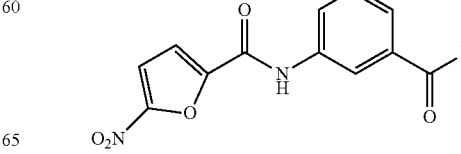 |

TABLE 1-continued

Compound structures of Example 1 to Example 79 of the present invention

| Ex. | Structure |
|---|---|
| 45 | 5-nitrofuran-2-carboxamide N-(4-carbamoylphenyl) |
| 46 | 5-nitrofuran-2-carboxamide N-(3-acetylphenyl) |
| 47 | 5-nitrofuran-2-carboxamide N-(4-(dimethylamino)phenyl) |
| 48 | 5-nitrofuran-2-carboxamide N-(4-morpholinophenyl) |
| 49 | 5-nitrofuran-2-carboxamide N-(4-(4-ethylpiperazin-1-yl)phenyl) |
| 50 | 5-nitrofuran-2-carboxamide N-(4-(2-hydroxyethyl)phenyl) |
| 51 | 5-nitrofuran-2-carboxamide N-(4-(aminomethyl)phenyl) |
| 52 | N,N'-(1,4-phenylene)bis(5-nitrofuran-2-carboxamide) |
| 53 | 5-nitro-N-(3-(methylcarbamoyl)phenyl)furan-2-carboxamide |
| 54 | 5-nitro-N-(3-(dimethylcarbamoyl)phenyl)furan-2-carboxamide |
| 55 | 5-nitro-N-(3-(ethylcarbamoyl)phenyl)furan-2-carboxamide |
| 56 | 5-nitro-N-(3-(isopropylcarbamoyl)phenyl)furan-2-carboxamide |
| 57 | 5-nitro-N-(3-(isobutylcarbamoyl)phenyl)furan-2-carboxamide |
| 58 | 5-nitro-N-(3-(cyclohexylcarbamoyl)phenyl)furan-2-carboxamide |
| 59 | 5-nitro-N-(3-(benzylcarbamoyl)phenyl)furan-2-carboxamide |
| 60 | 5-nitro-N-(3-((2-(dimethylamino)ethyl)carbamoyl)phenyl)furan-2-carboxamide |
| 61 | 5-nitro-N-(3-((2-morpholinoethyl)carbamoyl)phenyl)furan-2-carboxamide |
| 62 | 5-nitro-N-(3-((3-morpholinopropyl)carbamoyl)phenyl)furan-2-carboxamide |

TABLE 1-continued

Compound structures of Example 1 to Example 79 of the present invention

| Ex. | Structure |
|---|---|
| 63 | |
| 64 | |
| 65 | |
| 66 | |
| 67 | |
| 68 | |
| 69 | |
| 70 | 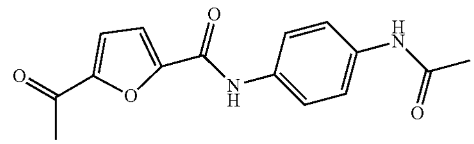 [SMILES: CC(=O)Nc1ccc(NC(=O)c2ccc(C(C)=O)o2)cc1] |
| 71 | 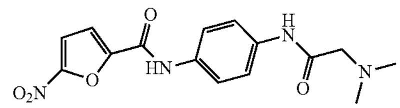 [SMILES: CN(C)CC(=O)Nc1ccc(NC(=O)c2ccc([N+](=O)[O-])o2)cc1] |
| 72 | 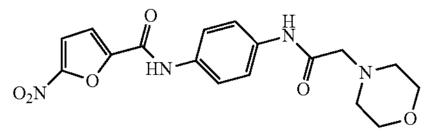 [SMILES: O=C(CN1CCOCC1)Nc1ccc(NC(=O)c2ccc([N+](=O)[O-])o2)cc1] |
| 73 | 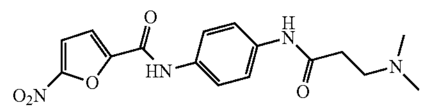 [SMILES: CN(C)CCC(=O)Nc1ccc(NC(=O)c2ccc([N+](=O)[O-])o2)cc1] |
| 74 | 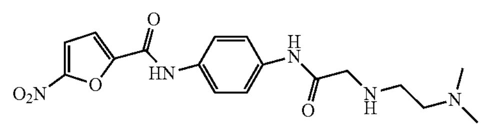 [SMILES: CN(C)CCNCC(=O)Nc1ccc(NC(=O)c2ccc([N+](=O)[O-])o2)cc1] |
| 75 | 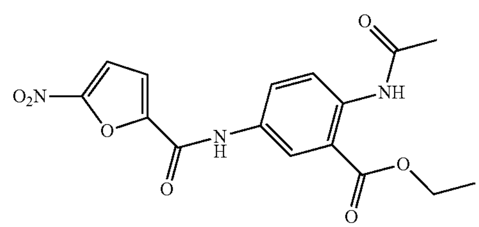 [SMILES: CCOC(=O)c1cc(NC(=O)c2ccc([N+](=O)[O-])o2)ccc1NC(C)=O] |
| 76 | 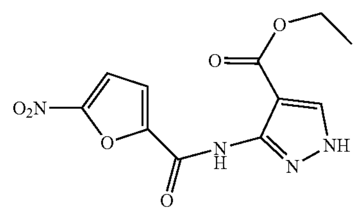 [SMILES: CCOC(=O)c1c[nH]nc1NC(=O)c1ccc([N+](=O)[O-])o1] |
| 77 | 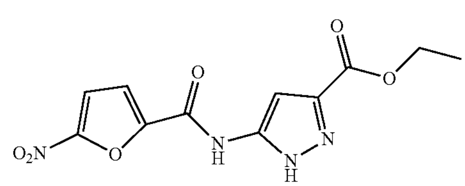 [SMILES: CCOC(=O)c1cc(NC(=O)c2ccc([N+](=O)[O-])o2)[nH]n1] |
| 78 | 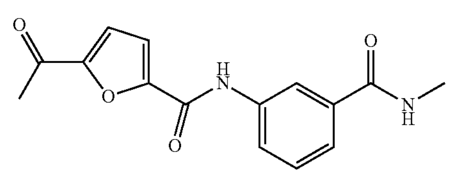 [SMILES: CNC(=O)c1cccc(NC(=O)c2ccc(C(C)=O)o2)c1] |

TABLE 1-continued

Compound structures of Example 1 to Example 79 of the present invention

| Ex. | Structure |
|---|---|
| 79 | 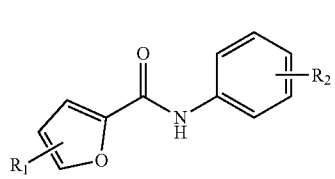 |

TABLE 2

Blood biochemical indexes of rats in Example 3 compound-treated group and control group

| Test item | Control (n = 8) | Example 3 (n = 8) |
|---|---|---|
| Serum sodium (mM) | 146.7 ± 2.0 | 147.3 ± 2.0 |
| Serum potassium (mM) | 4.6 ± 0.1 | 4.8 ± 0.2 |
| Serum chlorine (mM) | 102.0 ± 1.5 | 101.7 ± 1.3 |
| Serum triglyceride (mM) | 0.54 ± 0.05 | 0.68 ± 0.07 |
| Serum high-density lipoprotein (mM) | 0.70 ± 0.02 | 0.71 ± 0.03 |
| Serum low-density lipoprotein (mM) | 0.35 ± 0.03 | 0.34 ± 0.03 |
| Serum cholesterol (mM) | 1.63 ± 0.07 | 1.59 ± 0.06 |
| Serum glucose (mM) | 9.0 ± 0.3 | 9.4 ± 0.3 |

TABLE 3

$IC_{50}$ values of compounds of the present invention for UT-B

| Ex. | $IC_{50}$* (μM) mice | $IC_{50}$* (μM) rats | $IC_{50}$* (μM) human | Activity level |
|---|---|---|---|---|
| 1 | >80 | >80 | 5.44 | ++++ |
| 2 | 5.31 | 1.53 | 1.98 | ++++ |
| 3 | 2.42 | 0.78 | 0.23 | ++++ |
| 4 | >80 | >80 | 21.27 | ++ |
| 5 | 4.24 | 1.03 | 0.84 | ++++ |
| 6 | >80 | >80 | >80 | + |
| 7 | >80 | >80 | 22.88 | ++ |
| 8 | >80 | 31.07 | >80 | + |
| 9 | 18.71 | 20.11 | 2.53 | ++++ |
| 10 | 6.04 | 7.06 | 2.60 | ++++ |
| 11 | 7.57 | 9.21 | 5.80 | ++++ |
| 12 | 4.25 | 8.47 | 2.15 | ++++ |
| 13 | 24.28 | 31.54 | 12.04 | +++ |
| 14 | 10.35 | 6.44 | 3.69 | ++++ |
| 15 | 24.12 | 18.65 | 9.39 | ++++ |
| 16 | 5.08 | 5.49 | 1.64 | ++++ |
| 17 | 14.15 | 17.61 | 17.18 | +++ |
| 18 | 18.22 | 19.25 | 5.63 | ++++ |
| 19 | 10.20 | 30.01 | 3.63 | ++++ |
| 20 | 1.09 | 1.36 | 0.22 | ++++ |
| 21 | 8.51 | 1.10 | 2.21 | ++++ |
| 22 | 33.23 | 9.64 | 15.77 | +++ |
| 23 | 15.10 | 19.82 | 17.95 | +++ |
| 24 | 12.08 | 2.20 | 13.96 | +++ |
| 25 | >80 | 15.77 | 13.66 | +++ |
| 26 | 19.22 | 9.45 | 22.52 | ++ |
| 27 | 0.52 | 0.49 | 0.14 | ++++ |
| 28 | 30.5 | 3.91 | 3.66 | ++++ |
| 29 | 17.07 | 4.11 | 4.87 | ++++ |
| 30 | 9.65 | 1.11 | 2.27 | ++++ |
| 31 | 13.00 | 2.97 | 1.47 | ++++ |
| 32 | 2.39 | 0.67 | 0.91 | ++++ |
| 33 | 11.21 | 3.20 | 1.60 | ++++ |
| 34 | 10.49 | 1.80 | 3.58 | ++++ |
| 35 | 43.76 | 3.80 | 3.62 | ++++ |
| 36 | 9.28 | 1.85 | 3.09 | ++++ |
| 37 | 15.67 | 4.67 | 4.12 | ++++ |
| 38 | 5.81 | 1.05 | 2.91 | ++++ |
| 39 | 27.77 | 10.88 | 26.07 | ++ |
| 40 | 7.85 | 2.77 | 1.00 | ++++ |
| 41 | 10.64 | 1.70 | 3.46 | ++++ |
| 42 | 2.30 | 0.45 | 0.47 | ++++ |
| 43 | 4.56 | 1.99 | 0.71 | ++++ |
| 44 | 0.50 | 0.17 | 0.42 | ++++ |
| 45 | 1.63 | 0.18 | 0.13 | ++++ |
| 46 | 2.46 | 0.49 | 1.84 | ++++ |
| 47 | 2.53 | 2.84 | 4.47 | ++++ |
| 48 | 12.42 | 2.28 | 3.66 | ++++ |
| 49 | 2.79 | 0.76 | 0.53 | ++++ |
| 50 | 10.18 | 8.37 | 5.30 | ++++ |
| 51 | 1.69 | 0.49 | 0.94 | ++++ |
| 52 | 0.52 | 0.27 | 0.65 | ++++ |
| 53 | 0.29 | 0.015 | 0.023 | ++++ |
| 54 | 0.31 | 0.20 | 0.74 | ++++ |
| 55 | 5.41 | 1.21 | 0.88 | ++++ |
| 56 | 9.70 | 1.76 | 3.94 | ++++ |
| 57 | 0.50 | 0.09 | 1.42 | ++++ |
| 58 | 2.63 | 0.90 | 1.77 | ++++ |
| 59 | 1.02 | 0.26 | 0.49 | ++++ |
| 60 | 0.74 | 0.21 | 3.68 | ++++ |
| 61 | 2.61 | 1.09 | 0.54 | ++++ |
| 62 | 4.32 | 1.41 | 3.31 | ++++ |
| 63 | 1.23 | 1.76 | 1.70 | ++++ |
| 64 | 2.79 | 0.32 | 1.08 | ++++ |
| 65 | 4.38 | 18.31 | 23.88 | ++ |
| 66 | 2.22 | 0.87 | 3.29 | ++++ |
| 67 | 2.66 | 1.13 | 2.61 | ++++ |
| 68 | 5.69 | 34.29 | 22.80 | ++ |
| 69 | 5.16 | 2.96 | 12.26 | +++ |
| 70 | 0.85 | 0.11 | 0.054 | ++++ |
| 71 | 5.41 | 0.57 | 1.25 | ++++ |
| 72 | 7.38 | 2.87 | 3.05 | ++++ |
| 73 | 27.19 | 1.30 | 6.61 | ++++ |
| 74 | 9.59 | 1.24 | 3.01 | ++++ |
| 75 | 6.39 | 4.81 | 0.37 | ++++ |
| 76 | 14.95 | — | >80 | + |
| 77 | 11.52 | 7.81 | 1.63 | ++++ |
| 78 | 0.52 | 0.24 | 0.13 | ++++ |
| 79 | 4.94 | 1.10 | 0.82 | ++++ |

*"++++" means that the $IC_{50}$ value of the compound to human UT-B is ≤10 μM, and the inhibitory activity is "strong"; "+++" means that the $IC_{50}$ value of the compound to human UT-B is >10 μM and ≤20 μM, and the inhibitory activity is "slightly strong"; "++" means that the $IC_{50}$ value of the compound to human UT-B is >20 μM and ≤80 μM, and the inhibitory activity is "middle"; and "+" means that the $IC_{50}$ value of the compound to human UT-B is >80, and the inhibitory activity is "weak", wherein the lysis rate of mouse erythrocytes is 40% when the compound of Example 6 is at 80 μm.

What is claimed is:

1. A method for treating diseases related to a urea transporter inhibitor, comprising administering a therapeutically effective amount of a compound represented by formula (I-a) or a pharmaceutically acceptable salt thereof to a patient in need thereof, (I-a)

wherein,
$R_1$ is selected from the group consisting of nitro, halogen, alkylcarbonyl, alkylcarbonylamino, alkylsulfonyl and pyrido groups;
$R_2$ is selected from the group consisting of halogen, hydroxy, amino, cyano, alkenyl, alkynyl, hydroxyalkyl, aminoalkyl, alkoxy, alkylcarbonyl, alkoxycarbonyl, pyrido, alkylcarbonylamino optionally substituted with $R_5$, heterocyclic or cyclic group optionally substituted with $R_5$, heteroarylcarbonylamino optionally substituted with $R_5$, N-alkylamino, N,N-di (alkyl) amino, and aminocarbonyl substituted with $R_3$ and $R_4$;

wherein, $R_3$ and $R_4$ are each independently selected from the group consisting of H, hydroxyl, alkyl, heterocyclic or cyclic group optionally substituted with $R_5$, heterocyclic or cyclic alkyl optionally substituted with $R_5$, heteroaryl or aryl alkyl optionally substituted with $R_5$, N-(alkyl) aminoalkyl, and N,N-di (alkyl) aminoalkyl;

and $R_5$ is selected from the group consisting of alkyl, nitro, alkylcarbonylamino, N-(alkyl) amino, N,N-di (alkyl) amino, N,N-di (alkyl) aminoalkylamino, and heterocyclic or cyclic group.

2. The method according to claim 1, wherein the definitions of each group satisfy one or more of the followings:

$R_1$ is selected from the group consisting of nitro, halogen, $C_{1-6}$ alkyl, $C_{1-6}$ alkylcarbonyl, $C_{1-6}$ alkylcarbonylamino, $C_{1-6}$ alkylsulfonyl and pyrido groups;

$R_2$ is selected from the group consisting of halogen, hydroxyl, amino, cyano, $C_{1-6}$ alkyl, $C_{2-6}$ alkenyl, $C_{2-6}$ alkynyl, hydroxy $C_{1-6}$ alkyl, amino $C_{1-6}$ alkyl, $C_{1-6}$ alkoxy, $C_{1-6}$ alkylcarbonyl, $C_{1-6}$ alkoxycarbonyl, pyrido, $C_{1-6}$ alkylcarbonylamino optionally substituted with $R_5$, 5- to 6-membered heterocyclic or cyclic group optionally substituted with $R_5$, 5- to 6-membered heteroarylcarbonylamino optionally substituted with $R_5$, N-($C_{1-6}$ alkyl)amino, N,N-di($C_{1-6}$ alkyl)amino, and aminocarbonyl substituted with $R_3$ and $R_4$;

wherein, $R_3$ and $R_4$ are each independently selected from the group consisting of H, hydroxyl, $C_{1-6}$ alkyl, 5- to 6-membered heterocyclic or cyclic group optionally substituted with $R_5$, 5- to 6-membered heterocyclic or cyclic $C_{1-6}$ alkyl optionally substituted with $R_5$, 5- to 6-membered heteroaryl or aryl $C_{1-6}$ alkyl optionally substituted with $R_5$, N—($C_{1-6}$ alkyl)amino $C_1$-$C_6$ alkyl, and N,N-di($C_{1-6}$ alkyl)amino $C_{1-6}$ alkyl; and $R_5$ is selected from the group consisting of $C_{1-6}$ alkyl, nitro, $C_{1-6}$ alkylcarbonylamino, N—($C_{1-6}$ alkyl)amino, N,N-di($C_{1-6}$ alkyl)amino, alkyl)amino $C_{1-6}$ alkylamino, and 5- to 6-membered heterocyclic or cyclic group.

3. A method for treating diseases related to a urea transporter inhibitor, comprising administering a therapeutically effective amount of a compound selected from the group consisting of the following compounds (2) to (79), or the pharmaceutically acceptable salts thereof:

(2) N-(4-acetylphenyl)-5-nitrofuran-2-carboxamide;
(3) N-(4-acetamidophenyl)-5-nitrofuran-2-carboxamide;
(4) N-(4-acetamidophenyl)furan-2-carboxamide;
(5) N-phenyl-5-nitrofuran-2-carboxamide;
(7) N-[4-(acetylamino)phenyl]-1H-pyrrole-2-carboxamide;
(8) N-(4-acetamidophenyl)oxazole-5-carboxamide;
(9) N-(4-acetamidophenyl)-5-nitrothiophene-2-carboxamide;
(10) N-(pyridin-2-yl)-5-nitrofuran-2-carboxamide;
(23) N-(4-acetamidophenyl)-5-bromofuran-2-carboxamide;
(24) N-(4-acetamidophenyl)-5-acetamidofuran-2-carboxamide;
(25) N-(4-acetamidophenyl)-5-methylsulfonylfuran-2-carboxamide;
(26) N-(2-acetamidophenyl)-5-nitrofuran-2-carboxamide;
(27) N-(3-acetamidophenyl)-5-nitrofuran-2-carboxamide;
(28) N-(3-methylphenyl)-5-nitrofuran-2-carboxamide;
(29) N-(2-methoxyphenyl)-5-nitrofuran-2-carboxamide;
(30) N-(3-methoxyphenyl)-5-nitrofuran-2-carboxamide;
(31) N-(4-methoxyphenyl)-5-nitrofuran-2-carboxamide;
(32) N-(3-hydroxyphenyl)-5-nitrofuran-2-carboxamide;
(33) N-(4-hydroxyphenyl)-5-nitrofuran-2-carboxamide;
(34) N-(3-aminophenyl)-5-nitrofuran-2-carboxamide;
(35) N-(2-fluorophenyl)-5-nitrofuran-2-carboxamide;
(36) N-(3-fluorophenyl)-5-nitrofuran-2-carboxamide;
(37) N-(4-fluorophenyl)-5-nitrofuran-2-carboxamide;
(38) N-(3-chlorophenyl)-5-nitrofuran-2-carboxamide;
(39) N-(4-chlorophenyl)-5-nitrofuran-2-carboxamide;
(40) N-(3-cyanophenyl)-5-nitrofuran-2-carboxamide;
(41) N-(4-cyanophenyl)-5-nitrofuran-2-carboxamide;
(42) ethyl 3-(5-nitrofuran-2-carboxamido)benzoate;
(43) ethyl 4-(5-nitrofuran-2-carboxamido)benzoate;
(44) N-(3-carbamoylphenyl)-5-nitrofuran-2-carboxamide;
(45) N-(4-carbamoylphenyl)-5-nitrofuran-2-carboxamide;
(46) N-(3-acetylphenyl)-5-nitrofuran-2-carboxamide;
(47) N-(4-dimethylaminophenyl)-5-nitrofuran-2-carboxamide;
(48) N-(4-morpholinylphenyl)-5-nitrofuran-2-carboxamide;
(49) N-(4-(4-ethylpiperazin-1-yl)phenyl)-5-nitrofuran-2-carboxamide;
(50) N-(4-(2-hydroxyethyl)phenyl)-5-nitrofuran-2-carboxamide;
(51) N-(4-aminomethylphenyl)-5-nitrofuran-2-carboxamide;
(52) N,N'-(1,4-phenylene)bis(5-nitrofuran-2-carboxamide);
(53) N-(3-(methylcarbamoyl)phenyl)-5-nitrofuran-2-carboxamide;
(54) N-(3-(dimethylcarbamoyl)phenyl)-5-nitrofuran-2-carboxamide;
(55) N-(3-(ethylcarbamoyl)phenyl)-5-nitrofuran-2-carboxamide;
(56) N-(3-(isopropylcarbamoyl)phenyl)-5-nitrofuran-2-carboxamide;
(57) N-(3-(isobutylcarbamoyl)phenyl)-5-nitrofuran-2-carboxamide;
(58) N-(3-(cyclohexylcarbamoyl)phenyl)-5-nitrofuran-2-carboxamide;
(59) N-(3-(benzylcarbamoyl)phenyl)-5-nitrofuran-2-carboxamide;
(60) N-(3-((2-dimethylaminoethyl)carbamoyl)phenyl)-5-nitrofuran-2-carboxamide;
(61) N-(3-((2-morpholinylethyl)carbamoyl)phenyl)-5-nitrofuran-2-carboxamide;
(62) N-(3-((3-morpholinylpropyl)carbamoyl)phenyl)-5-nitrofuran-2-carboxamide;
(63) N-(4-methyl-3-methylcarbamoylphenyl)-5-nitrofuran-2-carboxamide;
(64) N-(5-methyl-3-methylcarbamoylphenyl)-5-nitrofuran-2-carboxamide;
(65) N-(4-fluoro-3-methylcarbamoylphenyl)-5-nitrofuran-2-carboxamide;
(66) N-(5-fluoro-3-methylcarbomoylphenyl)-5-nitrofuran-2-carboxamide;
(67) N-(4-hydroxy-3-methylcarbamoylphenyl)-5-nitrofuran-2-carboxamide;
(68) $N^1$,$N^3$-dimethyl-5-(5-nitrofuran-2-carboxamido)isophthalamide;
(69) N-(2-methyl-1,3-dihydro-1,3-dioxo-2H-isoindol-5-yl)-5-nitrofuran-2-carboxamide;
(70) N-(4-acetamidophenyl)-5-acetylfuran-2-carboxamide;

(71) N-(4-(2-dimethylamino)acetamidophenyl)-5-nitrofuran-2-carboxamide;
(72) N-(4-(2-morpholinyl)acetamidophenyl)-5-nitrofuran-2-carboxamide;
(73) N-(4-(3-dimethylamino)propionamidophenyl)-5-nitrofuran-2-carboxamide;
(74) N-(4-((2-dimethylamino)ethylamino)acetamidophenyl)-5-nitrofuran-2-carboxamide;
(75) ethyl 2-acetylamino-5-[[(5-nitro-2-furanyl)carbonyl]amino]benzoate;
(78) 5-Acetyl-N-[3-[(methyamino)carbonyl]phenyl]2-furancarboxamide;
and (79) N-3-(ethynylphenyl)-5-nitrofuran-2-carboxamide.

4. The method according to claim 1, wherein the compound represented by formula (I) or the pharmaceutically acceptable salt thereof is one for treating diseases related to the urea transporter inhibitor; or, the drug is a diuretic or antihypertensive drug.

5. The method according to claim 4, wherein the diseases related to the urea transporter inhibitor are edema diseases related to the urea transporter inhibitor.

6. The method according to claim 5, wherein the edema diseases include: cardiogenic edema; nephrogenic edema; hepatogenic edema; dystrophic edema; edema due to connective tissue diseases; allergic edema; endocrine edema; idiopathic edema; venous obstructive edema; lymphatic obstructive edema; inflammatory edema; angioneurotic edema; cerebral edema; laryngeal edema; pulmonary edema and/or lower extremity edema.

7. The method according to claim 6, wherein the cardiogenic edema is a cardiogenic edema due to congestive heart failure and/or constrictive pericarditis;
the nephrogenic edema is a nephrogenic edema due to acute glomerulonephritis, chronic glomerulonephritis, nephrotic syndrome, renal arteriosclerosis and/or renal tubule diseases; the hepatogenic edema is a hepatogenic edema due to liver cirrhosis, liver necrosis, liver cancer and/or acute hepatitis; and
the dystrophic edema is a dystrophic edema due to primary inadequate food intake, secondary malnutrition, digestion and absorption disorders and/or impaired protein synthesis.

8. The method according to claim 4, wherein the diseases related to the urea transporter inhibitor are non-edematous diseases related to the urea transporter inhibitor.

9. The method according to claim 8, wherein the non-edematous dis include: heart failure and/or cardiovascular and cerebrovascular diseases.

10. The method according to claim 9, wherein the heart failure is congestive heart failure, acute heart failure, and/or chronic heart failure; and
the cardiovascular and cerebrovascular diseases are mild hypertension, moderate hypertension, senile systolic hypertension, and/or hypertension with heart failure.

* * * * *